US009878051B2

United States Patent
Koj et al.

(10) Patent No.: US 9,878,051 B2
(45) Date of Patent: Jan. 30, 2018

(54) BORDETELLA PERTUSSIS LOS-DERIVED OLIGOSACCHARIDE WITH PERTUSSIS TOXIN GLYCOCONJUGATE AND ITS APPLICATION IN THE PROPHYLAXIS AND TREATMENT OF INFECTIONS CAUSED BY BORDETELLA PERTUSSIS

(71) Applicant: WROCLAWSKIE CENTRUM BADAŃ EIT+ SP. Z O.O., Wroclaw (PL)

(72) Inventors: Sabina Koj, Dobrodzień (PL); Tomasz Niedziela, Wroclaw (PL); Czeslaw Lugowski, Wroclaw (PL)

(73) Assignee: WROCLAWSKIE CENTRUM BADAN EIT+ SP. Z O.O., Wroclaw (PL)

( * ) Notice: Subject to any disclaimer, the term of this patent is extended or adjusted under 35 U.S.C. 154(b) by 0 days.

(21) Appl. No.: 14/896,222

(22) PCT Filed: Jun. 4, 2014

(86) PCT No.: PCT/IB2014/061944
§ 371 (c)(1),
(2) Date: Dec. 4, 2015

(87) PCT Pub. No.: WO2014/195881
PCT Pub. Date: Dec. 11, 2014

(65) Prior Publication Data
US 2016/0114051 A1    Apr. 28, 2016

(30) Foreign Application Priority Data
Jun. 7, 2013   (PL) .......................... 404247

(51) Int. Cl.
*A61K 39/02* (2006.01)
*A61K 47/48* (2006.01)
*A61K 39/00* (2006.01)

(52) U.S. Cl.
CPC ........ *A61K 47/4833* (2013.01); *A61K 39/099* (2013.01); *A61K 47/481* (2013.01); *A61K 47/4823* (2013.01); *A61K 47/48261* (2013.01); *A61K 2039/6037* (2013.01); *A61K 2039/6087* (2013.01)

(58) Field of Classification Search
None
See application file for complete search history.

(56) References Cited

FOREIGN PATENT DOCUMENTS

| EP | 0471954 A2 | 2/1992 |
|---|---|---|
| WO | 94/04195 | 3/1994 |
| WO | 2011/110531 A2 | 9/2011 |
| WO | 2012/106251 A2 | 8/2012 |

OTHER PUBLICATIONS

Melvin et al. Nat Rev Microbiol. Apr. 2014; 1294:274-288.*
Kubler-Kielb Joanna et al: "Oligosacchande conjugates of Bordetella pertussis and bronchiseptica induce bactericidal antibodies, an addition to pertussis vaccine.", Proceedings of the National Academy of Sciences of The United States of America Mar. 8, 2011, vol. 108, No. 10, Mar. 8, 2011(Mar. 8, 2011), pp. 4087-4092.
Nieoziela Tomasz et al: "Epitope of the vaccine-type Bordetella pertussis strain 186 lipooligosaccharide and antiendotoxin activity of antibodies directed against the terminal pentasaccharide-tetanus toxoid conjugate.", Infection and Immunity Nov. 2005, vol. 73, No. 11. Nov. 2005 (200541)1 pages 7381-7389.
Caroff M et al: "Structure of the Bordetella pertussis 1414 endotoxin", FEBS Letters 20000714 NL, vol. 477, No. 1-2, Jul. 14, 2000(Jul. 14, 2000), pp. 8-14.
Robbins John B et al: "Toward a new vaccine for pertussis.", Proceedings of the National Academy of Sciences of The United States of America Mar. 4, 2014, vol. 111, No. 9, Mar. 4, 2014 (Mar. 4, 2014), pp. 3213-3216.
Anderson P et al: "Immunogens Consisting of Oligosacchardes From the Capsule of Haemophilus-Influenzae Type B Coupled to Diphtheria Toxoid or the Toxin Protein CRM-197", Journal of Clinical Investigation, vol. 76, No. 1, 1985, pp. 52-59.

* cited by examiner

*Primary Examiner* — Oluwatosin Ogunbiyi
(74) *Attorney, Agent, or Firm* — Arrigo, Lee & Guttman LLP

(57) ABSTRACT

The present invention relates to an immunogenic and a non-toxic glycoconjugate comprising *Bordetella pertussis* LOS-derived oligosaccharide and pertussis toxin, a method of preparing such glycoconjugate, the pharmaceutical composition, a vaccine composition containing such glycoconjugate, and an application of the glycoconjugate. The glycoconjugate is prepared as a vaccine component for protection against infections caused by *Bordetella pertussis*.

17 Claims, 28 Drawing Sheets

| I.p | m/z value observed | Interpretation |
|---|---|---|
| 1 | 2312,337 | OS |
| 2 | 1631.54 int. | OS-trisaccharide |
| 3 | 1862.21 | OS – 2$H_2O$ – Hep - Kdo |
| 4 | 1879.84 | OS – 2$H_2O$ – Hep - GlcNAc |
| 5 | 1899.66 | OS – 2$H_2O$ – Hep – GlcNAc + Na |
| 6 | 1964.66 | OS-(Hep+HexA+HexN) |
| 7 | 2039.78 | OS –COOH-$H_2O$ – Hep |
| 8 | 2082.27 | OS – 2$H_2O$ - Hep |
| 9 | 2231.13 int. | OS – COOH-$H_2O$ |
| 10 | 2250.02 int. | OS – $H_2O$ – COOH |
| 11 | 2260.22 | OS – $H_2O$ + 2P – Hep |
| 12 | 2274.67 int. | OS – 2$H_2O$ |
| 13 | 2283.66 | OS – $H_2O$ + 2P – Hep + Na |
| 14 | 2294.10 int. | OS – $H_2O$ |
| 15 | 2239.51 | OS – $H_2O$ + P – Ac |
| 16 | 2316.79 | OS – $H_2O$ + Na |
| 17 | 2329.51 | OS + H2O |
| 18 | 2374.33 int. | OS – $H_2O$ + P |
| 19 | 2452.63 int. | OS – $H_2O$ + 2P |
| 20 | 2496.51 int. | OS – $H_2O$ + PPEtn |
| 21 | 2575.57 | OS – $H_2O$ + P + PPEtn |

Fig. 3E

Table 2

| S1 MH+ | No. | sequence | m/z values observed in the LC-MALDI MS spectra of sPT | m/z values observed in the LC-MALDI MS spectra of OSPT |
|---|---|---|---|---|
| 3434.5784 | 44-73 | YDSRPPEDVFQNGFTAWGNNDNVLDHLTGR | 3435,79 | - |
| 1033,495 | 35-43 | DDPPATVYR | 1033,50 | 1033,04 |
| 2767.1542 | 127-151 | ADNNFYGAASSYFEYVDTYGDNAGR | - | - |
| 2113.9785 | 181-199 | VYHNGITGETTTTEYSNAR | 2114,45 | 2113,91 |
| 1912.9037 | 253-269 | AGEAMVLVYYESIAYSF | - | - |
| 1876.9915 | 152-168 | ILAGALATYQSEYLAHR | 1877,671 | - |
| 1790.7974 | 74-91 | SCQVGSSNSAFVSTSSSR | 1791,74 | - |
| 1552.6696 | 239-252 | QAESSEAMAAWSER | 1551,67 | - |
| 1511.7641 | 114-126 | GTGHFIGYIYEVR | 1512,32 | - |
| 1209.5898 | 93-101 | YTEVYLEHR | 1209,62 | 1209,58 |
| 1119.5471 | 228-238 | MAPVIGACMAR | 1120,58 | - |
| 1062,488 | 102-110 | MQEAVEAER | 1063,48 | - |
| 1019 | 207-215 | ANPNPYTSR | 1019,51 | - |
| 881 | 200-206 | YVSQQTR | 882,59 | - |
| 838,478 | 170-176 | IPPENIR | 838,45 | 839,48 |
| 175 | | R | - | - |
| 1101,663 | 217-227 | SVASIVGTLVR | 1101,67 | - |
| ~~910~~ | ~~35-43~~ | ~~DDPPATVYR~~ | - | - |

Fig. 9G

| 994,579 | 169-176 | RIPPENIR | 994,58 | - |
|---|---|---|---|---|
| 1365,691 | 92-101 | RYTEVYLEHR | 1365,67 | 1365,69 |
| S2 | | | | |
| 3382.4290 | 197-226 | K$^{197}$EEQYYDYEDATFETYALTGISICNPGSSLC | - | - |
| 2332,2043 | 28-49 | STPGIVIPPQEQITQHGGPYGR | 2333,04 | 2331,95 |
| 2366.1703 | 78-99 | GWSIFALYDGTYLGGEYGGVIK | - | - |
| ~~2113.2314~~ | ~~7-26~~ | ~~TLCHLLSVLPLALLGSHVAR~~ | - | - |
| 1995.9155 | 120-137 | NTGQPATDHYYSNVTATR | 1995,93 | 1996,31 |
| 1579.7420 | 153-168 | SGQPVIGACTSPYDGK | - | - |
| 1497.8497 | 179-191 | K$^{179}$MLYLIYVAGISVR | 1498,86 | - <br> potential glycosylation site |
| 1137.5534 | 64-73 | GSGDLQEYLR | 1137,55 | - |
| 1077.5211 | 100-110 | K$^{100}$DGTPGGAFDLK | 1078,48 | - <br> potential glycosylation site |
| 1073.5118 | 111-119 | TTFCIMTTR | 1072,11 | - |
| 992.4295 | 169-175 | YWSMYSR | 992,42 | - |
| 877.4738 | 138-145 | LLSSTNSR | 877,48 | - |
| 872.5200 | 56-63 | ALTVAELR | 872,52 | - |
| 807.4545 | 146-152 | LCAVFVR | 807,47 | - |
| ~~831.3232~~ | ~~1-5~~ | ~~MPIDR~~ | - | - |

Fig. 9G (continued)

| | | | | |
|---|---|---|---|---|
| 569.3405 | 192-196 | VHVSK | - | - |
| 512.2939 | 74-77 | HVTR | - | - |
| S3 | | | | |
| 3379.4657 | 198-227 | EEQYYDYEDATFQTYALTGISLCNPAASIC | - | - |
| 990.635 | 29-38 | VAPGIVIPPK | 990,65 | - potential glycosylation site |
| 2834.4399 | 75-100 | QITPGWSIYGLYDGTYLGQAYGGIIK | - | - |
| 1609.7275 | 154-169 | DGQSVIGACASPYEGR | 1609,73 | - |
| 1529.8218 | 180-192 | LLYMIYMSGLAVR | 1527,46 | - |
| 1337.6120 | 122-133 | K$^{122}$TGQPAADHYYSK | 1337,62 | - potential glycosylation site; deletion of $^{133}$K abolishes the cytotoxicity of PT on CHO cells [32] |
| 1268.6382 | 39-50 | K$^{39}$ALFTQQGGAYGR | 1268,64 | 1268,71 |
| 1218.6075 | 112-121 | K$^{112}$ETFCITTIYK | - | - |
| 1164.6007 | 65-74 | GNAELQTYLR | 1164,60 | 1164,5 |
| 1163.5843 | 101-111 | K$^{101}$DAPPGAGFIYR | - | - |
| 883.3978 | 172-178 | DMYDALR | 882,59 | - |
| 872.5200 | 57-64 | ALTVAELR | 872,52 | - |
| 861.4788 | 139-146 | LLASTNSR | 861,09 | - |
| 807.4545 | 147-153 | LCAVFVR | 807,77 | - |
| 732.4073 | 1-6 | MLINNK | 733,20 | - |

Fig. 9G (continued)

| | | | | |
|---|---|---|---|---|
| 647.2930 | 51-56 | CPNGTR | - | - |
| 569.3405 | 193-197 | VHVSK | - | - |
| 547.3198 | 134-138 | K$^{134}$VTATR | - | - |
| S4 | | | | |
| 932,545 H+ | 43-50 | DVPYVLVK | - | - |
| 2124.0827 | 51-69 | K$^{51}$TNMVVTSVAMKPYEVTPTR | 2124,08 | - potential glycosylation site |
| 1774.8581 | 79-96 | K$^{79}$LGAAASSPDAHVPFCFGK | 1775,5 | - potential glycosylation site |
| 1614.9213 | 128-141 | K$^{128}$QLTFEGKPALELIR | 1615,51 | 1614,8 |
| 1359.6871 | 100-111 | K$^{100}$RPGSSPMEVMLR | 1360,20 | - potential glycosylation site |
| 1245.6884 | 112-121 | AVFMQQRPLR | 1245,69 | - |
| 905.4947 | 70-78 | MLVCGIAAK | - | - |
| 753.3270 | 142-148 | MVECSGK | - | - |
| 692.3800 | 122-127 | MFLGPK | 692,40 | - |
| S5 | | | | |
| 1744,927 H+ | 27-42 | IYSPADVAGLPTHLYK | - | - |
| 3220.5428 | 104-133 | IALTVEDSPYPGTPGDLLELQICPLNGYCE | - | - |
| 3070.4073 | 74-101 | ACLSDAGHEHDTWFDTMLGFAISAYALK | - | - |
| 1503.6719 | 57-69 | NQEFCLTAFMSGR | - | - |

Fig. 9G (continued)

| 1162.6466 | 43-52 | NFTVQELALK | 1162,56 | - |
| | | | | potential glycosylation site |
| 726.4508 | 4-10 | QAGLPLK | - | - |

Fig. 9G (continued)

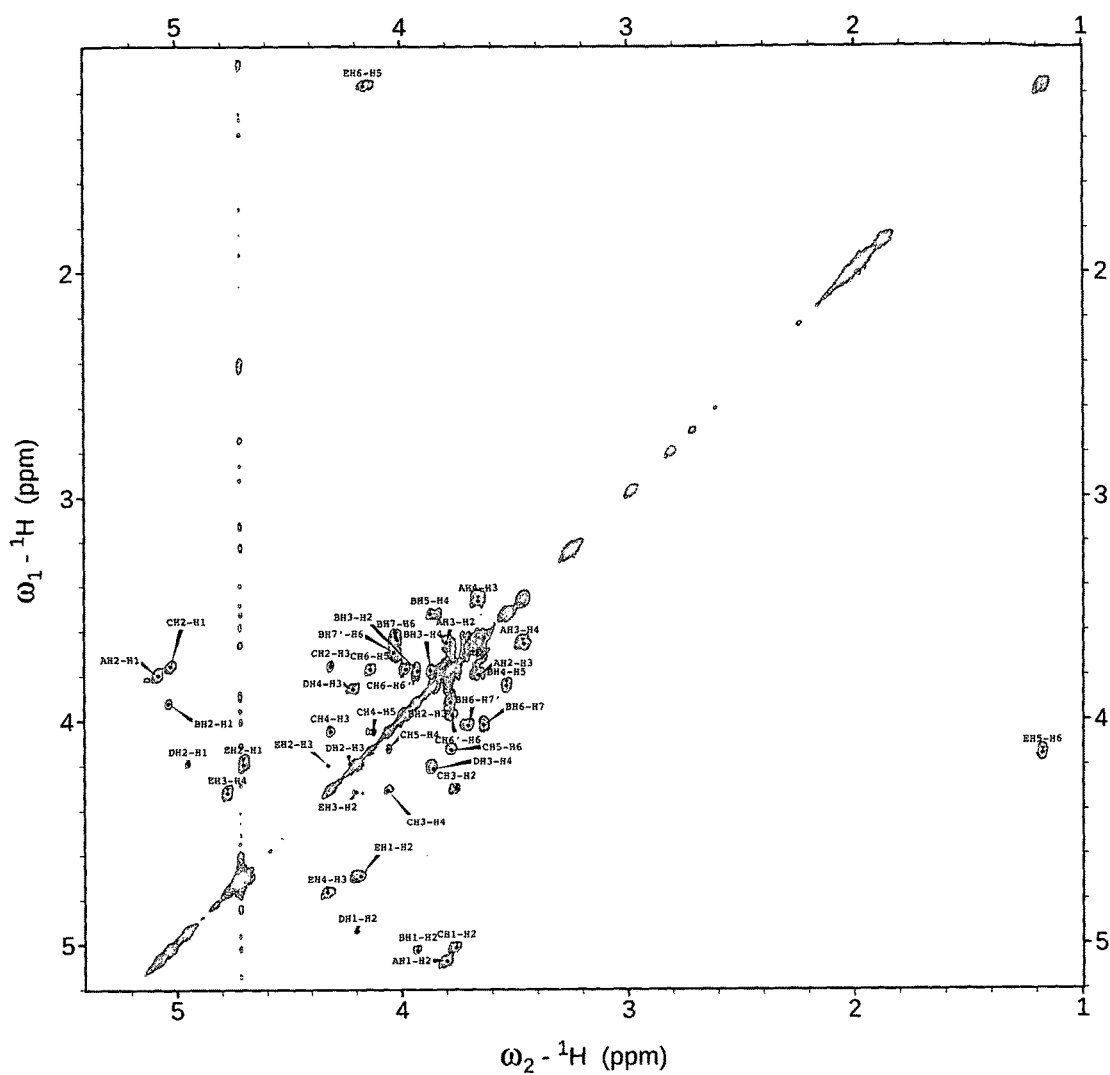
Fig. 11A
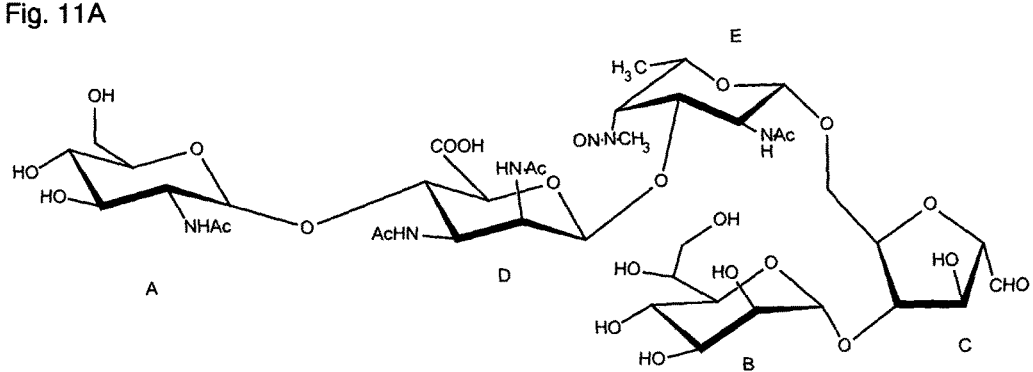

|   | H1/C1 | H2/C2 | H3/C3 | H4/C4 | H5/C5 | H6, H6'/C6 | H7, H7'/C7 CH$_3$CO | H8, H8'/C8 CH$_3$N |
|---|---|---|---|---|---|---|---|---|
| A | 5,079 | 3,803 | 3,659 | 3,463 | 3,681 | 3,761 3,789 | 1,99 | - |
|   | 96,8 | 53,42 | 71,09 | 70,03 | 72,01 | 60,08 | 21,99 174,5 | - |
| B | 5,035 | 3,927 | 3,782 | 3,86 | 3,526 | 4,023 | 3,703 3,648 | - |
|   | 99,28 | 70,34 | 70,6 | 66,14 | 71,91 | 68,88 | 63,07 | - |
| C | 5,022 | 3,762 | 4,312 | 4,055 | 4,128 | 3,777 3,981 |  | - |
|   | 89,31 | 86,03 | 76,23 | 82,7 | 81,87 | 69,89 | - | - |
| D | 4,951 | 4,2 | 4,215 | 3,871 | 3,905 | - | 1,966 | 1,868 |
|   | 100 | 51,75 | 53,44 | 70,41 | 78,26 | 174,5 | 21,94 174,4 | 21,98 174,4(CO) |
| E | 4,702 | 4,186 | 4,325 | 4,774 | 4,156 | 1,175 | 2,025 | 3,244 |
|   | 102,1 | 52,19 | 77,82 | 66,9 | 70,04 | 15,85 | 22,3 174,7 | 37,22 |

Fig. 11D

SEQUENCE LISTING

```
<160> NUMBER OF SEQ ID NOS: 23

<210> SEQ ID NO 1
<211> LENGTH: 6
<212> TYPE: PRT
<213> ORGANISM: Bordetella pertussis

<400> SEQUENCE: 1

Met Phe Leu Gly Pro Lys
1               5

<210> SEQ ID NO 2
<211> LENGTH: 8
<212> TYPE: PRT
<213> ORGANISM: Bordetella pertussis

<400> SEQUENCE: 2

Ala Leu Thr Val Ala Glu Leu Arg
1               5

<210> SEQ ID NO 3
<211> LENGTH: 8
<212> TYPE: PRT
<213> ORGANISM: Bordetella pertussis

<400> SEQUENCE: 3

Arg Ile Pro Pro Glu Asn Ile Arg
1               5

<210> SEQ ID NO 4
```

```
<211> LENGTH: 11
<212> TYPE: PRT
<213> ORGANISM: Bordetella pertussis

<400> SEQUENCE: 4

Ser Val Ala Ser Ile Val Gly Thr Leu Val Arg
1               5                   10

<210> SEQ ID NO 5
<211> LENGTH: 10
<212> TYPE: PRT
<213> ORGANISM: Bordetella pertussis

<400> SEQUENCE: 5

Gly Ser Gly Asp Leu Gln Glu Tyr Leu Arg
1               5                   10

<210> SEQ ID NO 6
<211> LENGTH: 10
<212> TYPE: PRT
<213> ORGANISM: Bordetella pertussis

<400> SEQUENCE: 6

Gly Asn Ala Glu Leu Gln Thr Tyr Leu Arg
1               5                   10

<210> SEQ ID NO 7
<211> LENGTH: 9
<212> TYPE: PRT
<213> ORGANISM: Bordetella pertussis

<400> SEQUENCE: 7

Tyr Thr Glu Val Tyr Leu Glu His Arg
1               5

<210> SEQ ID NO 8
<211> LENGTH: 10
<212> TYPE: PRT
<213> ORGANISM: Bordetella pertussis

<400> SEQUENCE: 8

Ala Val Phe Met Gln Gln Arg Pro Leu Arg
1               5                   10

<210> SEQ ID NO 9
<211> LENGTH: 12
<212> TYPE: PRT
<213> ORGANISM: Bordetella pertussis

<400> SEQUENCE: 9

Ala Leu Phe Thr Gln Gln Gly Gly Ala Tyr Gly Arg
1               5                   10

<210> SEQ ID NO 10
<211> LENGTH: 12
<212> TYPE: PRT
<213> ORGANISM: Bordetella pertussis

<400> SEQUENCE: 10

Arg Pro Gly Ser Ser Pro Met Glu Val Met Leu Arg
1               5                   10

<210> SEQ ID NO 11
<211> LENGTH: 10
<212> TYPE: PRT
```

<213> ORGANISM: Bordetella pertussis

<400> SEQUENCE: 11

Arg Tyr Thr Glu Val Tyr Leu Glu His Arg
1               5                   10

<210> SEQ ID NO 12
<211> LENGTH: 13
<212> TYPE: PRT
<213> ORGANISM: Bordetella pertussis

<400> SEQUENCE: 12

Gly Thr Gly His Phe Ile Gly Tyr Ile Tyr Glu Val Arg
1               5                   10

<210> SEQ ID NO 13
<211> LENGTH: 14
<212> TYPE: PRT
<213> ORGANISM: Bordetella pertussis

<400> SEQUENCE: 13

Gln Leu Thr Phe Glu Gly Lys Pro Ala Leu Glu Leu Ile Arg
1               5                   10

<210> SEQ ID NO 14
<211> LENGTH: 19
<212> TYPE: PRT
<213> ORGANISM: Bordetella pertussis

<400> SEQUENCE: 14

Lys Leu Gly Ala Ala Ala Ser Ser Pro Asp Ala His Val Pro Phe Cys
1               5                   10                  15

Phe Gly Lys

<210> SEQ ID NO 15
<211> LENGTH: 18
<212> TYPE: PRT
<213> ORGANISM: Bordetella pertussis

<400> SEQUENCE: 15

Asn Thr Gly Gln Pro Ala Thr Asp His Tyr Tyr Ser Asn Val Thr Ala
1               5                   10                  15

Thr Arg

<210> SEQ ID NO 16
<211> LENGTH: 19
<212> TYPE: PRT
<213> ORGANISM: Bordetella pertussis

<400> SEQUENCE: 16

Val Tyr His Asn Gly Ile Thr Gly Glu Thr Thr Thr Thr Glu Tyr Ser
1               5                   10                  15

Asn Ala Arg

<210> SEQ ID NO 17
<211> LENGTH: 20
<212> TYPE: PRT
<213> ORGANISM: Bordetella pertussis

<400> SEQUENCE: 17

Lys Thr Asn Met Val Val Thr Ser Val Ala Met Lys Pro Tyr Glu Val
1               5                   10                  15

```
Thr Pro Thr Arg
            20

<210> SEQ ID NO 18
<211> LENGTH: 22
<212> TYPE: PRT
<213> ORGANISM: Bordetella pertussis

<400> SEQUENCE: 18

Ser Thr Pro Gly Ile Val Ile Pro Pro Gln Glu Gln Ile Thr Gln His
1               5                   10                  15

Gly Gly Pro Tyr Gly Arg
            20

<210> SEQ ID NO 19
<211> LENGTH: 30
<212> TYPE: PRT
<213> ORGANISM: Bordetella pertussis

<400> SEQUENCE: 19

Tyr Asp Ser Arg Pro Pro Glu Asp Val Phe Gln Asn Gly Phe Thr Ala
1               5                   10                  15

Trp Gly Asn Asn Asp Asn Val Leu Asp His Leu Thr Gly Arg
            20                  25                  30

<210> SEQ ID NO 20
<211> LENGTH: 19
<212> TYPE: PRT
<213> ORGANISM: Bordetella pertussis

<400> SEQUENCE: 20

Arg Asn Thr Gly Gln Pro Ala Thr Asp His Tyr Tyr Ser Asn Val Thr
1               5                   10                  15

Ala Thr Arg

<210> SEQ ID NO 21
<211> LENGTH: 19
<212> TYPE: PRT
<213> ORGANISM: Bordetella pertussis

<400> SEQUENCE: 21

Val Tyr His Asn Gly Ile Thr Gly Glu Thr Thr Thr Thr Glu Tyr Ser
1               5                   10                  15

Asn Ala Arg

<210> SEQ ID NO 22
<211> LENGTH: 7
<212> TYPE: PRT
<213> ORGANISM: Bordetella pertussis

<400> SEQUENCE: 22

Tyr Val Ser Gln Gln Thr Arg
1               5

<210> SEQ ID NO 23
<211> LENGTH: 35
<212> TYPE: PRT
<213> ORGANISM: Bordetella pertussis

<400> SEQUENCE: 23

Val Thr Pro Thr Arg Met Leu Val Cys Gly Ile Ala Ala Lys Leu Gly
1               5                   10                  15
```

```
Ala Ala Ala Ser Ser Pro Asp Ala His Val Pro Phe Cys Phe Gly Lys
            20              25                  30

Asp Leu Lys
        35
```

BORDETELLA PERTUSSIS LOS-DERIVED OLIGOSACCHARIDE WITH PERTUSSIS TOXIN GLYCOCONJUGATE AND ITS APPLICATION IN THE PROPHYLAXIS AND TREATMENT OF INFECTIONS CAUSED BY BORDETELLA PERTUSSIS

The present invention relates to an immunogenic and non-toxic glycoconjugate comprising *Bordetella pertussis* LOS-derived oligosaccharide and a pertussis toxin, a method of preparing such glycoconjugate, the pharmaceutical composition, a vaccine composition containing such glycoconjugate, and an application of the glycoconjugate. The glycoconjugate is prepared as a vaccine component for protection against infections caused by *Bordetella pertussis*.

The present invention belongs to the field of antibacterial glycoconjugate vaccines design.

*Bordetella pertussis* causes whooping cough, a highly contagious disease involving the respiratory tract, which is especially serious for infants and young children. Despite widespread immunization, in recent years the number of pertussis incidences has increased [19, 20]. The main reason for the resurgence of this vaccine-preventable disease is a waning of vaccine-induced immunity and genetic changes in *B. pertussis* strains [11]. High reactogenicity of the whole-cell pertussis vaccines and better understanding of the molecular function mechanisms of *B. pertussis* virulence factors that are also its major protective antigens have led to the introduction of acellular vaccines which are in continuous development [21, 31, 41, 63, 68]. Commonly used acellular pertussis vaccines contain inactivated pertussis toxin since the toxin is the most immunogenic component of *B. pertussis* [50, 55]. Pertussis toxoid (PTd), diphtheria (DTd) and tetanus toxoids (TTd) were combined into a 3-component vaccine (DTaP). The efficacy of this vaccine against pertussis is approximately 71% and it is lower than for tetanus and diphtheria [69]. All symptoms of tetanus and diphtheria diseases are caused exclusively by toxins, whereas pertussis pathogenesis involves multiple virulence factors. Besides the secretory proteins of *B. pertussis* (e.g. pertussis toxin), surface molecules such as adhesins and endotoxin are involved in pathogenesis of pertussis [18, 37]. Therefore not only toxin-neutralizing activity is required in the immune defense against pertussis, but also bactericidal activity against surface components of *B. pertussis* which ensures the bacterial killing. Therefore besides toxin-neutralizing activity, the bactericidal activity against surface components of *B. pertussis*, ensuring the bacterial killing is required in the immune defense against pertussis.

The bactericidal attack against *B. pertussis* could targeted the highly exposed lipooligosaccharide (LOS) [73]. Actually, antibodies to LOS are found in the sera of patients with bacterial infections [5, 70]. *B. pertussis* endotoxin is lacking a typical O-antigen and thus it constitutes a lipooligosaccharide. *B. pertussis* LOS is composed of a lipid A, a core oligosaccharide and a distal trisaccharide which is a single oligosaccharide unit [10]. Among *B. pertussis* strains there are also strains having LOS devoid of the terminal trisaccharide, which exhibit lower virulence [9, 14]. Similarly to lipopolysaccharides of other Gram-negative bacteria, LOS is also an important factor showing the endotoxic activity [1]. The LOS plays a role in the pathogenesis of pertussis acting in synergy with exotoxins. Thus, LOS together with the tracheal cytotoxin (TCT) and pertussis toxin (PT) causes a destruction of the ciliated cells of the respiratory tract by activation of cytokine-inducible nitric oxide synthase (iNOS) [15, 37]. LOS is lethal in mice sensitized to histamine. It is pyrogenic and mitogenic in spleen cell culture. It activates macrophages and induces the production of TNF-α. Endotoxic activity of lipid A excludes an application of the LOS as a component in pertussis vaccines. However, the removal of the LOS from vaccines reduces their effectiveness, because this component provides adjuvant properties through induction of interleukin-12 (IL-12) and IL-1β that promote the Th1 and Th17 responses, respectively [23, 24, 39].

However, none of the sugar fragments of LOS have been considered as vaccine antigens since they are not immunogenic components. To overcome the problem in the design of vaccines using the LOS, the non-toxic hapten oligosaccharide was conjugated to a carrier protein [27, 28]. Oligosaccharide from *B. pertussis* LOS in its complete form (OS, core oligosaccharide substituted by a distal trisaccharide) is a branched dodecasaccharide with a unique structure. It is an evolutionarily stable component which has been found in its unchanged form in clinical isolates therefore it makes for a suitable vaccine candidate.

Immunogenic conjugates of *B. pertussis* OS with filamentous hemagglutinin (FHA) and *B. pertussis* OS with bovine serum albumin (BSA) have been previously described [32, 33, 34, 35, 81, 84]. Oligosaccharide fragment of *B. pertussis* LOS, a pentasaccharide component conjugated to tetanus toxoid (OS-TTd) was also immunogenic [47]. All the described conjugates of *B. pertussis* oligosaccharide with a carrier protein have induced a strong immune response specific for the oligosaccharide. Moreover, the produced antibodies showed the bactericidal activity specific to LOS presented on *B. pertussis* surface, leading to complement-mediated destruction of the cell [34, 47]. In vivo, the anti-OS bactericidal antibodies eliminate the bacteria from infected individuals [45]. However, the protein carriers employed, that is BSA and TTd, serve as immunogens, but they do not contribute to the pool of antibodies directed against *B. pertussis*. FHA is an adhesin of *B. pertussis* and similarly to LOS it is a surface component. Thus, the abovementioned pertussis vaccines do not combine components that could yield the complete immune response providing the clearance of the pathogen from the organism as well as neutralizing its toxic effects.

In the case of pertussis vaccines, a composition inducing an immune response comprising toxin neutralization and bactericidal activities against *B. pertussis*, has not been devised to date. Pertussis toxin (PT) which is the strongest immunogen of *B. pertussis* in its inactivated form is an essential component of pertussis vaccine [53, 38, 77]. PT belongs to the family of AB-type bacterial toxins and it consists of protomer A (S1 subunit) providing an enzymatic activity and oligomer B responsible for binding to serum glycoproteins and eukaryotic cells (S2 to S5 subunits) [8, 38, 40, 56, 53, 57, 62, 65, 76]. PT is able to initiate two types of cellular responses: lectin-like effects of oligomer B and ADP-ribosylation, which disrupts a signal transduction involving guanine nucleotide binding proteins (G proteins). The oligomer B is required for binding of the holotoxin to a receptor on the surface of a target cell and enables translocation of the protomer A catalytic domain into the cell. Studies on the structure-function relationship of pertussis toxin indicated the amino acid residues involved in the toxic activity. This research have allowed to obtain the toxoid (PTd) which is genetically inactivated by amino acids alterations in the active site of S1 subunit and/or in the oligomer B residues involved in receptor binding [25, 46]. The ongoing clinical trials of a live attenuated vaccine containing the genetically inactivated PT are promising [44].

However, due to multiple amino acid residues involved in activity of the toxin it is necessary to define the sites and subsequently to use the modification to obtain a completely non-toxic PTd. The amino acid residues which were significant for PT interactions include the following residues: His35 and Glu129 of the S1 subunit and the residue no. 105 in S2 and S3 subunits, that is Asn105 and Lys105, respectively [2, 3, 36, 65]. Minute alterations in the PT sequence lead to detoxification of the protein, but its antigenic properties remain unchanged [51, 83]. It can be presumed, that modification or blocking of the PT sites that interact with the target receptors, would inactivate PT. The patent application US005445817 as of Aug. 28, 1995 described the inactivation of the pertussis toxin by conjugation to the *Streptococcus pneumoniae* capsular polysaccharide (Pn14-PT) [82]. However, the generated immune response was exclusively specific for the Pn14.

Detoxification of PT during its toxoid formation may introduce various modifications and conformational changes into the protein structure. The PT inactivation methods include a genetic manipulation by substitution of amino acids (Arg9→Lys and Glu129→Gly) in S1 subunit and chemical modifications of the toxin by formaldehyde, glutaraldehyde, tetranitromethane, hydrogen peroxide or a combination of formaldehyde and glutaraldehyde [25, 51, 53]. The effects of the detoxification reaction on PT have not been precisely defined. Physicochemical, immunochemical, spectroscopic and serological analyses of the toxoids have been performed to determine the sites and the effects of modifications caused by the used methods [59, 61, 71, 72, 75, 77]. PT can be detoxified by modifications at different amino acid positions in its A subunit, B oligomer or both. However, research on pertussis toxoid has indicated that there is a possibility of partial reversion of the toxoid to its active form [26, 52]. This residual pertussis toxin in a vaccine preparation can cause the toxic effects on an immunized organism. Enzymatic activity of PT revealed in the preparation could be responsible for the reactogenicity manifested by hypersensitivity to histamine and allergic reactions.

Residual toxicity of a preparation containing pertussis toxoid is monitored to assess its safety and acceptance as a pertussis vaccine. Residual PT in the PTd preparation may be a result of incomplete inactivation of the toxin or its toxicity reversion [26, 52, 79, 80]. In vivo histamine-sensitization test (HIST) is an official safety test for detecting the residual activity of PT in vaccines. However, the HIST test is a lethal test and difficult to standardize. As an alternative to HIST, an in vitro system based on a selective binding of PT to fetuin and subsequent detection with a polyclonal antibody has been developed for the safety of pertussis vaccine [26]. This analysis differentiates between the ability of PT to preferential binding to fetuin compared to the reduced binding of PTd to fetuin [17]. A system to examine both function of PT based on the carbohydrate binding assay in combination with monitoring of the protomer A activity in an enzyme coupled-HPLC (E-HPLC) assay, has also been developed [80]. Enzymatic activity of PT can also be estimated during its interaction with CHO cells as changes in morphology of these cells [7, 22]. The latest proposed alternative relies on an observation of the translocation and internalization of pertussis toxin and toxoids to the target cell based on the direct immunofluorescence labeling using a confocal microscopy [67].

There is a need for a pertussis vaccine containing immunogenic, but completely inactivated components of *B. pertussis*.

The limited efficacy of currently used pertussis vaccines results from the fact that their components do not induce a complete immune response. As mentioned before, the pertussis vaccine should provide a functional immunity in the form of the toxin neutralization, blocking of bacterial adherence, opsonization, complement activation and bacterial killing [69]. PTd plays an essential role as an antigen for induction of antibodies neutralizing toxic activity of PT. Polyclonal serum against the holotoxin neutralizes its toxic action [29, 54]. However, it was shown that the acellular pertussis vaccine does not have bactericidal activity, which is necessary for immune clearance of the bacteria from respiratory tract [74]. The PTd used in vaccines is a secretory protein, which is loosely associated with the cell, and thus it does not constitute a target for bactericidal antibodies. To overcome this problem, LOS, the main surface component of bacterial cell, was used as the target for bactericidal antibodies that can recognize the surface structure of bacteria and promote killing of bacteria in the presence of complement. It was shown that IgG antibodies against core oligosaccharides of non-capsulated bacteria were protective in humans and induced the complement-dependent bacterial killing [70, 73, 74]. The above-mentioned, anti-pertussis glycoconjugates include OS-tioaminooxylated-BSA conjugate that induced bactericidal antibodies in mice [34] and pentasaccharide-TTd that was immunogenic in rabbits [47]. The pentasaccharide part of the conjugate is a fragment isolated from the LOS of *B. pertussis* 186 and it comprises a distal trisaccharide, a heptose and an anhydromannose. It has been shown that pentasaccharide-TTd conjugate induced antibodies which were able to bind to *B. pertussis* in immunofluorescence assays (FACS). Moreover, using STD-NMR techniques it was confirmed that that epitopes which are involved in antigen-antibody recognition are located in the distal trisaccharide and the heptose.

Anti-PT antibodies produced in response to a vaccine containing only PTd as an antigen of *B. pertussis*, do not kill the bacteria, but they neutralize PT activity. However, the bactericidal activity of antibodies is required for complete clearance of bacteria from the host.

The prior art shows therefore a need for a vaccine comprising an immunogenic components against *B. pertussis* in the form of fully inactivated.

Surprisingly, the present invention provides a vaccine component that is immunogenic and non-toxic at the same time, including the way it was received.

The present invention is a glycoconjugate comprising the *B. pertussis* LOS-derived oligosaccharide (OS) or fragment thereof coupled to pertussis toxin (PT) by a covalent bond.

Preferably, the covalent bond is formed by the reductive amination

Preferably, the OS is isolated from the bacterial cell envelope or it is obtained by chemical synthesis.

Preferably, the OS is a core oligosaccharide (an incomplete glycoform, R), a distal trisaccharide or LOS-derived oligosaccharide fragment isolated by specific degradation, especially with periodate oxidation and deamination.

More preferably, the OS is selected from the oligosaccharides of the formula 1, formula 2, formula 3 or formula 4.

Preferably, the OS is a pentasaccharide isolated from *B. pertussis* LOS or its synthetic equivalent.

More preferably, the pentasaccharide is isolated from *B. pertussis* 186 LOS by deamination.

In a preferred embodiment, the OS is the pentasaccharide depicted by the formula 5.

Preferably, a content of oligosaccharide or fragment thereof in glycoconjugate with PT is 30-50%.

Another aspect of the invention is a pharmaceutical composition comprising a glycoconjugate according to the invention and a pharmaceutically acceptable carrier.

In another embodiment, a vaccine composition comprises the glycoconjugate according to the invention, a pharmaceutically acceptable carrier and optionally an adjuvant.

Preferably, the vaccine composition induces the production of PT-neutralizing antibodies and antibodies that are bactericidal against *B. pertussis*.

Another objective of the invention is a vaccine composition comprising glycoconjugate according to the invention, a pharmaceutically acceptable carrier and optionally an adjuvant for the prevention and treatment of diseases caused by *B. pertussis*.

It is another objective of the invention to provide a method for preparing a glycoconjugate comprising *B. pertussis* LOS-derived oligosaccharide or its fragment coupled to the pertussis toxin, characterized in that the OS is isolated from bacteria or synthesized and then the OS is conjugated to PT by reaction of reductive amination. Subsequently, the obtained OS-PT glycoconjugate is purified.

Preferably, the method comprises the steps of:
a. culture of *B. pertussis*
b. isolation of LOS from bacteria and subsequent isolation of the OS
c. isolation of PT from *B. pertussis* the culture medium
d. activation of OS
e. conjugation of the oxidized OS with PT by reaction of reductive amination
f. purification of the obtained OS-PT glycoconjugate.

Preferably, the *B. pertussis* is grown on Stainer-Scholte liquid medium with an addition of (2,6-di-O-methyl)-β-cyclodextrin.

Preferably, the OS is activated with sodium periodate.

Preferably, the reductive amination is carried out at pH 9.0.

Preferably, the reductive amination is carried out in 0.2 M borate buffer.

Preferably, the OS-PT glycoconjugate is purified by chromatography.

Preferably, a content of oligosaccharide (OS) or fragment thereof in glycoconjugate with PT is 30-50%.

Another aspect of the invention is a glycoconjugate prepared using the methods defined above.

The present invention provides an immunogenic and non-toxic conjugate of *B. pertussis* LOS-derived oligosaccharide with pertussis toxin. This conjugate shows no residual toxicity monitored using the fetuin-binding assay and no interaction in an assay using CHO cells. Pertussis toxin was inactivated by covalent coupling with LOS oligosaccharide. Presumably, in the conjugate, the oligosaccharide blocks PT at the binding sites for fetuin and glycoproteins of eukaryotic cells. The detoxified PT in OS-PT of the present invention retains its antigenic and immunogenic properties. The obtained OS-PT conjugate is a candidate for use in the pertussis vaccine composition as it constitutes a non-toxic and immunogenic combination of the two components of *B. pertussis* and thus generates optimal anti-pertussis response.

The abovementioned conjugate of the oligosaccharide with the pertussis toxin combines surface and secretory components of *B. pertussis*. Antibodies generated in response to the conjugate of the surface antigen, that is LOS, and the secreted PT are expected to neutralize the PT toxic effect and to be bactericidal. A vaccine containing the OS-PT should enhance immunity against pertussis and decrease the number of incidences of this disease. The OS-PT conjugate in vaccine prevents a disease by toxin neutralization and clearance of the pathogen. The conjugate may be an additional component of a complex acellular pertussis vaccine consisting of a secretory proteins. A vaccine comprising the OS-PT induces the production of bactericidal antibodies. Thus, it prevents *B. pertussis* infection and reduces the spread of pertussis among susceptible individuals.

In summary, the present invention demonstrates that *B. pertussis* oligosaccharide coupled covalently to pertussis toxin forms an immunogenic and non-toxic conjugate, and that the conjugation of an oligosaccharide with PT inactivates the toxin. The OS-PT conjugate is devoid of enzymatic activity of the protomer A and binding properties of oligomer B as it has been demonstrated in the invention using in vitro assays. The complementary features of these two components of the conjugate, that is an oligosaccharide and the pertussis toxin which are important for an effective pertussis vaccine are summarized in the table below. The conjugate is a combination of surface component *B. pertussis*, which is the LOS and secretory component, which is pertussis toxin (a). Pertussis toxin is the most potent *B. pertussis* immunogen. When conjugated to an oligosaccharide it induces the strong response directed specifically to this oligosaccharide (b). The pertussis toxin comprises a variety of epitopes recognized by T and B cells (c). On the other hand, an oligosaccharide has a high thermal and chemical stability, and when coupled to a carrier protein it is able to reach the sites of immune cells accumulation that generate a long-lasting and specific immune response to the oligosaccharide (c). The oligosaccharide as a component of the evolutionarily conserved lipooligosaccharide belongs to the "patterns" which are recognized by the innate immune system, whose activation is essential for complete immune response (d). The generated anti-OS *B. pertussis* antibodies show protective properties against strains used in current vaccines as well as against clinical isolates. Conformational variability of the protein carrier allows for better oligosaccharide exposure (d). Conjugation of the oligosaccharide with pertussis toxin forms a non-toxic and immunogenic conjugate, which induces the immune response and produces antibodies with bactericidal and neutralizing properties (e) (Table 1).

TABLE 1

Complementary features of a non-toxic and immunogenic OS-PT conjugate components

| LOS-derived oligosaccharide | Pertussis toxin |
|---|---|
| a) surface component | secretory component |
| b) specificity | immunogenicity |
| c) stability | multivalency |
| d) conservative | flexibility |
| e) bactericidal antibodies | toxin-neutralizing antibodies |

The invention presents an immunogenic and non-toxic conjugate of *Bordetella pertussis* LOS-derived oligosaccharide and pertussis toxin (OS-PT) intended as a vaccine that protects against infection and diseases caused by *B. pertussis*. The conjugate is capable of eliciting antibodies to both of its components, oligosaccharide and PT. Thus, it induces a production of type-specific and protective antibodies against *B. pertussis*. Antibodies generated in response to the conjugate neutralize the toxic effect of PT and have bactericidal activity against *B. pertussis*. These antibodies promote a bacterial killing involving a complement. Therefore, the OS-PT conjugate induces a protective effect by neutralization of the toxin and clearance of *B. pertussis* from the host.

The present invention refers to an OS-PT conjugate in which the PT component was rendered non-toxic during the coupling reaction. For the conjugation reaction the pertussis toxin and the LOS oligosaccharide are used in quantities which cause the toxin inactivation. Preferably, a content of an oligosaccharide in the PT-glycoconjugate is 30-50%. Preferably, a content of an oligosaccharide or fragment thereof in glycoconjugate with PT is 49%. Inactivation of PT in OS-PT preparation is monitored in in vitro assays, such as ELISA test with fetuin and an assay using CHO cells. The OS-PT conjugates with the substitution of 30 and 49% were not active in the fetuin-binding test and the CHO cells assay.

The invention also provides methods for the preparation of the immunogenic and non-toxic oligosaccharide-pertussis toxin conjugate. This method allows for obtaining these two components of the conjugate, that is a LOS-derived oligosaccharide and a protein carrier, that is a pertussis toxin, from the culture of *B. pertussis*, simultaneously. The possible isolation of both antigens from one source accelerates the vaccine preparation. The oligosaccharide of the invention can be obtained by chemical synthesis.

The oligosaccharide-pertussis toxin conjugate according to the invention is obtained by reductive amination. The conjugation reaction is carried out in 0.2 M borate buffer at pH 9.0.

The present invention relates to a method for the preparation of the conjugate of *B. pertussis* LOS oligosaccharide with the pertussis toxin comprising the steps (Scheme 1):
1. The culture of *B. pertussis* using Stainer-Scholte liquid medium.
2. Isolation of LOS from bacteria and subsequent isolation of an oligosaccharide.
3. Isolation of PT from *B. pertussis* culture medium.
4. Activation of an OS with sodium periodate, yielding the oxidized OS.
5. Conjugation of the oxidized OS and PT by reductive amination.
6. Purification of the OS-PT by chromatography.

Scheme 1. Procedure of the OS-PT conjugate preparation.

culture of *B. pertussis*
↓ isolation ↓
LOS        PT
↓ hydrolysis
OS
↓ OS activation
OS oxidized
↓ conjugation
OS-PT conjugate Following the OS-PT conjugate preparation procedure, the oligosaccharide content in the obtained PT-glycoconjugate is determined. The inability of OS-PT to bind to fetuin and no interaction with CHO cells are tested in in vitro assays.

In one aspect, the vaccine is a non-toxic and immunogenic conjugate of oligosaccharide fragment from *B. pertussis* LOS with pertussis toxin. *B. pertussis* LOS oligosaccharide fragment of the present invention may be any OS fragment causing inactivation of the toxin as a result of covalent linking. Oligosaccharide fragment of *B. pertussis* LOS used for conjugation with pertussis toxin may be selected from the following:

1. a core oligosaccharide (an incomplete form, R)
2. a distal trisaccharide isolated or obtained by chemical synthesis
3. oligosaccharide fragments derived from LOS by specific degradation (e.g. deamination, mild hydrolysis, etc.)

In one aspect of the invention, the vaccine is a non-toxic and immunogenic conjugate of pertussis toxin with a pentasaccharide, in which the pentasaccharide is isolated from *B. pertussis* 186 LOS by deamination or it is a synthetic equivalent thereof. The pertussis toxin and the pentasaccharide of LOS are used for the conjugation reaction in amounts causing a substitution of the protein that inactivates the toxins. Surprisingly, a single step detoxification effect is achieved without the need for detoxification by chemical or genetic methods. The glycoconjugate of the pentasaccharide-PT shows no binding capacity in an ELISA with fetuin.

The invention provides a formulation of the OS-PT conjugate to use as a vaccine against *B. pertussis*. This conjugate may constitute an additional component of a pertussis vaccine, besides *B. pertussis* protein antigens, that acts only by neutralization of toxins. The antibodies produced against components of the vaccine except for LOS do not promote the complement-dependent killing. However, because many virulence factors are involved in the pertussis pathogenesis, including LOS, a direct destructive bactericidal activity is essential. A vaccine containing the OS-PT induces production of bactericidal antibodies and ensures clearance of bacteria from the host. Thus it prevents *B. pertussis* infection and hampers the disease spread among susceptible individuals.

The term "oligosaccharide" (OS) of the present invention relates to an oligosaccharide or its fragments isolated from *B. pertussis* lipooligosacccharide (LOS). The oligosaccharide of the invention may also be prepared by chemical synthesis. The *B. pertussis* oligosaccharide used for conjugation with PT is a core oligosaccharide substituted by a distal trisaccharide (OS, a complete form, RS). The OS is a branched dodecasaccharide having the following structure (FORMULA 1):

(FORMULA 1)

```
                                          α-D-GlcpN-(1-7)+
                                                 |
                                 α-D-GlcpA-(1-2)-L-α-D-Hepp-(1-3)+
                              α-D-GalpNA-(1-6)+                  |
                                           |                     |
α-D-GlcpNAc-(1-4)-β-D-Manp2NAc3NAcA-(1-3)-β-L-Fucp2NAc4NMe-(1-6)-α-D-GlcpN-(1-4)-β-D-Glcp-(1-4)-L-α-D-Hepp-(1-5)-Kdop
                                           |                                                                4
                                           |                                                                ⋮
                                  L-α-D-Hepp-(1-4)+                                                    [EtNPP]$_{n=0,1}$
```

In one aspect of the invention, the vaccine is a conjugate of *B. pertussis* LOS-derived oligosaccharide fragment and pertussis toxin. "The oligosaccharide fragment" of *B. pertussis* LOS of the present invention is any fragment of the OS causing inactivation of pertussis toxin by a covalent coupling.

*B. pertussis* LOS oligosaccharide fragment used for conjugation to pertussis toxin can be any fragment selected from the group enumerated below:

1. a core oligosaccharide (an incomplete form, R)

(FORMULA 2)

```
                          α-D-GlcpN-(1-7)+
                                 |
                 α-D-GlcpA-(1-2)-L-α-D-Hepp-(1-3)+
              α-D-GalpNA-(1-6)+                  |
                           |                     |
             α-D-GlcpN-(1-4)-β-D-Glcp-(1-4)-L-α-D-Hepp-(1-5)-Kdop
                           |                                4
                           |                                ⋮
                  L-α-D-Hepp-(1-4)+                    [EtNPP]$_{n=0,1}$
```

2. a distal trisaccharide isolated or obtained by synthesis

α-D-GlcpNAc-(1-4)-β-D-Manp2NAc3NAcA-(1-3)-β-L-Fucp2NAc4NMe  (FORMULA 3)

3. LOS-derived oligosaccharide fragments obtained by specific degradation, such as:
a) the periodate oxidation product b) the deamination product The following structures correspond to oligosaccharide fragments of *B. pertussis* 186 LOS obtained by the reaction of deamination and purified from the pentasaccharide containing the terminal trisaccharide (Method 8). The following compounds have been identified in MALDI-TOF MS spectra of a non-soluble fraction containing products of the LOS deamination (FIG. 12 B).

A)
```
α-D-GlcpA-(1-2)-L-α-D-Hepp-(1-3)+
                                |
                β-D-Glcp-(1-4)-L-α-D-Hepp-(1-5)-Kdop
```

B)
```
                α-D-GlcpN-(1-7)+
                       |
α-D-GlcpA-(1-2)-L-α-D-Hepp-(1-3)+
                                |
                β-D-Glcp-(1-4)-L-α-D-Hepp-(1-5)-Kdop
```

C)
```
                α-D-GlcpN-(1-7)+
                       |
α-D-GlcpA-(1-2)-L-α-D-Hepp-(1-3)+
α-D-GalpNA-(1-6)+               |
               |                |
               β-D-Glcp-(1-4)-L-α-D-Hepp-(1-5)-Kdop
```

In one aspect of the invention, the vaccine is a conjugate of pertussis toxin with the pentasaccharide isolated by deamination of *B. pertussis* 186 LOS or a synthetic pentasaccharide. The pentasaccharide includes immunodominant epitopes of LOS, which include the terminal trisaccharide and the terminal heptose. The pentasaccharide in the glycoconjugate composition possesses the following structure (FORMULA 5):

(FORMULA 4)

```
β-D-Manp2NAc3NAcA-(1-3)-β-L-Fucp2NAc4NMe-(1-6)-α-D-GlcpN-(1-4)-β-D-Glcp-(1-4)-L-α-D-Hepp-(1-5)-Kdop-CHO
                                                                                              4
                          |                                                                   ⋮
                  L-α-D-Hepp-(1-4)+                                                      [EtNPP]$_{n=0,1}$
```

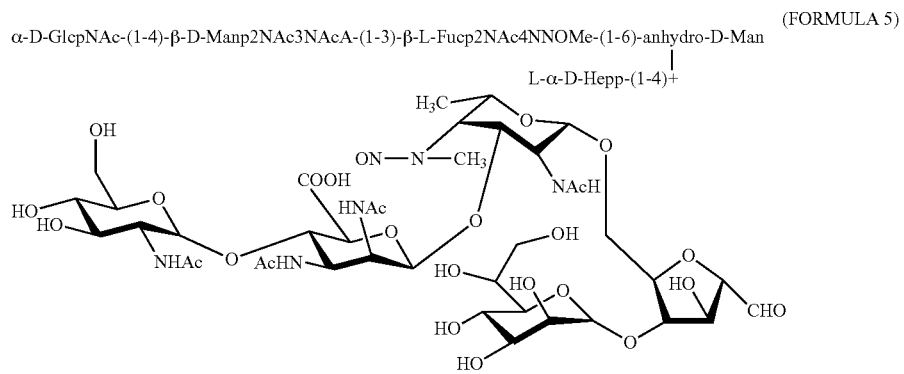

(FORMULA 5)

α-D-GlcpNAc-(1-4)-β-D-Manp2NAc3NAcA-(1-3)-β-L-Fucp2NAc4NNOMe-(1-6)-anhydro-D-Man
|
L-α-D-Hepp-(1-4)┘

On the basis of literature data [4, 13] it can be assumed that this pentasaccharide is a sugar fragment of *B. pertussis* LOS, which is generated as a result of endosomal processing of LOS by deaminative depolymerization. The deaminated OS may be a fragment of LOS presented to T cells and thus it may induce the production of specific antibodies. The depolymerized LOS may make for an optimal vaccine component.

The coupling of the pentasaccharide to pertussis toxin by reductive amination forms a non-toxic glycoconjugate. Such pentasaccharide-PT glycoconjugate is not capable of binding to fetuin in ELISA test.

The term *B. pertussis* "lipooligosaccharide" indicates that endotoxin of this bacterium is devoid of a typical O-antigen, which is the O-specific polysaccharide. LOS is not a complex, polymeric molecule, but similarly to lipopolysaccharides (LPS) of other Gram-negative bacteria, it is an essential virulence factor and a protective antigen [1, 73]. In the case of *B. pertussis*, an oligosaccharide is exposed at the surface of the cell.

The term "conjugate" in this invention means a covalent coupling of a hapten oligosaccharide with a carrier protein, which is pertussis toxin, in order to render the OS more immunogenic. The conjugation is used to obtain a formulation that modulates antibody response to oligosaccharide.

The term "immunogenic" means "inducing immune response" such as a production of antibodies. An immunogenic oligosaccharide-carrier protein conjugate induces the production of antibodies specific for an oligosaccharide. The OS component of LOS applied to the conjugation in the present invention includes a terminal trisaccharide and terminal heptose both coupled to a glucosamine which are epitopes recognized by sera of mice immunized with *B. pertussis [*5, 47, 34].

The term "pertussis toxin" (PT) refers to an exotoxin secreted by *B. pertussis*. PT is a protein of molecular weight about 105 kDa and belongs to the AB-type bacterial toxins [8, 38, 40, 56, 57, 58, 62, 65, 76]. It consists of the A subunit having enzymatic activity and the B oligomer exhibiting binding activity to glycoproteins of serum and eukaryotic cells. These two activities of PT are monitored in the interaction test using the CHO cells (the test of A protomer activity) and the fetuin binding assay (the test of B oligomer activity). PT in this invention can be prepared by various isolation methods known in the art [49, 60, 64, 66].

The invention also provides methods for preparation of the immunogenic and non-toxic conjugate of an oligosaccharide and pertussis toxin. The oligosaccharide is obtained by the water-phenol LOS extraction according to the method of Westphal et al, followed by acid hydrolysis of the LOS and subsequent purification processes. PT is isolated by ion exchange chromatography [49, 66].

The OS-PT conjugate is not toxic in both fetuin binding assay and the test using CHO cells. These safety tests are defined as assays for pertussis vaccine. The term "safety tests for pertussis vaccines" means the methods of monitoring of the PT residual activity in the acellular and whole-cell vaccines [79]. The residual PT activity in the vaccines containing PTd may be due to an incomplete inactivation or the reversion to toxicity. There are two methods of establishing the active PT in vaccine preparations: the histamine sensitization test (HIST) and a test using CHO cells. These methods are used to determine the biological activity of the preparation. The safety tests are used to ensure that the PT levels in vaccines are at acceptable level (LOQ, <Limit-of-quantification> for the PT is 8 ng/ml of the vaccine preparation) [26]. An international PT reference material (JNIH-50) is defined as the standard PT preparation (sPT).

The OS-PT conjugate can be obtained using the methods of conjugation known in the art. The term "conjugation methods known in the art" encompasses the methods commonly used in the preparation of conjugates. Direct conjugation reactions, reactions employing a linker, reactions with an initial activation of a protein or an oligosaccharide are the methods commonly used for conjugation [27, 28, 32, 33, 34, 35]. The oligosaccharide-pertussis toxin conjugate described herein is obtained by the reductive amination. The conjugation reaction is carried out in 0.2 M borate buffer at pH 9.0. The term "reductive amination" as used herein means that during the reaction a covalent linkage of oxidized LOS oligosaccharide with toxin is formed, followed by reduction of the created bond. The modified Kdo residue of an oligosaccharide reacts with the free amino group of the protein to form a stable conjugate in the presence of a reducing agent. This conjugation of an oligosaccharide and pertussis toxin results in inactivation of the toxin.

We have demonstrated the inability of the OS-PT glycoconjugate to bind to fetuin and similarly the OS-PT glycoconjugate has no effect in an interaction with the CHO cells. Detoxification of pertussis toxin by attachment of the oligosaccharide is a result of blocking of the protein binding sites. During conjugation, an oligosaccharide can bind to the terminal amino groups of the subunits and the amine group of lysine residues in the B oligomer. The enzymatically active S1 subunit contains no lysine, therefore the oligosaccharide can only be bound to its N-terminus. Coupling of the N-terminal residue of the S1 subunit with an oligosaccharide may impair its active site conformation and consequently abolish its enzymatic activity. However, mass spectrometry analysis of the trypsin-digested OS-PT, has indicated a signal corresponding to the peptide possessing an unmodified N-terminal residue. This suggests that the N-terminus of the S1 subunit is not available for the oligosaccharide and no coupling of the oligomer A with OS has occurred (FIG. 9 F). Thus, the modification of the B oligomer, which is a domain responsible for the toxin binding activity, appears to be sufficient to detoxify the protein. Presumably, the modified B oligomer is not able to bind to the CHO cell receptor (N-glycosylated protein) and consequently there is no release of the A oligomer and the enzymatic activity is not revealed. The reported research on the structure-function relationship indicated that the S3 subunit is involved in anchoring of the PT in the membrane with subsequent translocation of the S1 subunit [56, 57]. However, the studies using antibodies against protective determinants of the S2 subunit demonstrated that these antibodies inhibited the binding of PT to fetuin, but they had no affect on the interaction with the CHO cell. In depth analysis has pointed the amino acids residue no. 105 in the S2 and S3 subunits, as the one involved in binding to glycoproteins on the cell. As a result of conjugation PT with an oligosaccharide, the binding sites on the subunits S2 and S3 of PT may be blocked, as demonstrated by the loss of interactions with fetuin and with the CHO cells. The effects of the formaldehyde on the PT, that is a crosslinking of the protein by modification of lysine residues on the surface provides an additional indication that the modification of lysine residues inactivates PT. It has been shown that modification of the immunofunctional sites of PT by formaldehyde leads to a non-toxic toxoid [42]. However, despite the structural modification, toxoid maintains its immunogenicity and thus it induces the protective immune response through production of antibodies neutralizing the toxin. Free c-amino groups of lysine are involved in the attachment of the B oligomer of the toxin to the target cell surface. Acetamidation of lysine residues reduced the oligomer B-dependent activities (mitogenicity, promoting of lymphocytosis, histamine sensitization, adjuvanticity and an increased vascular permeability) [48].

The conjugation is carried out in borate buffer at pH 9.0. The reaction conditions are essential for the conjugation of OS with PT because as it was demonstrated that PT is unstable in the pH range 4-8 [82].

The OS-PT conjugate induces the production of antibodies specific for an oligosaccharide. The OS-PT conjugate also induces the production of anti-PT antibodies neutralizing the toxic effects of B. pertussis. The term "neutralizing antibodies" means that the pertussis toxin in the glycoconjugate adds the anti-toxin antibodies to a pool of protective anti-OS antibodies. The neutralizing properties of serum induced by the OS-PT enhance the protective anti-pertussis response.

This conjugate combines a surface component, which is the exposed LOS fragment of B. pertussis, namely OS and a secretory protein of B. pertussis such as PT. The antibodies generated in response to the conjugate of the surface OS and the secretory PT neutralize the toxic effect of PT and are bactericidal. The activity of antibodies has been demonstrated using a CHO cells assay and a bactericidal assay. The anti-OS-PT antibodies inhibited the action of PT on the CHO cells and showed the bactericidal activity in the presence of the rabbit complement. The antibodies were able to recognize the LOS on B. pertussis cells and to promote complement-dependent bacterial killing. The vaccine consisting of the OS-PT should provide immune response that prevents from the disease by toxins neutralization and by clearance of the bacteria from the respiratory tract. Thus, it prevents infection caused by B. pertussis and limits the spread of the disease among susceptible individuals. The conjugate may constitute an additional component of an acellular pertussis vaccine consisting only of secretory proteins, such as PTd and FHA.

The invention also provides a pharmaceutical formulation characterized in that it comprises an immunogenic and non-toxic conjugate of the OS-PT. In one embodiment, the composition may contain adjuvants, stabilizers and solvents which are acceptable in the vaccine formulations.

The term "adjuvant" refers to a substance which enhances the post-vaccinal immune response to the administered antigen. The mechanism of action relies on slowing down the release of an antigen and providing a "danger signal" to stimulate the immune system. An adjuvant suitable for the vaccine formulation belongs to the group consisting of: inorganic salts (aluminum phosphate, calcium phosphate), aluminum hydroxide, ISCOM, liposomes, monophosphoryl lipid A (MPL), muramyl dipeptide.

The invention provides a preparation of an immunogenic and the non-toxic oligosaccharide-PT conjugate for use as a vaccine for protection against infections caused by B. pertussis.

In the present invention, an immunogenic and a non-toxic conjugate of a LOS-derived oligosaccharide from Bordetella pertussis 186 with pertussis toxin was prepared as a vaccine for prevention and treatment of diseases caused by B. pertussis. As it is a potential vaccine antigen the immunochemical, serological and immunological properties thereof have been investigated.

BRIEF DESCRIPTION OF THE DRAWINGS

FIGS. 3A to 3F. MALDI-TOF MS spectra of B. pertussis preparations: whole cell, LOS, OS and oxidized OS and a table of signals interpretation. Spectra were obtained using an Autoflex III instrument, Bruker Daltonics. DHB was used as a matrix.

FIG. 3A. MALDI-TOF MS of B. pertussis whole cells in the m/z range corresponding to the ions of LOS, recorded in negative-ion, linear mode.

FIG. 3B. MALDI-TOF MS of B. pertussis 186 LOS recorded in the negative-ion, linear mode.

FIG. 3C. MALDI-TOF MS B. pertussis 186 LOS recorded in the negative-ion, reflectron mode.

FIG. 3D. MALDI-TOF MS of B. pertussis 186 OS recorded in the positive-ion, reflectron mode.

FIG. 3E. Interpretation of ions corresponding to the signals of molecules observed in the MALDI-TOF MS spectrum of B. pertussis 186 LOS recorded in the negative-ion, reflectron mode, where: Hep—heptose, PPEtN—pyrophosphorylethanolamine, P—phosphate, Ac—acetyl group, $H_2O$—water, $C_{14}OH$—fatty acid; int.—signals with the highest intensities.

FIG. 3F. MALDI-TOF MS spectra of the OS and the oxidized OS recorded in the linear, negative-ion mode. The difference of 30 Da (a loss of the HCHO—fragment) indicates that the oligosaccharide was oxidized with 0.01 M sodium periodate. The signal at m/z 2279.5 corresponds to the oxidized form of the OS.

FIG. 6A. Interaction analysis of PT and the OS-PT on the CHO cells. A) a positive control—62 ng/ml of sPT; B) 156 ng/ml of OS-PT; C) a negative control; D) 130 µg/ml of OS-PT; E) 0.9 µg/ml of PT. The observations were performed using Axio Vert. A1 (Zeiss) at a lens magnification of 10.

FIG. 6B. Pertussis toxin neutralization test by the anti-OS-PT antibodies (serum). a) serum no. 3239 diluted 1:32; b) serum no. 3239 diluted 1:4, c) serum no. 3271 diluted 1:64; d) non-diluted serum no. 3271, e) a negative control (CHO cells); f) a positive control (CHO cells with PT). The observations were performed using Axio Vert. A1 at a lens magnification of 20.

FIG. 9A. MALDI-TOF MS spectrum of sPT. SA was used as a matrix.

This assignment of PT amino acid residues includes the signal sequences and therefore it differs from the numbering of PT sequence presented in the description of the invention.

Figure 9A:
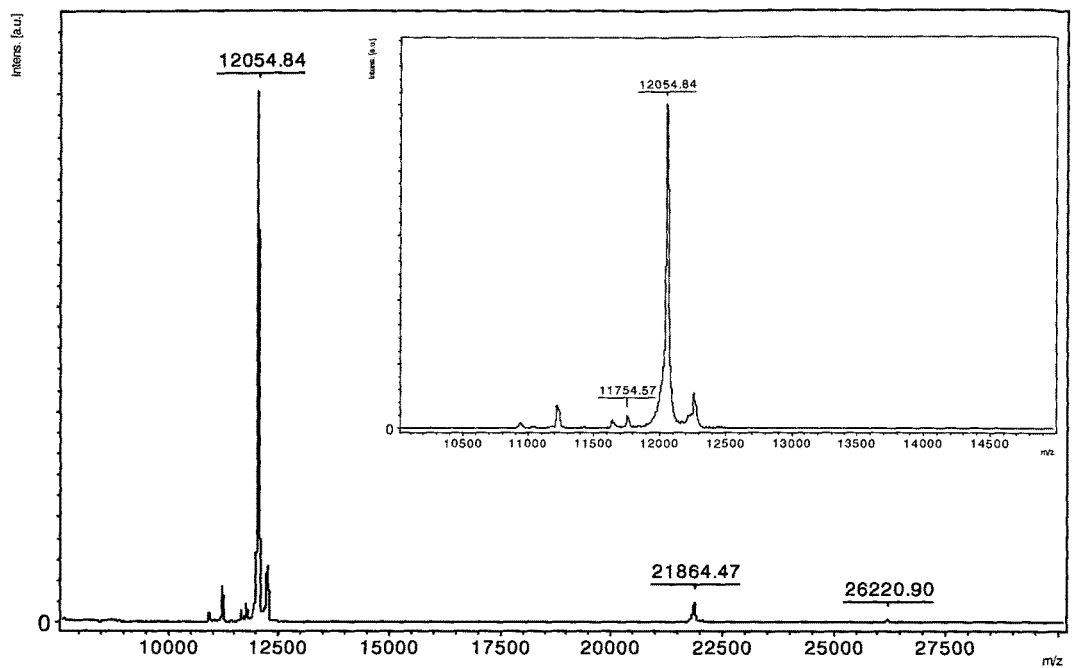
FIGS. 9A and 9G. MALDI-TOF MS spectra of PT and the OS-PT. The spectra were acquired in positive-ion mode (Autoflex III or Ultraflex, Bruker Daltonics).
Figure 9B:
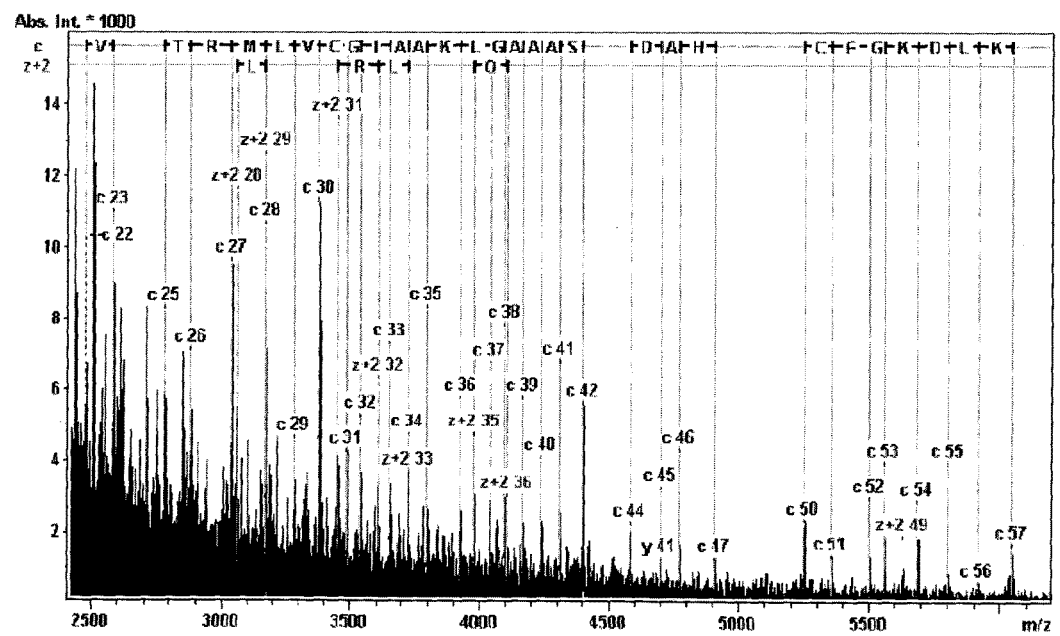
FIG. 9B. ISD spectrum of sPT. Diaminonaphthalene (DA) was used as a matrix. This analysis allowed for the determination of the sequence corresponding to the S4 fragment of PT.
Figure 9C:
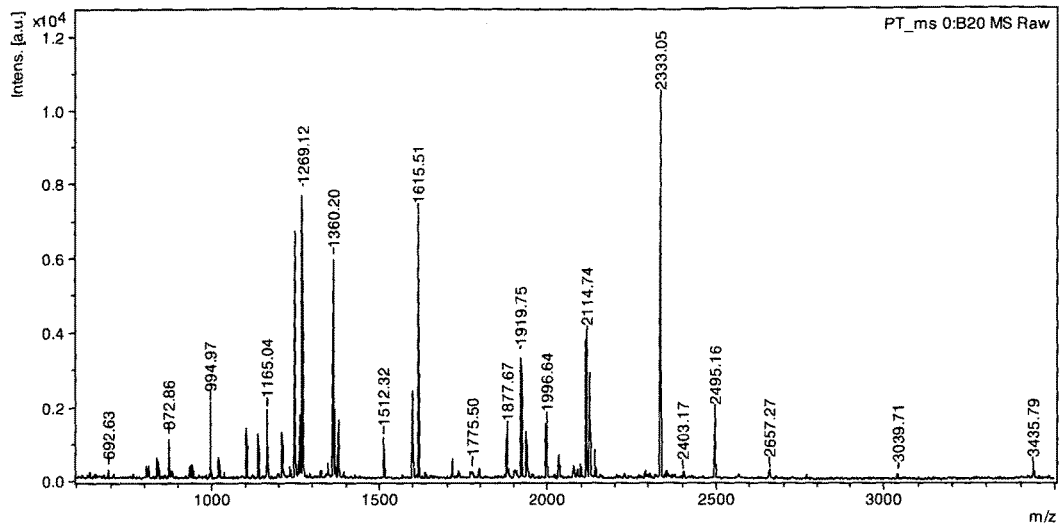
FIG. 9C. MALDI-TOF MS spectrum of the peptide mixture resulting from tryptic digestion of PT. HCCA was used as a matrix. Signals observed in the spectrum correspond to peptides derived from the subunits (S1-S5) such as: $^{122}$MFLGPK$^{127}$ (SEQ ID NO: 1)m/z 692,63-S4; $^{56}$ALTVAELR$^{63}$ (SEQ ID NO:2) m/z 872,86-S2; $^{169}$RIPPENIR$^{176}$ (SEQ ID NO:3) m/z 994,97-S1; $^{217}$SVASIVGTLVR$^{227}$ (SEQ ID NO:4) m/z 1102,09-S1; $^{64}$GSGDLQEYLR$^{73}$ (SEQ ID NO:5) m/z 1137,99-S1; $^{65}$GNAELQTYLR$^{74}$ (SEQ ID NO:6) m/z 1165,04-S3; $^{93}$YTEVYLEHR$^{101}$ (SEQ ID NO:7) m/z 1210,05-S1; AVFMQQRPLR$^{121}$ (SEQ ID NO:8) m/z 1246,16-S4; $^{39}$ALFTQQGGAYGR$^{50}$ (SEQ ID NO:9) m/z 1269,12-S3; $^{100}$RPGSSPMEVMLR$^{111}$ (SEQ ID NO:10) m/z 1360,20-S4; $^{92}$RYTEVYLEHR$^{101}$ (SEQ ID NO:11) m/z 1366,20-S1; $^{114}$GTGHFIGYIYEVR$^{126}$ (SEQ ID NO:12) m/z 1512,32-S1; $^{128}$QLTFEGKPALELIR$^{141}$(SEQ ID NO:13) m/z 1615,51-S4; K$^{79}$LGAAASSPDAHVPFCFGK$^{96}$ (SEQ ID NO:14) m/z 1775,50-S4; 1877,67-S1; 919,75-S3; $^{120}$NTGQPATDHYYSNVTATR$^{137}$ (SEQ ID NO:15 )m/z 1996,64-S2; $^{181}$VYHNGITGETTTTEYSNAR$^{199}$ (SEQ ID NO:16 ) m/z 2114,75-S1; K$^{51}$TNMVVTSVAMKPYEVTPTR$^{69}$ (SEQ ID NO:17) m/z 2124,74-S4; $^{28}$STPGIVIPPQEQITQHGGPYGR$^{49}$ (SEQ ID NO:18) m/z 2333,05-S2; $^{44}$YDSRPPEDVFQNGFTAWGNN DNVLDHLTGR$^{73}$ (SEQ ID NO:19) m/z 3435, 79-S1.
Figure 9D:
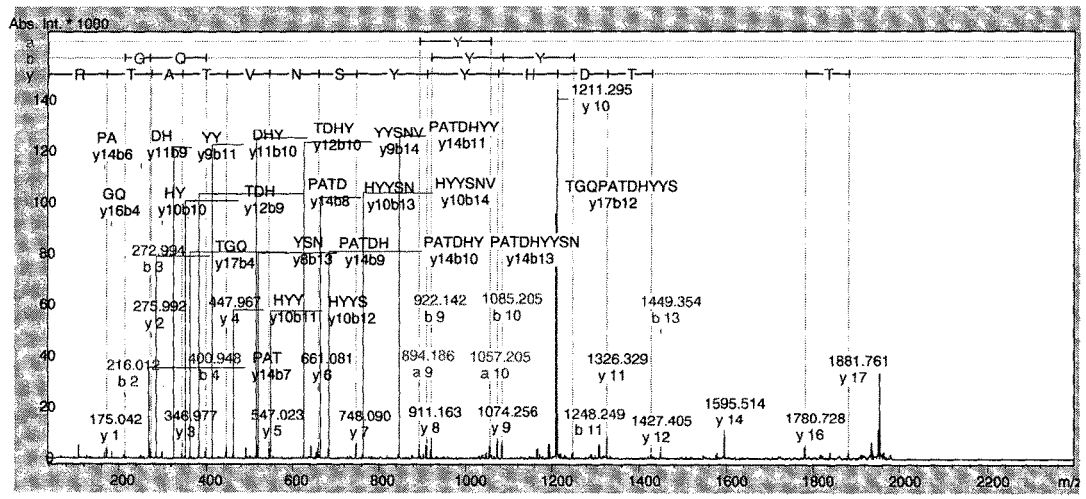

FIG. 9D. The laser-induced dissociation (LID) employed for the identification of the PT peptide sequences. For example, a sequence: R.NTGQPATDHYYSNVTATR, (SEQ ID NO:20) m/z 1996.641 was identified and corresponds to the amino acid fragment (120-137 position) of S2 subunit.

Figure 9E:
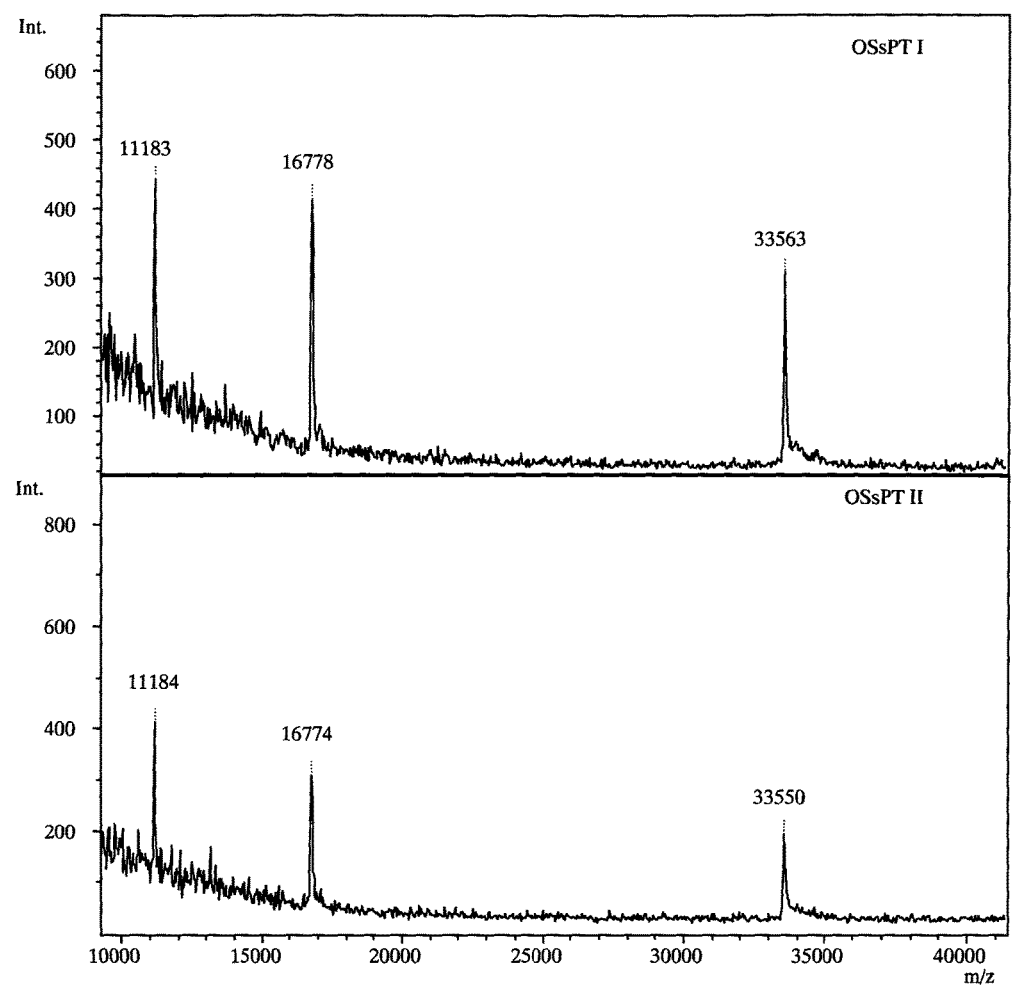

FIG. 9E. MALDI-TOF MS spectrum of the OS-PT. MALDI-TOF MS spectra of the OS-PT with varying OS content, 49% and 30% (OS-PT I and II, respectively). Spectra of both the OS-PT, showed identical signals. The differences between the OS-PT spectra and the PT spectra indicate that the PT subunits were modified by the conjugation with OS.

Figure 9F:
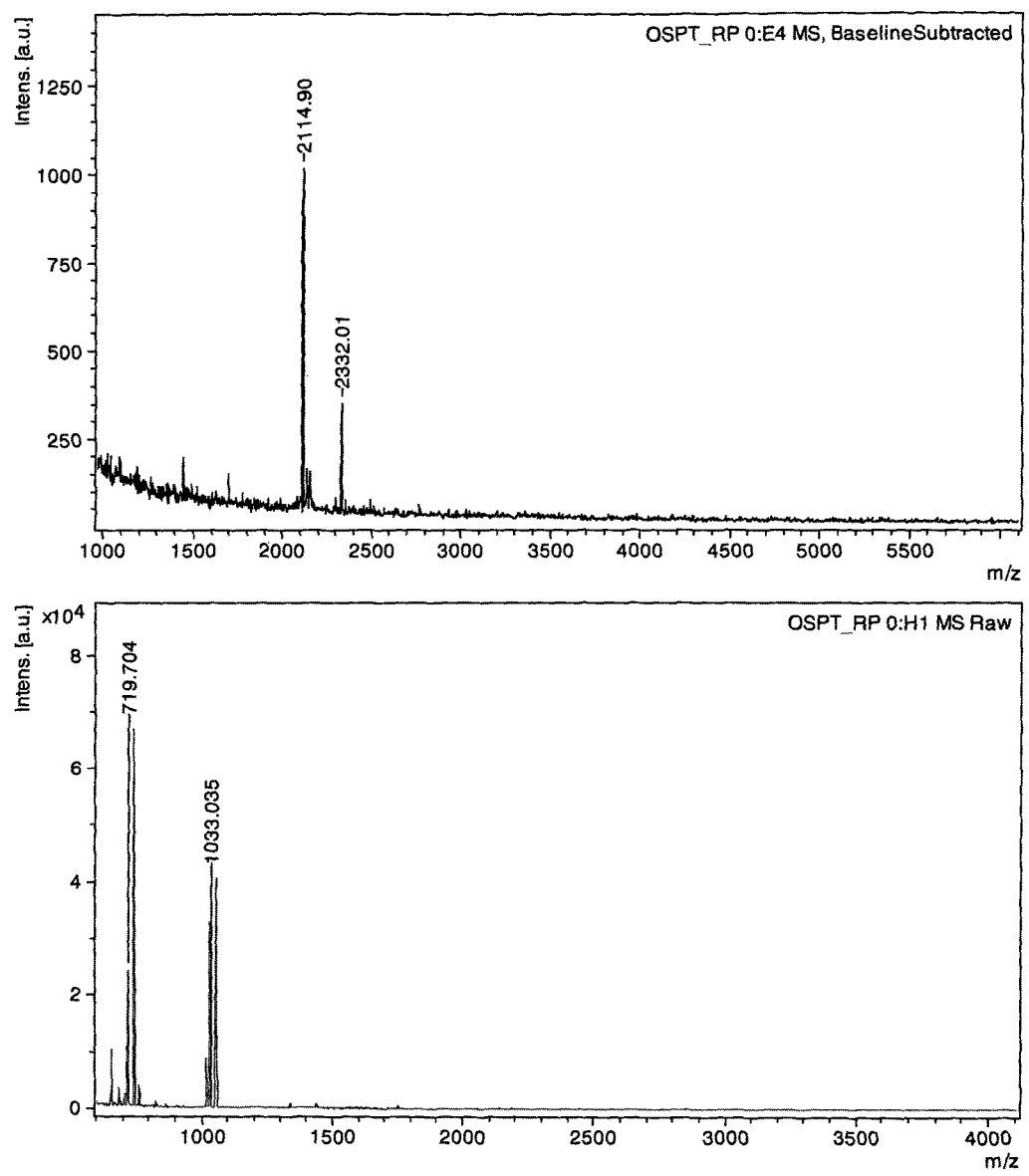

FIG. 9F. MALDI-TOF MS spectra of the peptides obtained from a tryptic digestion of the OS-PT. The observed signals, at m/z 2114.90, 2332.01 and 1033.04 represent the unmodified PT peptides present in the S1 and S2 subunits. Additionally, the sequences of VYHNGITGETTTTEYSNAR (SEQ ID NO:21) for ion at m/z 2113.902 and YVSQQTR (SEQ ID NO: 22) for ion at m/z 881.4620 were identified in the OS-PT, meaning that these peptides have not been modified during conjugation of PT. The peptides were separated on $C_{18}$ column.

FIG. 9G. Table of m/z values for signals, which were observed in the MALDI-TOF MS spectra of peptides generated by the tryptic digestion of PT and the OS-PT. The peptides containing a lysine (K) are potential sites of the OS attachment. Lack of such signals in the spectra of the OS-PT and their presence in the spectra of the PT suggests that they contain the lysine residues substituted by an oligosaccharide. Lysine residues in peptides that are potential sites of substitution by the OS are designated in the table as a potential glycosylation sites. The potential glycosylation sites are lysine residues numbered in the sequence of subunits as follows: S2-110 and 178; S3-38 and 133; S4-61 and 96; S5-52 Potential glycosylation sites may also include lysine residues at position 121 in the S3 subunit and at positions 50, 78 and 99 in the S4 subunit since the signals were not observed, neither in the spectra of the OS-PT nor in the spectra of PT. The lack of the peptide signals may result from their instability during the measurement or their poor ionization at the applied measurement conditions, while using MALDI-TOF MS.

Figure 10A:
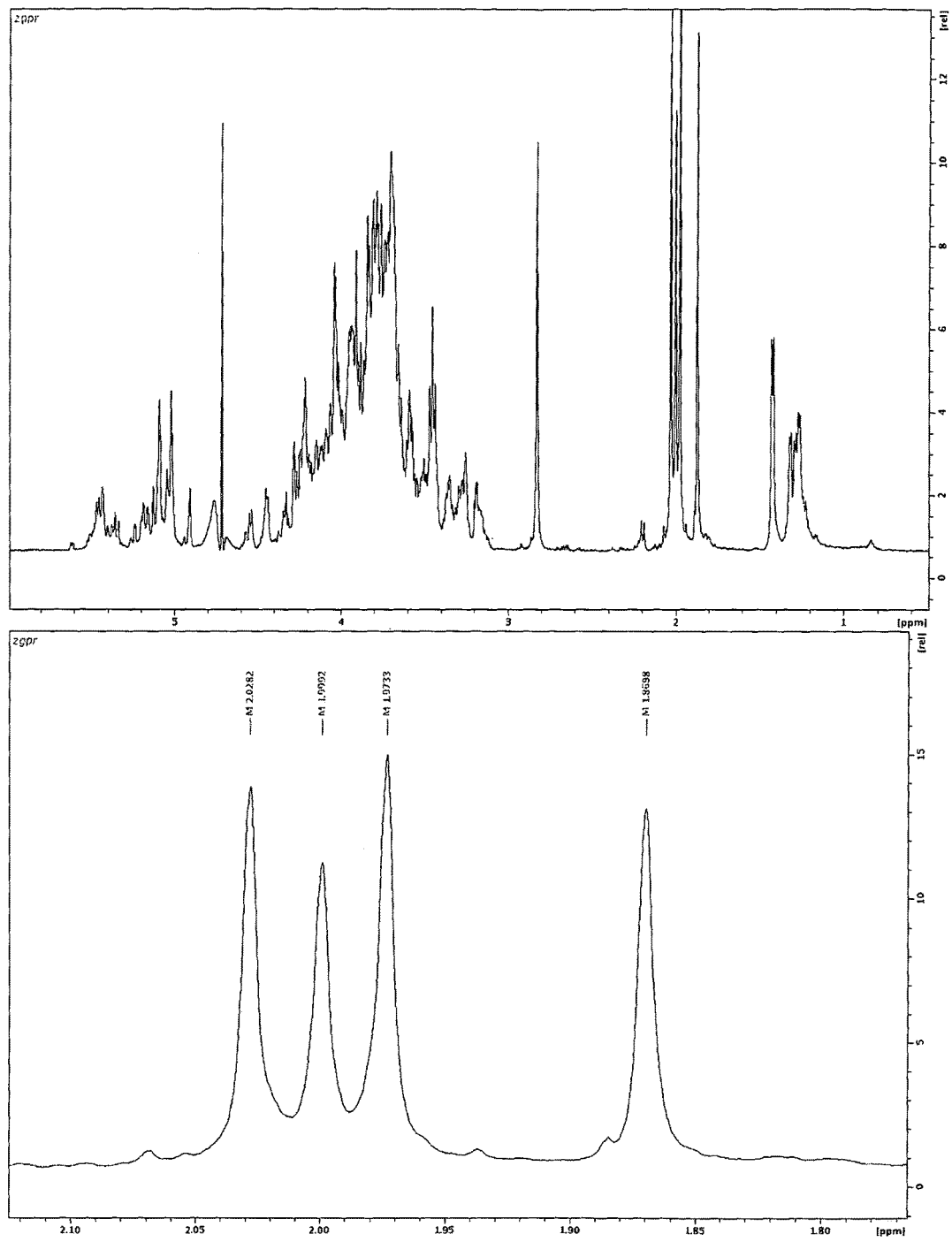
Figure 10B:
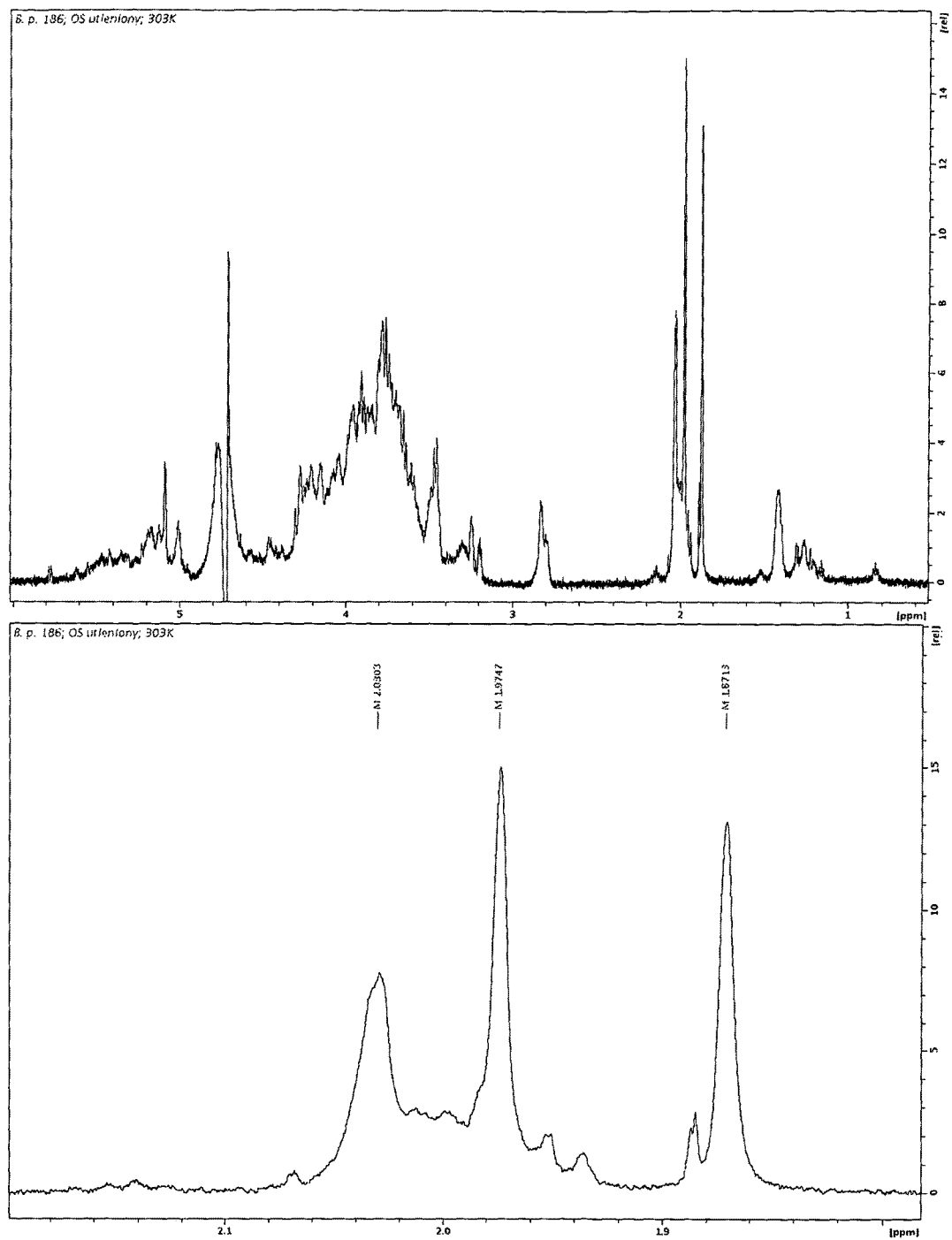

FIGS. 10A and 10B. NMR spectra of *B. pertussis* 186 oligosaccharides.

FIG. 10A. $^1$H NMR spectrum of *B. pertussis* 186 oligosaccharide.

FIG. 10B. $^1$H NMR spectrum of the *B. pertussis* 186 oxidized oligosaccharide.

Figure 11B:
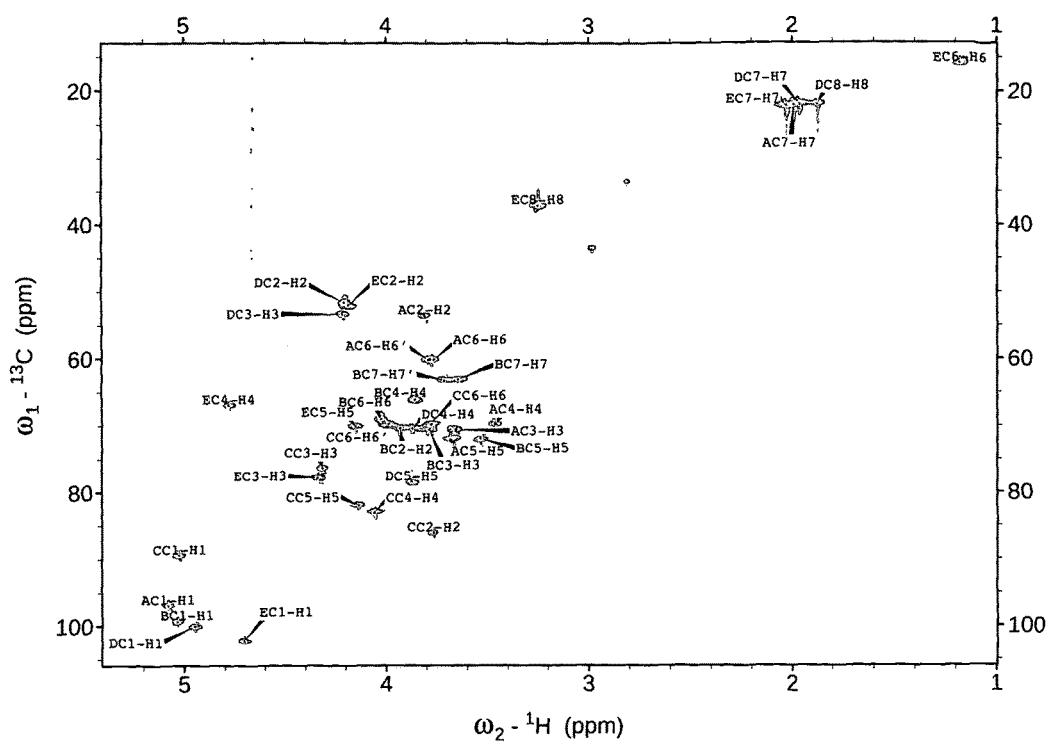
Figure 11C:
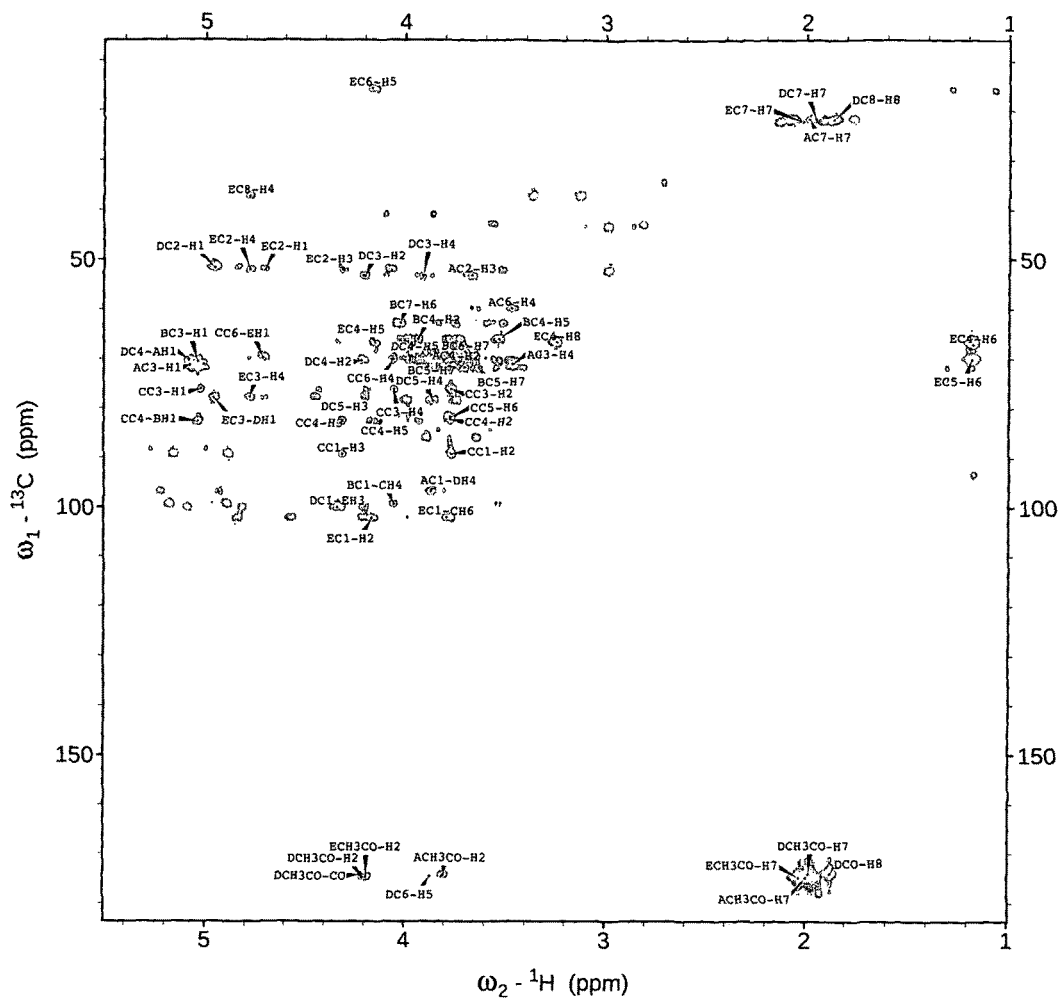

FIG. 11. 2D NMR spectra of the pentasaccharide derived from *B. pertussis* 186 LOS. COSY (A), HSQC (B), HMBC (C) spectra were obtained. The chemical shift data (D) of the spectra were summarized in a table. Sugars residues in the pentasaccharide are designated by the letters A through E as depicted on the enclosed drawing.

Figure 12A:
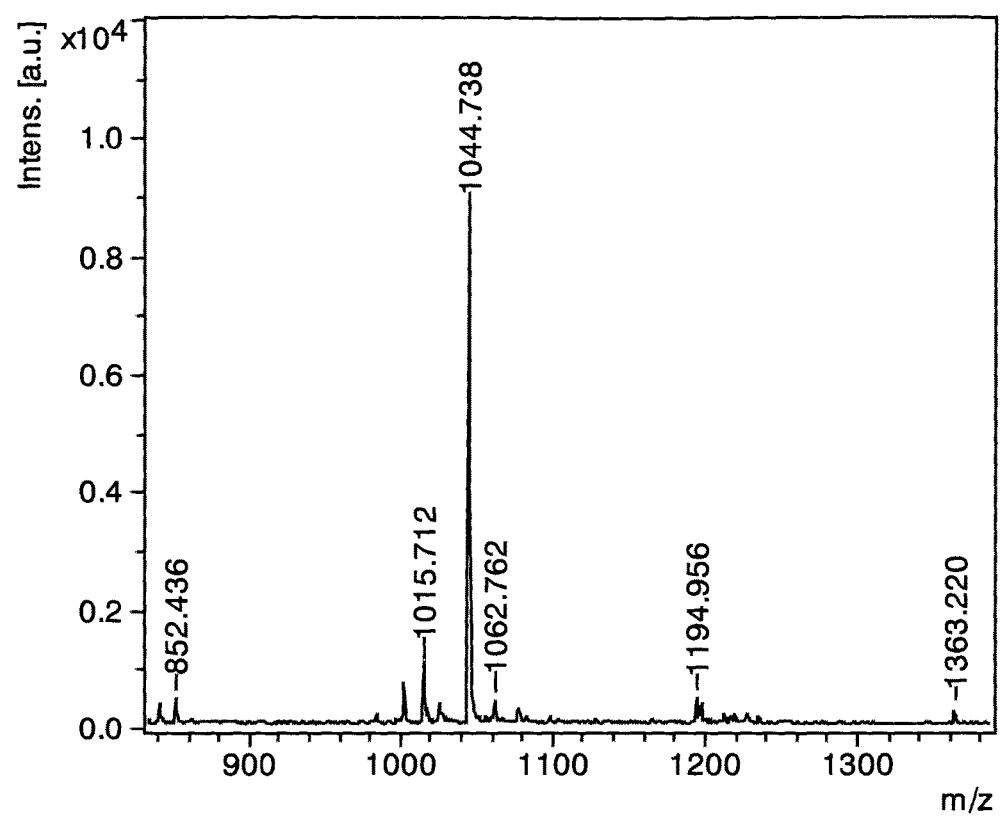
Figure 12B:
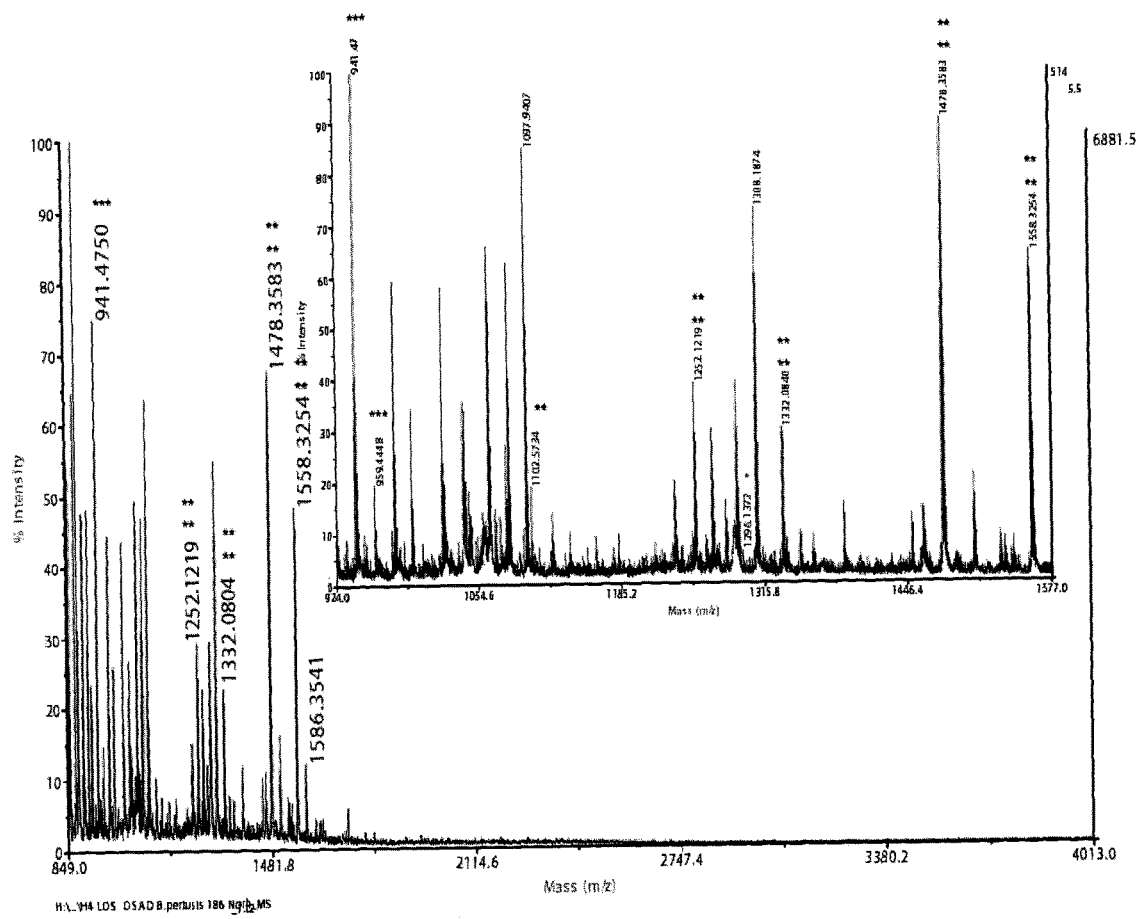

FIGS. 12A and 12B. MALDI-TOF MS spectra of the LOS deamination products.

FIG. 12A. MALDI-TOF MS of the pentasaccharide isolated from B. pertussis 186 LOS. Spectrum was recorded in negative-ion mode on Ultraflex spectrometer, Bruker Daltonics. Trihydroxyacetophenon (25 mg/ml) was used as a matrix.

FIG. 12B. MALDI-TOF MS spectrum of the LOS deamination products separated from the pentasaccharide. A core fragment devoid of the terminal pentasaccharide and galactosaminuronic acid with a mass of 1121.35 in a dehydrated form was identified as an ion at m/z 1102.5734 (). An oligosaccharide fragment obtained after cleavage of the terminal pentasaccharide, galactosaminuronic acid and glucosamine, with a monoisotopic mass of 960.28, corresponds to the ion at m/z 959.4448 and its dehydrated form at m/z 941.4750 (*). The ions at m/z 1558.32, 1478.35, 1332.08, 1252.12 (****) represent the lipid A.

The invention was illustrated by the following embodiment.

EXAMPLES

A. The Culture of B. Pertussis

B. pertussis 186 was grown in Stainer-Scholte liquid medium with an addition of (2,6-di-O-methyl)-β-cyclodextrin. The growth was controlled by biotyping using MALDI-TOF MS and MALDI Biotyper method (MBT). Spectral analysis was performed in positive-ion mode giving the protein spectra and in negative-ion mode to obtain profiles of endotoxin (FIG. 3 A, according to P. 400598 and WO2014035270A1). On the basis of the characteristic MALDI-TOF MS protein profile, *B. pertussis* 186 grown in the solid and liquid media has been identified as *Bordetella pertussis* DSM 4925 in the reference MALDI Biotyper database. The *B. pertussis* 186 strain used in this invention is a vaccine-type strain used for immunization of children in Poland.

B. Isolation of a Pertussis Toxin

The pertussis toxin, used as a component of the glycoconjugate in this invention was prepared by isolation from the culture media of *B. pertussis* 186 using an ion-exchange chromatography method (Method 1) [49, 66]. The method was modified in its final step, by using a buffer with 50% glycerol content during dialysis. The addition of glycerol proved to be necessary to isolate the PT. Briefly, the method employs the CM-Sepharose CL-6B used as a cation-exchange resin. The separation is achieved through the binding of two proteins from *B. pertussis* 186 culture, PT and FHA to the resin and their subsequent elution as separate fractions by changing the pH and ionic strength. The isolation of PT was monitored by UV-absorbance measurement (FIG. 1). In recorded chromatogram, the first fraction with retention time of 245 minutes corresponds to the PT, and the second fraction with retention time of 335 minutes corresponds to FHA. Fractions containing PT reacted with anti-pertussis toxin antibody in immunoblotting. A culture (3.5 liters) of *B. pertussis* 186 yielded 4.26 mg of PT. The PT fractions in a phosphate buffer containing 0.5 M NaCl and 50% glycerol were stored at −75° C.

C. Isolation of *B. Pertussis* 186 Oligosaccharide

LOS was isolated from *B. pertussis* 186 by water-phenol extraction according to a method of Westphal et al. Then, an oligosaccharide (OS) was isolated from the LOS by acid hydrolysis (1.5% acetic acid). The OS was purified by removing a lipid A during ultracentrifugation (105000×g, 2 h, 4° C.). MALDI-TOF mass spectrometry was used to confirm that the structures of the isolated LOS (FIG. 3B) and OS are identical as the structures of LOS and the OS present on the surface of *B. pertussis* (FIG. 3A). Prior to conjugation with PT, the oligosaccharide was oxidized using sodium periodate (Method 2). The product of the reaction was purified by gel filtration, yielding the oxidized OS fractions (retention time of 16.8 and 20.5 min) separated from a fraction contaminated with a lipid A (retention time of 13 min) and a fraction containing the OS devoid of heptose residue (retention time of 21.5 min; FIG. 2). The composition of the fractions was determined by MALDI-TOF MS analysis (FIG. 3 F). The fraction containing the oxidized OS was used for conjugation.

D. Analysis of *B. Pertussis* 186 LOS and OS by MALDI-TOF Mass Spectrometry

The obtained preparations of *B. pertussis* 186 bacteria and the isolated LOS and OS were analyzed by MALDI-TOF MS (FIG. 3 A-E). These analyses confirmed that the structures of the LOS and the OS were identical with the structures of the LOS and the OS on the surface of *B. pertussis* cell. Therefore, the methods used for the OS isolation allow to preserve the epitopes exposed on the surface of *B. pertussis*.

The signals in the mass range of m/z 2200-2600 correspond to the core oligosaccharide of the *B. pertussis* LPS (FIG. 3 B) [10]. The ions correspond to the dodecasaccharide (m/z 2291.63) and its pyrophosphorylated and pyrophosphorylethanolamine forms (m/z 2452.57 and 2497.13). A signal with the highest intensity of ion at m/z 2231.43 indicates a neutral molecule loss of $CO_2$ (−44 Da) and two molecules of water from dodecasaccharide with a calculated molecular weight of 2312.337 Da. A few glycoforms devoid of the terminal heptose are also identified among ion groups at m/z 2039 and 2231, 2082 and 2274, 2260 and 2452 (FIG. 3 C). The spectrum of the isolated LOS also reveals signals in a lower mass range which correspond to a lipid A (m/z 1558.95) and in a higher mass range which originate from a complete lipooligosacccharide (m/z 4056.65). Molecular ions corresponding to an oligosaccharide and the lipid A observed in the spectrum of the isolated LOS were also found in the spectrum of *B. pertussis* whole cells (FIG. 3 A). The main ions observed in the spectrum of *B. pertussis* 186 represent a dodecasaccharide devoid of neutral $CO_2$ molecule and two molecules of water (m/z 2230.23), anhydrododecasaccharide (m/z 2294.32); anhydrododecasaccharide substituted with a pyrophosphate group (m/z 2451.55) and the lipid A (m/z 1558.63).

MALDI-TOF MS spectrum of *B. pertussis* oligosaccharide isolated and purified on Dowex $H^+$ resin was recorded in positive-ion mode. A molecular ion at m/z 2312.4 corresponded to the dodecasaccharide (FIG. 3 D). The spectrum of the OS indicates a loss of phosphate residues during acid hydrolysis of LOS but with the structure of the remaining sugars preserved. The changes in the OS ionization could be attributed to a probable loss of the phosphate groups, however the structure of the isolated OS was identical with the structure of sugar part of the isolated LOS and the LOS exposed on the surface of *B. pertussis* 186 cells (FIG. 3 E, interpretation of the signals).

In the spectrum of the oxidized OS, a mass shift of 30 Da towards the lower mass range was observed in comparison with the signal of the OS (FIG. 3 F). The signal of m/z 2279.49 in the spectrum of the oxidized OS indicates the loss of a HCHO fragment from the Kdo residue of oligosaccharide molecule treated with 0.01 M sodium periodate.

Under this conditions, a bond between two adjacent carbon atoms substituted by hydroxyl groups in a side group of Kdo of the oligosaccharide was cleaved and the reactive aldehyde group was formed. Furthermore, it is capable of reacting with an amine group of a protein (Scheme 2):

Scheme 2. Preparing of OS—PT conjugate by reductive amination.

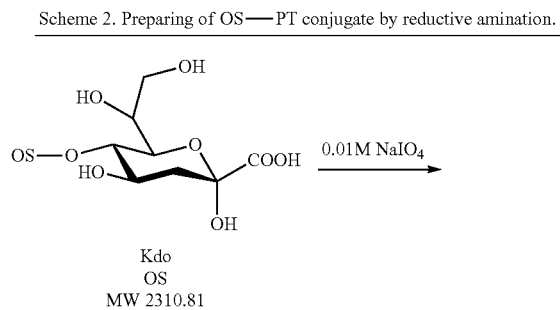

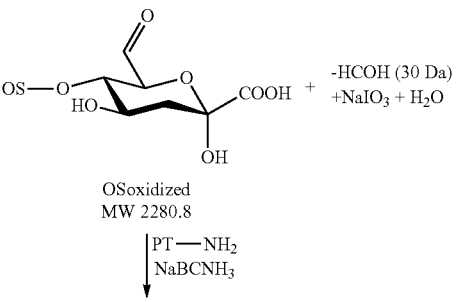

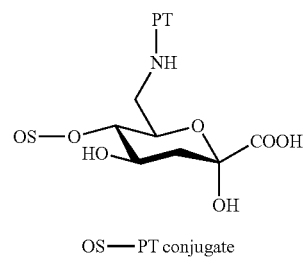

OS—PT conjugate

In addition, in MALDI-TOF MS spectrum of the oxidized OS, the ion at m/z 1337.79 was observed (FIG. 3 G), which can be attributed to the structure of the oxidized OS devoid of HexNAc, Hep, HexN, HexA, HexNA residues and two water molecules. Vicinal hydroxyl groups in these sugar moieties are susceptible to periodate oxidation leading to their cleavage [6, 78]. During treatment of the OS with periodate, the sugar residues (indicated by arrows) may be oxidized and a heptasaccharide can be obtained as depicted on Scheme 3:

Scheme 3. Preparation of the heptasaccharide

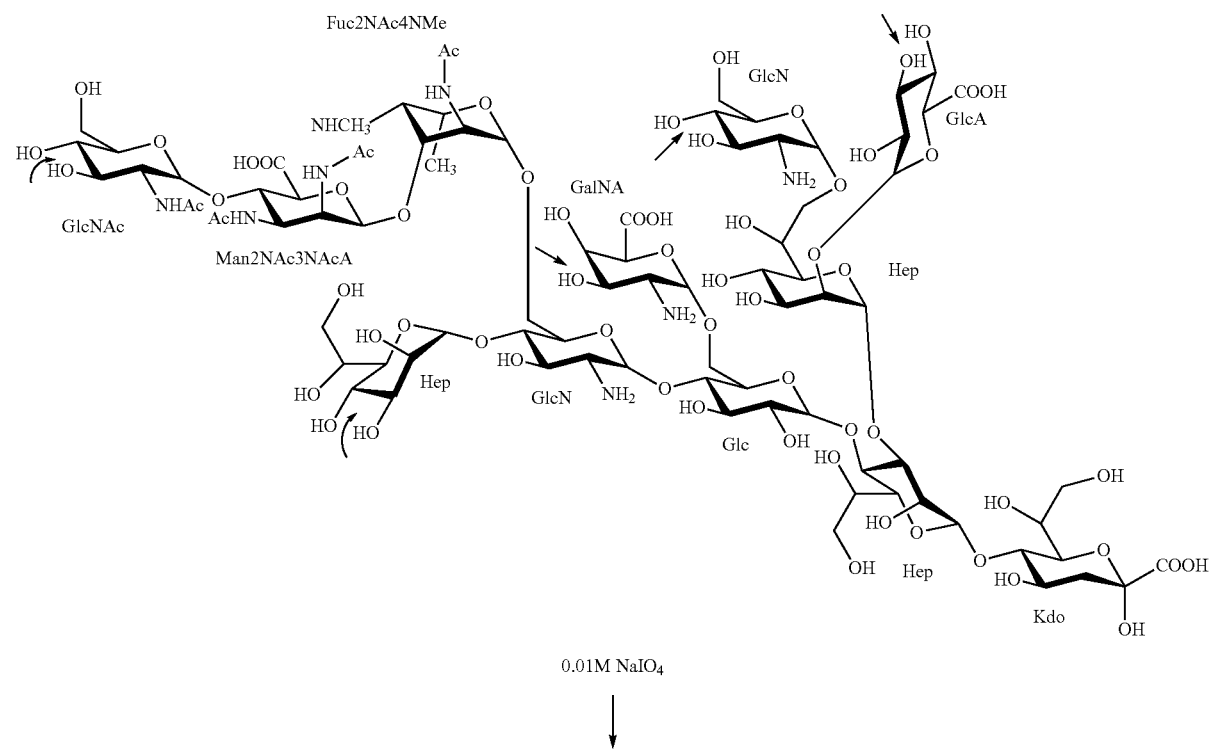

-continued

[Chemical structure diagram showing oligosaccharide with labeled residues: Fuc2NAc4NMe, Man2NAc3NAcA, GlcN, Glc, Hep, Kdo]

Periodate oxidation of B. pertussis 186 OS leads to a heterogeneous mixture of oligosaccharides differing in the number of sugar residues.

The activated OS was used for conjugation with pertussis toxin.

E. Preparation of OS-PT Conjugate

The oxidized oligosaccharide of B. pertussis 186 was used for conjugation with pertussis toxin by reductive amination (Method 2). The oxidized oligosaccharide (20 mg) and PT (1 mg) were used for conjugation. The reaction was performed in a borate buffer at pH 9.0.

Figure 1:
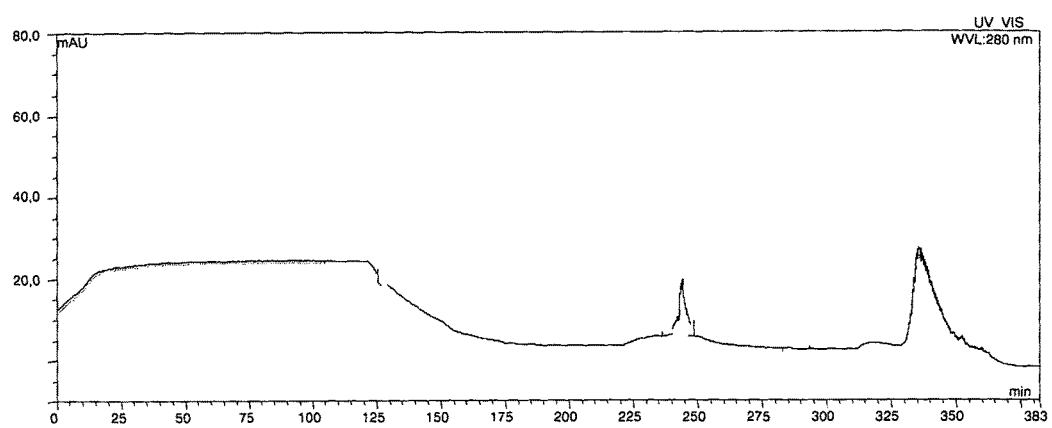
FIG. 1. Isolation of PT using CM-Sepharose. Fraction I, retention time of 245 minutes, corresponds to PT and fraction II, retention time of 335 minutes, corresponds to FHA.
Figure 2:
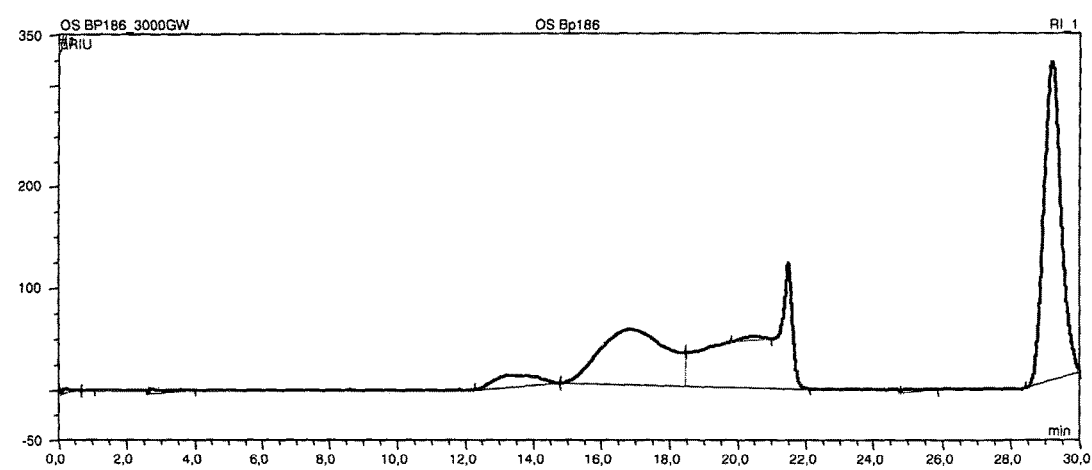
FIG. 2. Isolation of the oxidized OS using a gel filtration, G3000-PW. The flow conditions were: 6 ml/min, $H_2O$. The HPLC fractions at retention times of 16.8 minutes and 20.5 minutes represent the oxidized OS.
Figure 3A:
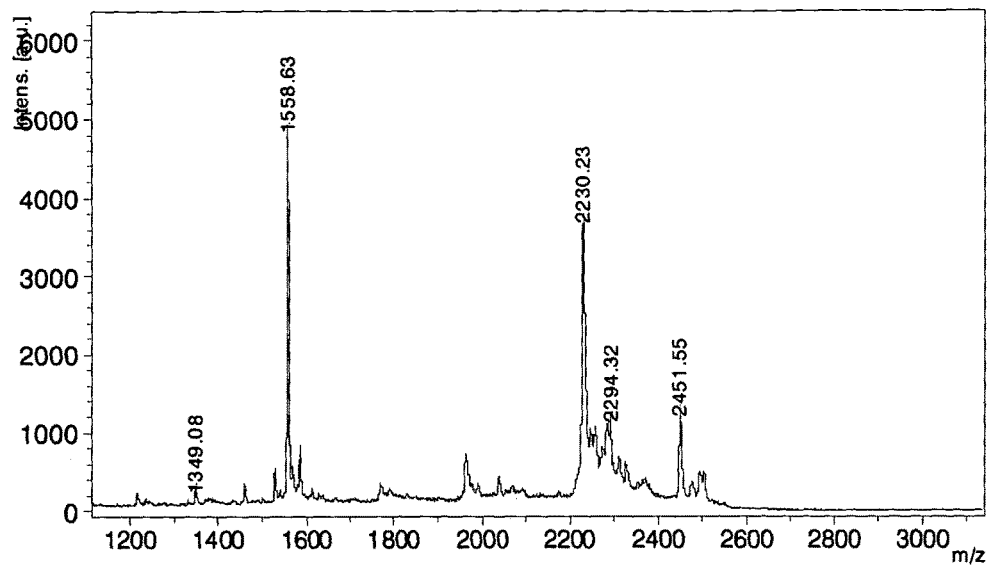
Figure 3B:
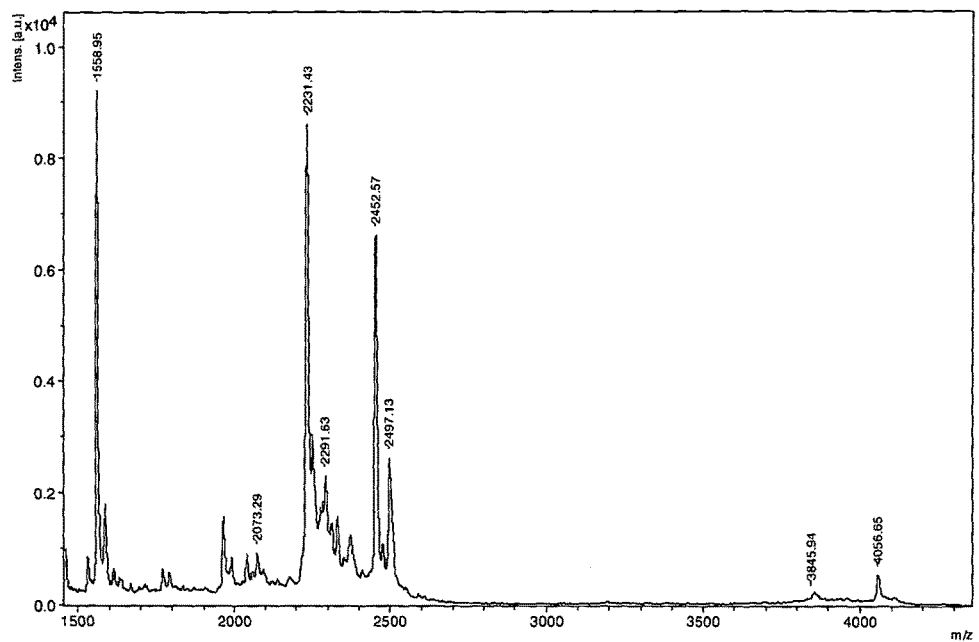
Figure 3C:
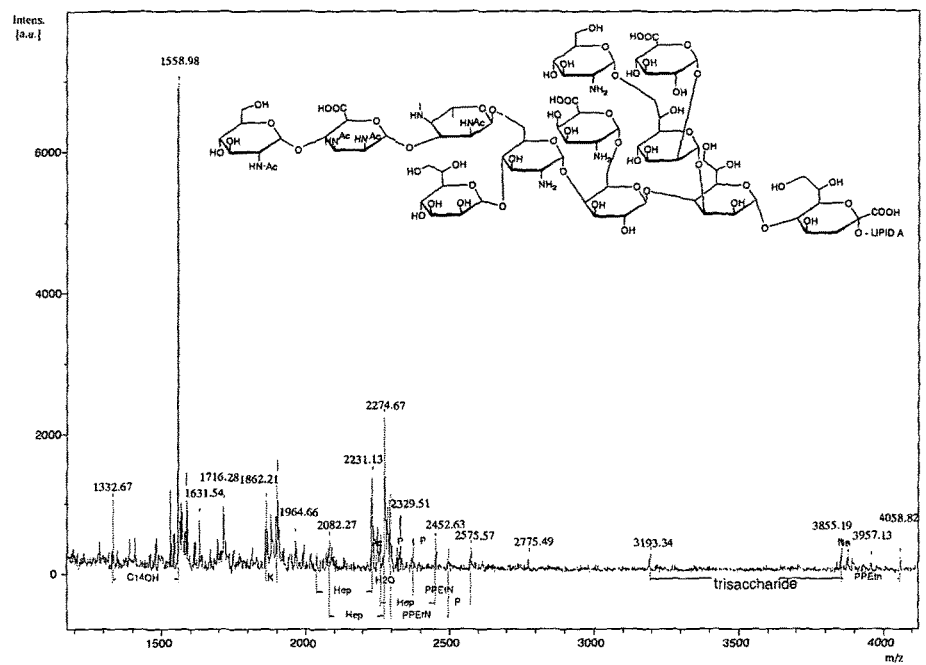
Figure 3D:
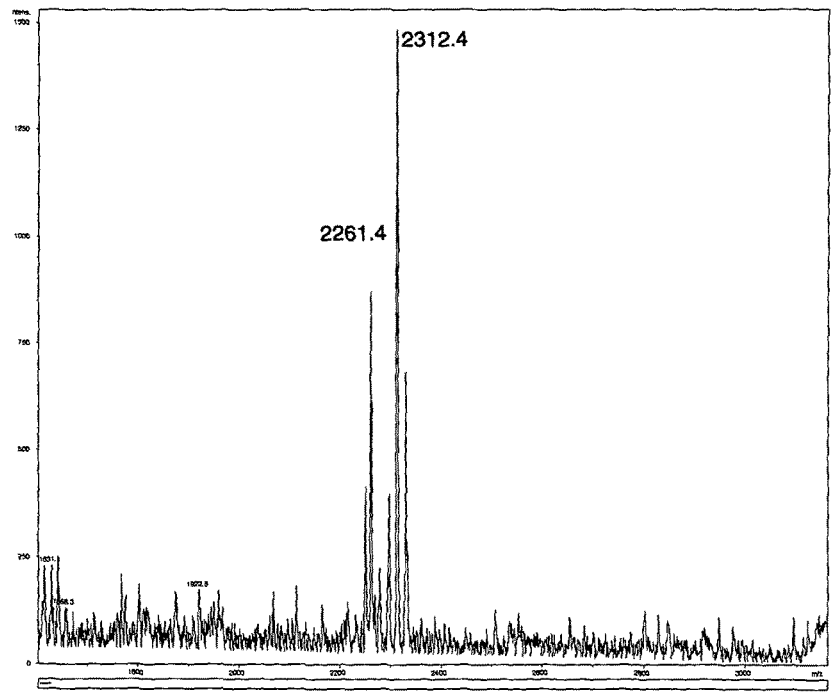
Figure 3F:
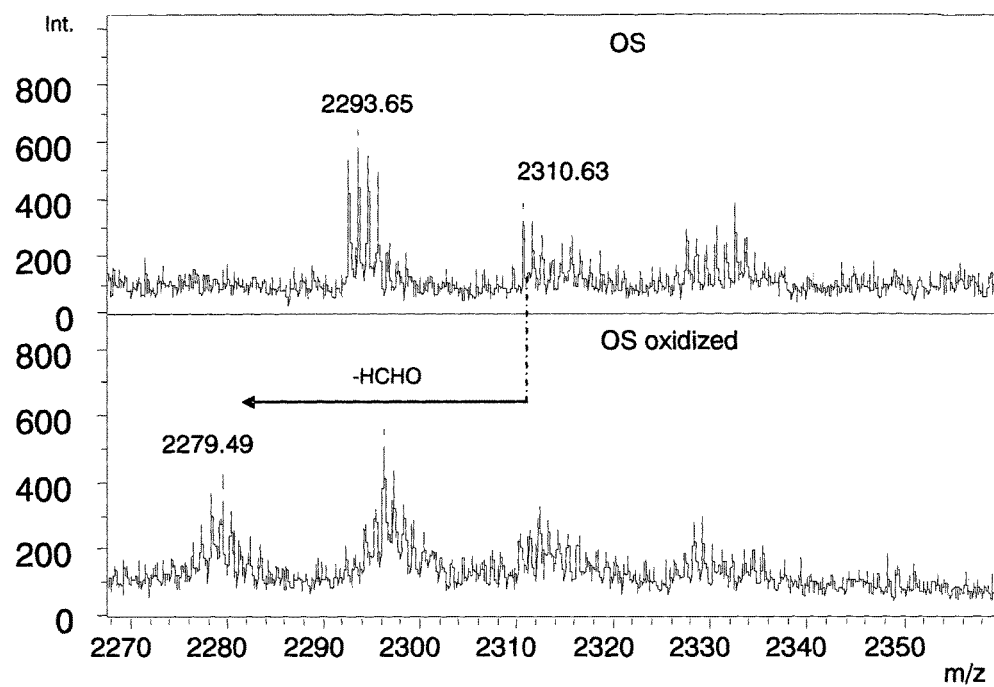
Figure 3G:
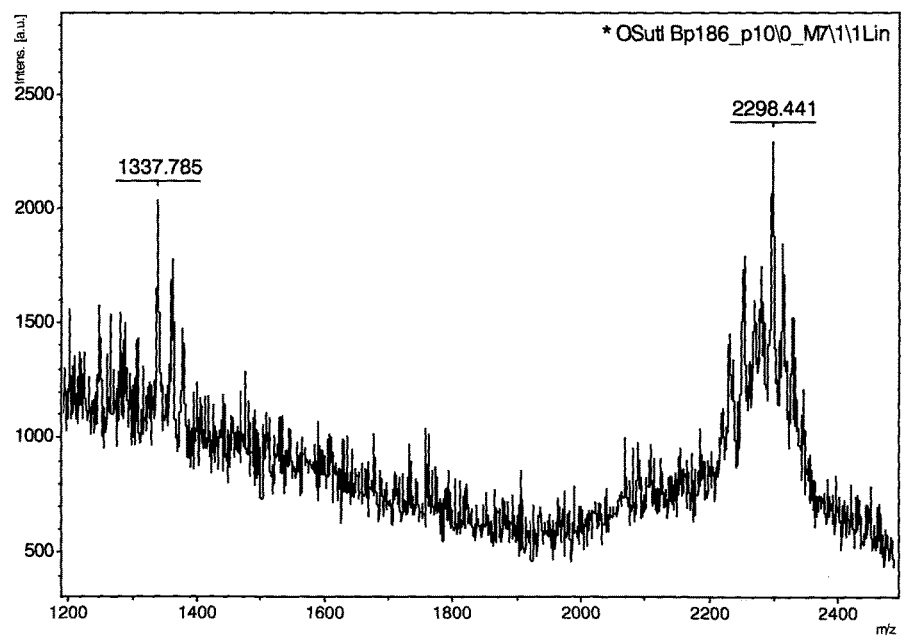
FIG. 3G. MALDI-TOF MS of the oxidized OS recorded in the positive-ion, linear mode. The signal at m/z 2298.4 corresponds to a hydrated form of the oxidized OS. The signal at m/z 1337.8 was tentatively attributed to the oxidized OS devoid of the Hep, HexNAc, HexN, HexA, HexNA residues and two water molecules.
Figure 4:
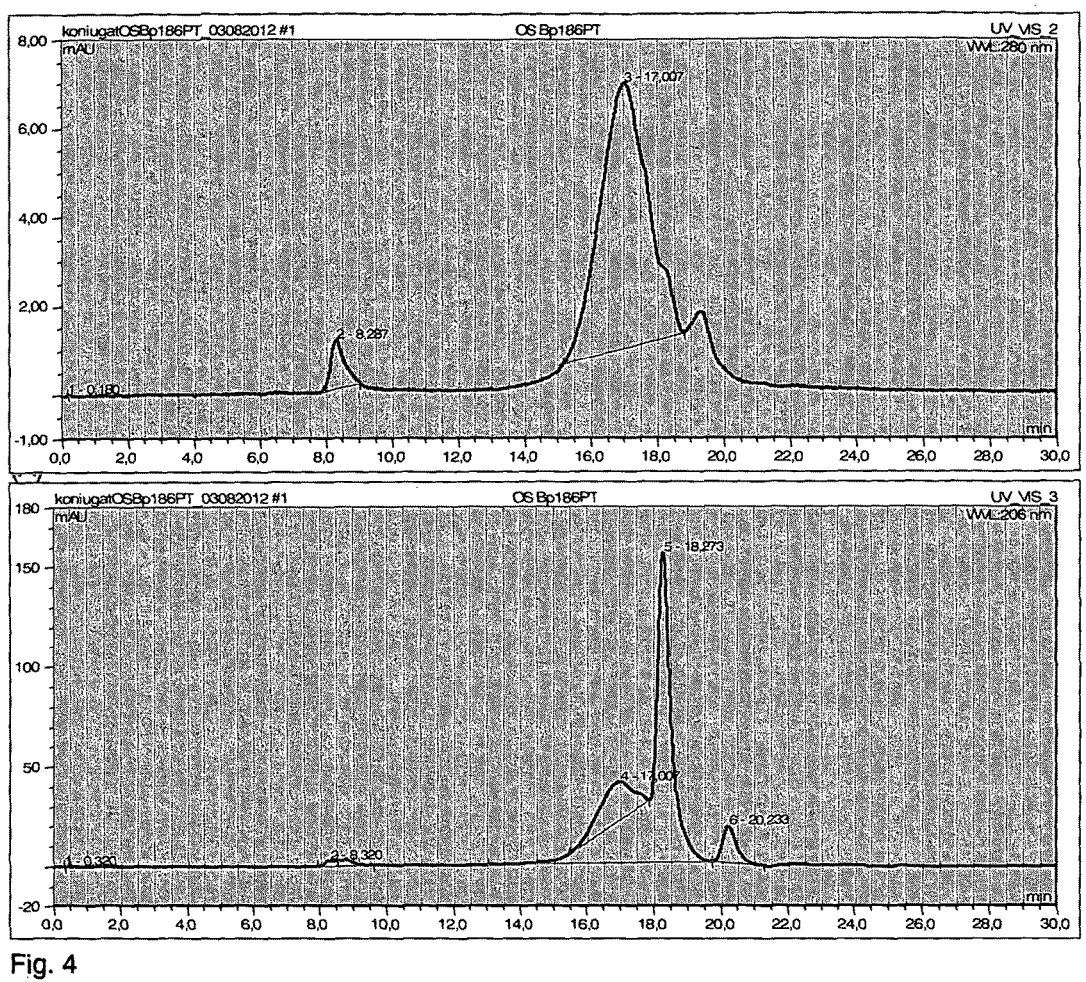
FIG. 4. Isolation of the OS-PT conjugate using gel filtration on G3000-SW column at the flow rate of 6 ml/min, PBS. The measurement was performed at wavelengths: (A) 280 nm and (B) 206 nm. Fraction I (retention time of ~8.3 min) is the OS-PT conjugate with oligosaccharide content of 49%, and the fraction II (retention time of 17 min) with the OS content of 30%. The signal recorded in the spectrum at 206 nm with retention time of 18.3 minutes corresponds to a non-conjugated OS.

The OS-PT conjugate was purified by gel filtration (G3000-SW, FIG. 4). Fractions containing the conjugate were isolated and confirmed in immunoblotting, using specific antibodies, that is antibody directed against B. pertussis 186 LOS-derived pentasaccharide-tetanus toxoid conjugate and an antibody against pertussis toxin. The total ratio of sugar to protein in the conjugate was determined by measurement of protein concentration in combination with the analysis of oligosaccharide content by a phenol-sulfuric acid method.

The OS-PT conjugates, with (1) a protein concentration of 0.37 mg/ml (volume 1.2 ml) and 49% content of oligosaccharide and (2) a protein concentration of 1 mg/ml (volume 0.5 ml) and 30% content of oligosaccharide, were prepared. In the chromatogram, the first fraction with retention time of 8.3 minutes represents the conjugate with maximal content of the OS (49%), while the second fraction with retention time of 17 min corresponds to PT substituted to a lesser extent by OS, approximately 30%. Neither of the obtained glycoconjugates, differing in oligosaccharide content, showed enzymatic activity of the pertussis toxin or retained its binding properties in in vitro test. The glycoconjugate fractions were concentrated and stored at 4° C. with the addition of the preservative (0.01% merthiolate). The OS-PT conjugate with 49% content of the OS and the protein concentration of 0.37 mg/ml was used for immunization of rabbits.

F. Analysis of Biological Activities of PT

Fetuin Binding Assay

Figure 5:
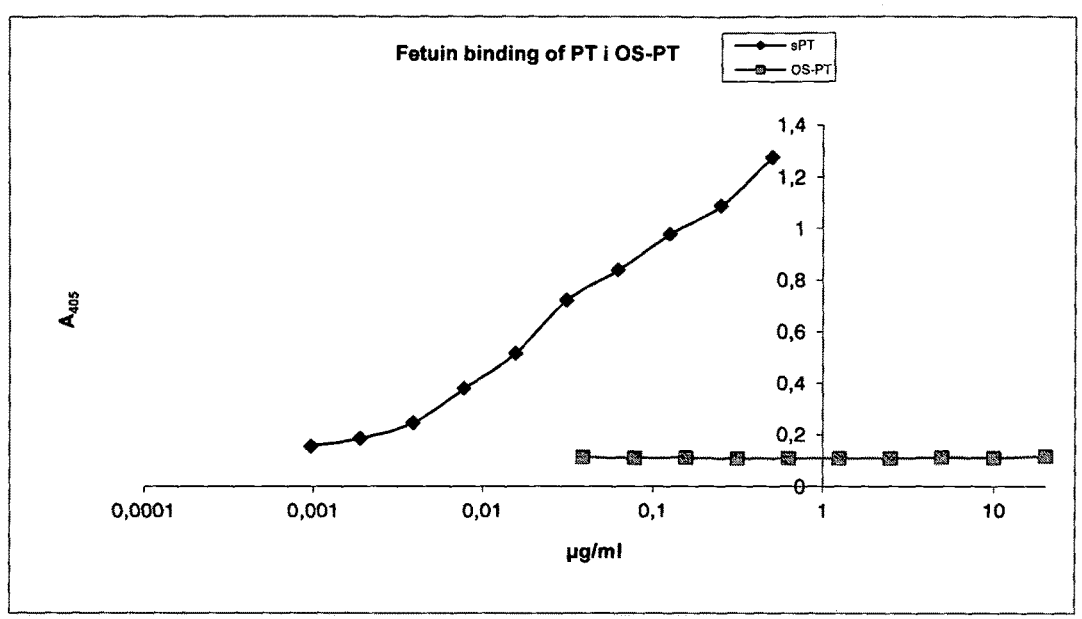
FIG. 5. Fetuin-binding assay of PT and the OS-PT conjugate. The OS-PT was evaluated at concentration of 40-fold higher than that of PT. The absorbance values for the conjugate were lower comparing to these for the lowest concentration of PT.

In the studies of PT, two mechanisms of its biological activity are demonstrated, S1 subunit-dependent activity and the B oligomer-dependent activity. Toxicity of the OS-PT conjugate was examined by reaction with a specific receptor for the toxin that is fetuin (Method 3) [22]. The analysis was performed using the ELISA and an antibody which detects PT associated with fetuin (FIG. 5). The analysis has shown that the OS-PT was not able to bind to fetuin. In the ELISA assay, 20 µg/ml of OS-PT showed an absorbance at $A_{405\ nm}$ 0.117 that was lower than the absorbance for pertussis toxin at the lowest tested concentration (0.97 ng/ml). The analysis indicates the absence of an active toxin in the preparation of the glycoconjugate. The analysis for the OS-PT differing in oligosaccharide contents (30% and 49%) yielded very similar results and indicated inability of the conjugates to bind to fetuin.

G. CHO Cells Assay

The enzymatic activity of PT is observed during an interaction of PT with the CHO cells as a morphological response of the cells [7, 22]. PT induces the CHO cell clustering effect that is inhibited by the presence of anti-PT antibodies used at the neutralizing concentration.

Figure 6A:
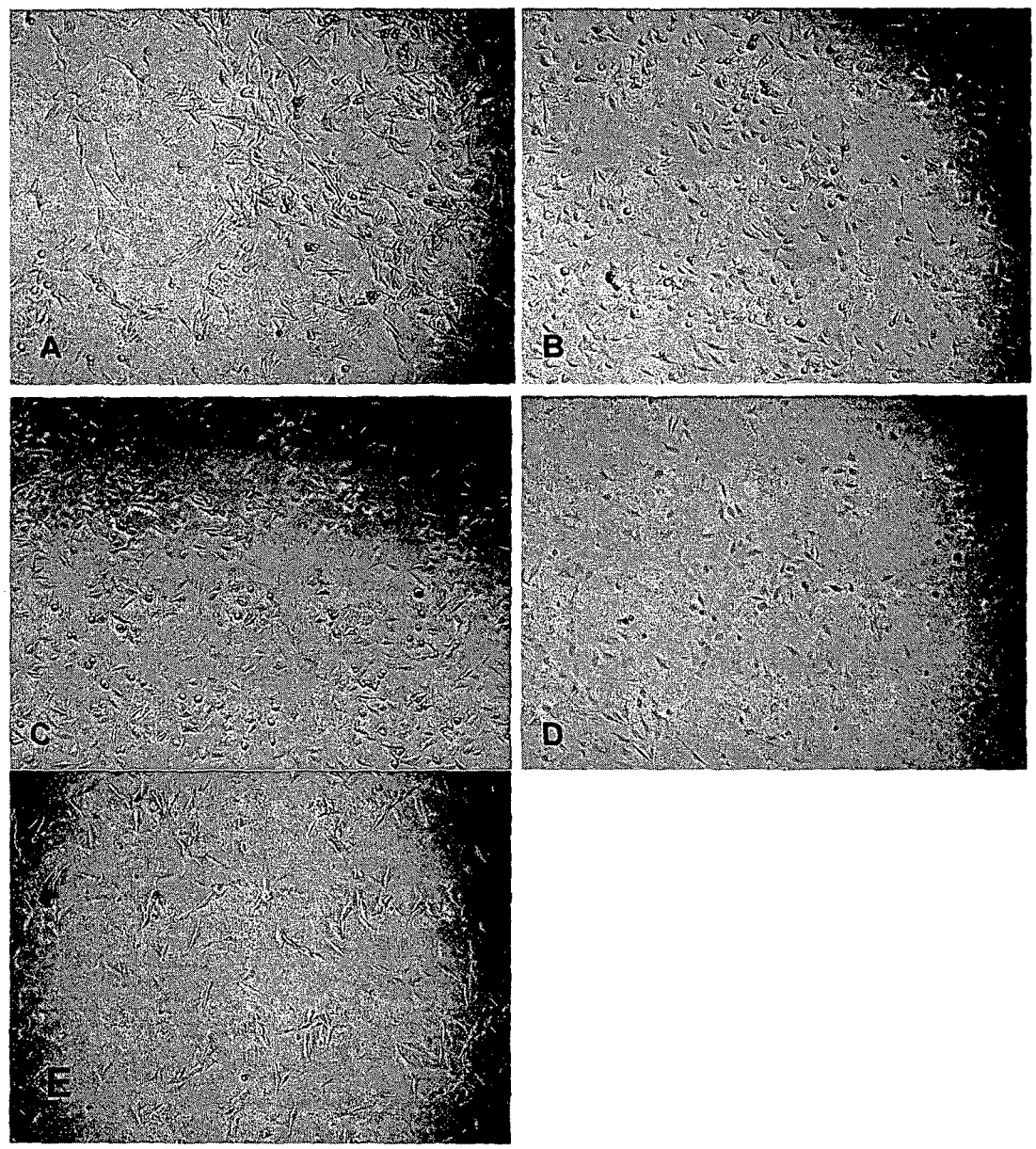
FIGS. 6A and 6B. CHO cells assay for pertussis toxin
Figure 6B:
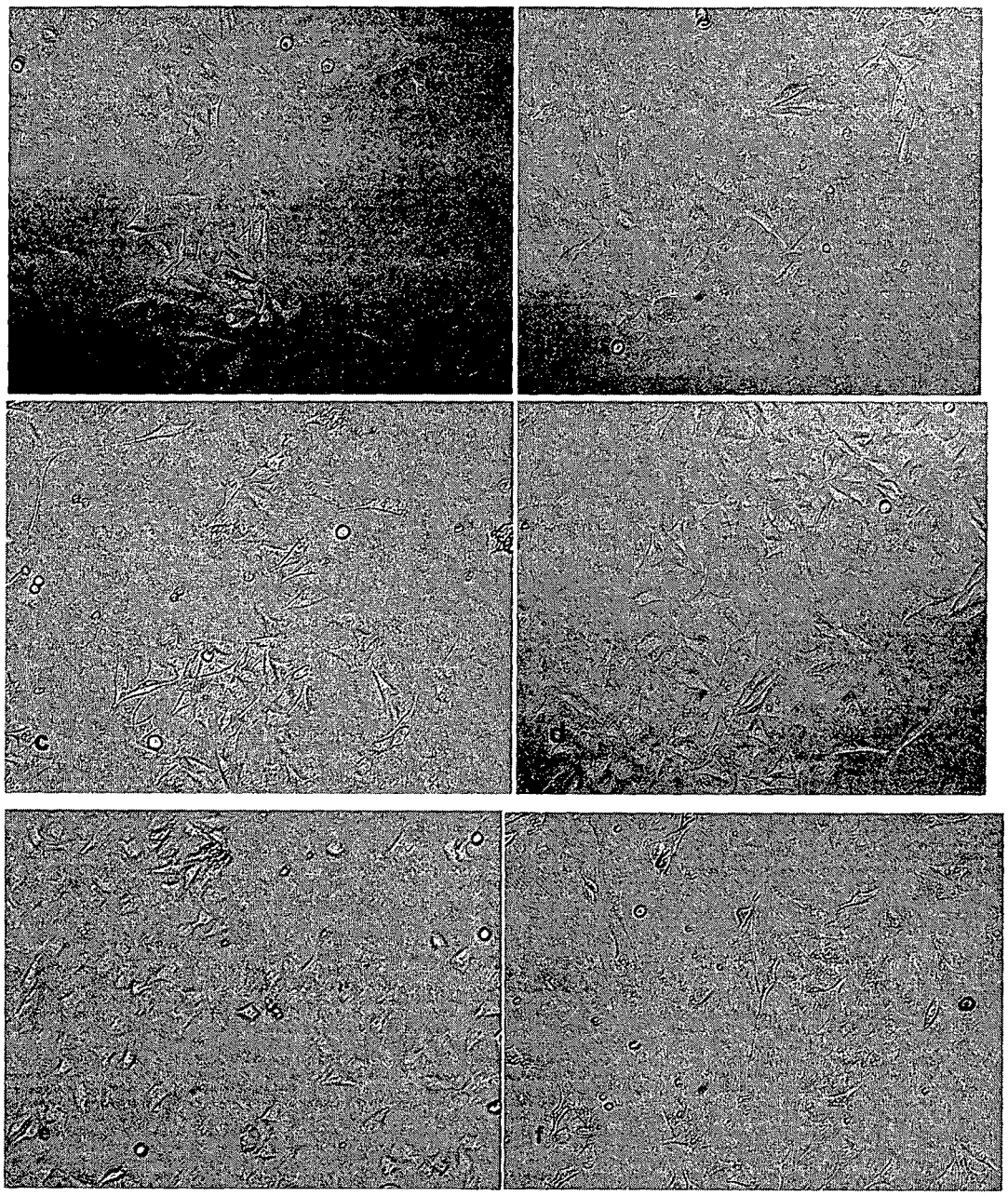
Figure 7:
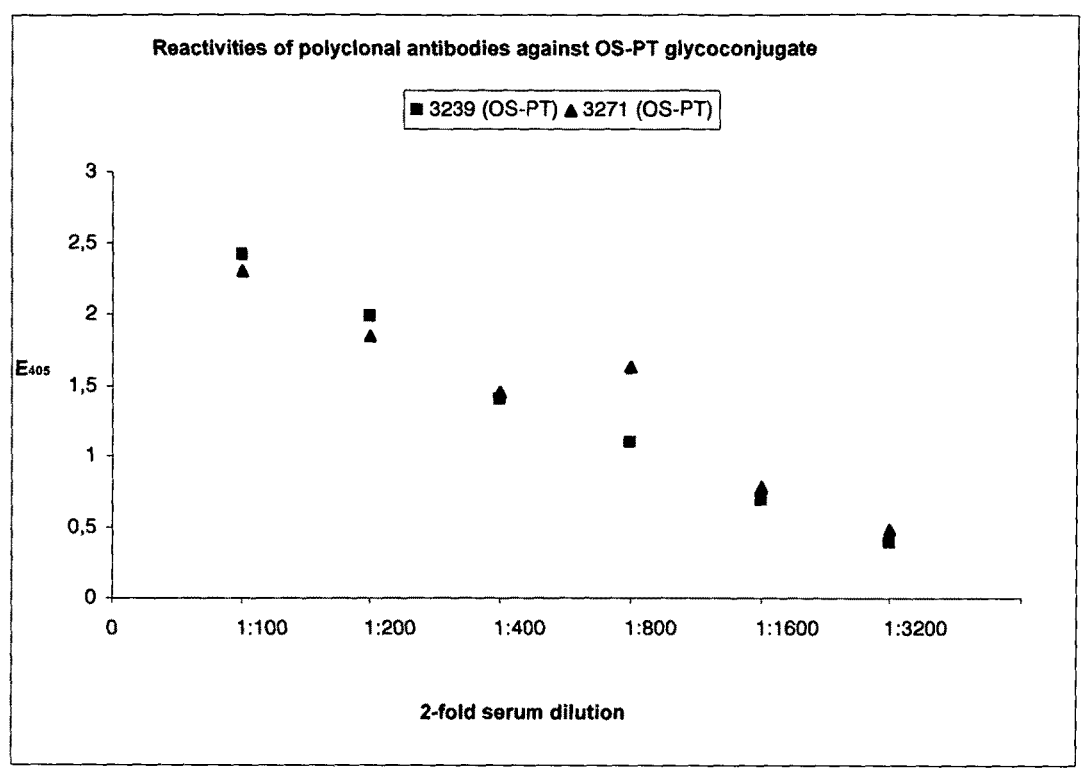
FIG. 7. Reactions of sera against the OS-PT obtained after the third immunization dose of rabbits. Reactivities of sera numbered: 3239 and 3271 were determined by ELISA with *B. pertussis* 186 LOS as a solid phase antigen.
Figure 8:
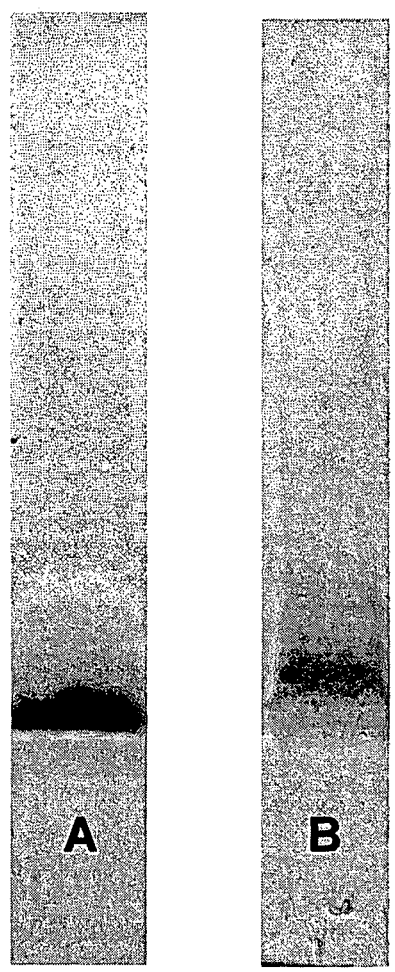
FIG. 8. Silver-stained SDS-PAGE of *B. pertussis* 186 LOS (A) and immunoblots of the LOS with the anti-OS-PT conjugate serum diluted 1:200 (B)

Toxicity analysis of OS-PT relies on the treatment of the CHO cells with the OS-PT preparations (Method 4, FIG. 6A). The culture of the CHO cells in the presence of the OS-PT was compared to the CHO culture in the presence of only PT (positive control, FIG. 6A A) and the CHO cell culture without PT (negative control, FIG. 6A C). In the case of the CHO cells in the presence of PT, the clustering effect was observed in a wide range of tested concentrations (0.06 pg/ml to 0.9 µg/ml) for both the standard PT (FIG. 6A A) and the isolated PT (FIG. 6A E). In contrast, the clustering pattern of the CHO cells was not observed for the OS-PT even when applied at the highest concentration of 130 µg/ml (FIGS. 6A B and 6 A D). Morphologically, the CHO cells in the presence of the OS-PT are indistinguishable from the negative control. In the test of the OS-PT conjugates with the CHO cells we have observed no changes, thus it indicates that the OS-PT is not toxic to the CHO cells.

In the present invention, we demonstrate that by combining PT and the OS, we have prepared a conjugate which showed no enzymatic activity of the toxin. In the CHO cell assay, which is the most sensitive test, the OS-PT was at least $10^6$ times less toxic than PT. Toxicity was not observed even at the highest concentrations. The lack of enzymatic activity of the OS-PT also suggests that this preparation does not induce hypersensitivity effect to histamine as a result of reversion of PTd toxicity. It is also important that the enzymatic inactivation of the toxoids correlates with the lack of pathological disorders typical for PT such as leukocytosis, stimulation of sensitivity to histamine, anaphylaxis, hyperinsulinemia [46].

H. Pertussis Toxin Neutralization Test

We have demonstrated that antibodies obtained by immunization of rabbits with B. pertussis 186 LOS-derived oligosaccharide-pertussis toxin conjugate neutralize toxicity of PT in pertussis toxin neutralization test (Method 4, FIG. 6B). We have observed an inhibition of PT-induced clustering activity for undiluted sera and for sera less than 8-fold diluted in the case of the serum number 3239 and 4-fold diluted in the case of serum number 3271. For example, using serum no. 3239 32-fold diluted, the clustering effect on CHO cells is observed, while it is not observed for a 4-fold dilution (FIG. 6B a and 6B b, respectively). Similarly, using serum no. 3271 64-fold diluted, the cluster pattern is visible, while it cannot be observed for the undiluted serum (FIG. 6B c and 6B d, respectively). The loss of the CHO cells ability to form clusters is the result of neutralization of the pertussis toxin by the sera. The CHO cells without sPT (FIG. 6B e) and the CHO cells with serum were used as a negative control. The sPT present in the CHO culture carried out without serum was used as a positive control (FIG. 6B f).

I. Production of Protective Anti-OS-PT Antibodies

Immunogenicity of the OS-PT conjugate was investigated by immunization of rabbits followed by the determination of antibody levels in the produced immune sera (Method 5). The anti-glycoconjugate antibody titers were determined using ELISA with *B. pertussis* 186 LOS as a solid phase antigen. The anti-OS-PT antibodies reacted with the LOS (FIG. 7). The specific antibody responses with *B. pertussis* 186 LOS were also shown in immunoblotting (FIG. 8).

We have also investigated the level of anti-OS-PT antibodies which are protective against *B. pertussis* in the bactericidal assay (Method 6). The bactericidal titers of the sera corresponding to the maximum dilution of each serum at which 50% of bacterial colonies were killed, was 800-fold and 400-fold (sera no. 3271 and 3239), respectively.

J. MALDI-TOF Mass Spectrometry Analysis of PT and OS-PT Preparations

To define the OS-PT conjugate, MALDI-TOF mass spectrometry analysis was performed (Method 7). We observed that the signals in the spectra of the OS-PT and PT differed. The identified signals in the MALDI-TOF MS of PT correspond to the molecular weights of the subunits: S4 subunit (m/z 12054.84), S3 (m/z 21864.47), S1 (m/z 26220.90), S5 (m/z 11754.57) (FIG. 9 A). The signal for the S2 subunit has not been determined due to excessive signal width of the S3 subunit. The m/z values for PT subunits are consistent with their calculated masses which were established by electrophoresis and sequencing. According to the PT sequence described by Arico and Rappuoli [71] the molecular weights (MW) of subunits are: S1 MW 26219.8, S2 MW 21915.7, S3 MW 21863.9, S4 MW 12053.5, S5 MW 11753.5. Additionally, we have demonstrated, using an "in-source decay" (ISD) experiment that the detailed characterization of PT is further supported by identification of the amino acid sequence of the S4 subunit (VTPTRMLVCGIAAKLG AAASSPDAHV PFCFGKDLK) (SEQ ID NO: 23)(FIG. 9 B). The PT was also characterized by fragment analysis following the tryptic digestion of PT preparation (FIG. 9 C). MALDI-TOF MS/MS analysis of the selected precursor ions originating from the PT fragments provided the sequence information (FIG. 9 D). We observed the fragmentation patterns characteristic for the peptide segments of PT and their sequences were identified. The results of the tryptic digestion of PT agreed with the observations of Tummala et al and Wiliammson et al [71, 72, 75].

MALDI-TOF MS spectrum of the OS-PT did not reveal signals corresponding to the PT subunits which were identified in the spectrum of PT. The signal at m/z 33550 may correspond to the S3-S4 dimer (FIG. 9 E). Different signals in the spectra of PT and the OS-PT indicated that PT subunits were modified by an attachment of the oligosaccharide. However, such glycosylated proteins usually ionize with difficulty in MALDI-TOF MS. In spite of these, an analysis of the digested OS-PT indicated the presence of a few peptides whose m/z values were also observed in spectra of PT fragments (FIG. 9 F). The fragments of PT that were not modified during conjugation include peptides at m/z 881.46, 1033.035, 2114.90, 2332.01, and other peptides summarized in Table 2 (FIG. 9 G). For these at m/z 881.46 and 2114.90, the sequences were determined and showed that the peptides had not been modified by the conjugation with the OS. Peptides containing lysine (K) are potential sites of the OS attachment. Therefore, the lack of signals corresponding to these peptides in spectra of the OS-PT, and their presence in the PT spectra suggests that they contain the lysine residue substituted by an oligosaccharide (potential glycosylation sites, FIG. 9 G). Lysine residues with numbers in the sequence of subunits: S2-110 and 178; S3-38, 121 and 133; S4-50, 61, 78, 96 and 99; S5-52 constitute potential glycosylation sites. Additionally, mass spectrometry analysis of the trypsin-digested OS-PT indicated the presence of a signal which represents a peptide comprising N-terminus of PT. It suggests that the N-terminal amino acid of subunit S1 (in the peptide at m/z 1033.035) is not available for oligosaccharide during conjugation and the OS does not bind to the A oligomer in the OS-PT (FIG. 9 F). Most of the observed signals in the spectra of the digested OS-PT correspond to the S1 peptides, which indicate that this subunit is not modified by the OS. The preservation of the S1 structure is advantageous for a vaccine antigen, since the A oligomer is the most immunoactive subunit of PT.

K. Monitoring of the Oxidation of an Oligosaccharide Using NMR

To define the glycoconjugate of *B. pertussis* 186 oligosaccharide and pertussis toxin, the process of the OS oxidation in the presence of 0.01 M sodium periodate was analyzed using NMR (FIG. 10). Sodium periodate at low concentration cleaves a bond between two adjacent carbon atoms substituted by hydroxyl groups, preferentially in the side group of a Kdo residue of the oligosaccharide. Subsequently it forms a reactive aldehyde group that can react with an amine group of a protein (Scheme 2). However, the NMR analysis indicated also a partial loss of the terminal N-acetylglucosamine during treatment the oligosaccharide of *B. pertussis* 186 LOS with periodate.

The terminal N-acetylglucosamine has been identified on the basis of the typical chemical shift values for the N-acetyl group in the NMR spectra of an oligosaccharide which was not treated with periodate ($\delta_H$ 1.99 ppm and $\delta_c$ 22.8: FIG. 10 A). These resonances are not observed in the NMR spectra of the oligosaccharide following just a 15 minutes of treatment with periodate (FIG. 10 B).

This terminal N-acetylglucosamine is a part of a trisaccharide which is considered as the most immunodominant epitope of *B. pertussis* LOS [47]. The glycoconjugate containing oxidized oligosaccharide devoid of the terminal GlcNAc may not provide a complete immune response. Another fragment of *B. pertussis* 186 LOS, namely a pentasaccharide obtained by deamination. As the deamination preserves the immunodominant epitopes of the LOS, the pentasaccharide seems to be an optimal sugar fragment of *B. pertussis* LOS. The *B. pertussis* 186 LOS-derived pentasaccharide-pertussis toxin conjugate is one aspect of the present invention.

L. MALDI-TOF MS and NMR Spectroscopy Analyses of the Pentasaccharide

The pentasaccharide isolated from *B. pertussis* 186 LOS was analyzed using NMR and MALDI-TOF MS techniques.

The structure of the isolated fragment was determined by two-dimensional NMR spectra (COSY, HSQC, HMBC, FIG. 11 A-C), confirming that the pentasaccharide structure was in agreement with published data [47]. MALDI-TOF MS spectrum contained the main signal at m/z~1044.738, which corresponds to the molecular weight of the pentasaccharide (FIG. 12). The combined data indicate that in the pentasaccharide is composed of the following sugars: N-acetylglucosamine (GlcNAc), L-glycero-D-mannoheptose (LD-Hep), 2,3-diacetamido-2,3-dideoxymannouronic acid (Man2NAc3NAcA), 2,5-anhydro-D-mannose (2,5-anhydroMan), 2-acetamido-4-N-nitrosyl-N-methyl-2,4,6-trideoxy-galactose (L-Fuc2NAc4NNOMe).

Methods

B. pertussis strain 186 was obtained from the Laboratory of Infection Prevention and Nosocomial Infections of the National Institute of Public Health (Warsaw, Poland). Chinese hamster ovary cells (CHO) were purchased from the German Collection of Microorganisms and Cell Cultures (Germany). The Standard for PT (JNIH-5) was obtained from the National Institute for Biological Standards and Control (NIBSC, UK).

Method 1. Isolation of Pertussis Toxin

Isolation of the pertussis toxin was carried out according to the method using ion-exchange chromatography on CM-Sepharose [49, 66]. To a culture medium of *B. pertussis* 186 separated from the bacterial cells by centrifugation, solid ammonium sulfate (390 g/l) was added to precipitate the proteins. Following the incubation for 16 h at 4° C. the preparation was centrifuged (29000×g, 30', 4° C.) the supernatant was discarded and the precipitate was dissolved in 50 mM phosphate buffer at pH 8.0 containing 1 M NaCl. The extract was then centrifuged (17300×g, 30', 4° C.) and the supernatant was saved. The extraction on the precipitate was repeated three times. The extracts were pooled and dialyzed against 50 mM phosphate buffer containing 2 M urea (buffer A) at pH 8.0. After 16-hours dialysis, the pH of the dialysate was adjusted to pH 6.0 with 1 M $H_3PO_4$ and applied to a CM-Sepharose CL-6B (1 cm×16 cm) equilibrated with buffer A at pH 6.0. The isolation process was monitored by measuring the UV absorbance (chromatogram, FIG. 1). The column was washed with the buffer A of pH 6.0 until the stable baseline of the $A_{280}$ value was reached prior to elution of the free proteins. The resin was then washed with buffer A of pH 7.4 to elute the PT from the column (the buffer was changed in the 190 minute of the measurement). After elution of PT, FHA was eluted with 50 mM phosphate buffer of pH 8.0 containing 0.5 M NaCl (the buffer was changed in 300 minute of the measurement). The purification procedure was performed at 4° C. The fractions were analyzed using immunoblotting with a serum directed against the pertussis toxin. Then, the concentrated fractions of PT were dialyzed against 50 mM phosphate buffer at pH 8.0 containing 0.5 M NaCl and 50% glycerol. The PT preparations were analyzed by electrophoresis and immunoblotting using the anti-pertussis toxin antibody. The PT preparations were aliquoted and stored at −75° C.

Method 2. Synthesis and Purification of the Oligosaccharide-Containing Neoglycoconjugate The oligosaccharide was dissolved in 0.01 M aqueous sodium periodate solution ($NaIO_4$). The reaction was carried out in the dark at 24° C. for 1 h. In parallel, the control was prepared, which was 0.01 M solution of $NaIO_4$. After one-hour incubation, 10 μl of sample and control was added to 2 ml of water and the extinction at a wavelength of 225 nm was measured. The oxidation reaction was stopped by addition of ethylene glycol (30 μl) and it was left at 24° C. for an additional 1 hour. The oxidized oligosaccharide was purified by HPLC using molecular sieve chromatography (G3000-PW, TSK). The purified oligosaccharide in its oxidized form was freeze-dried. Subsequently, it was dissolved in 1.5 ml of 0.2 M borate buffer at pH 9.0 and added to the carrier protein. After one-hour incubation at 37° C., 15 mg of sodium cyanoborohydride ($NaBCNH_3$) and a drop of chloroform to prevent bacterial growth were added to the solution. The reaction was carried out for 14 days at 37° C. On the 5th and 10th day after the start of the reaction, additional portions of $NaBCNH_3$ (10 mg) were added. The reaction mixture was fractionated on a G3000-SW column equilibrated with phosphate-buffered saline (PBS, pH 7.5). In the collected fractions, the protein concentration was determined by measuring absorbance at a wavelength of 280 nm. The presence of oligosaccharide was determined by dot-blot reaction using the anti-endotoxin serum obtained by immunization with a bacterial mass of *B. pertussis* 186 and with *B. pertussis* 186 LOS-derived pentasaccharide-tetanus toxoid conjugate. A content of the oligosaccharide in the conjugate was determined by the phenol-sulfuric acid method. Fractions containing the conjugate were concentrated by ultrafiltration and stored at 4° C. with an addition of merthiolate (0.01%).

Method 3. ELISA Test with a Fetuin as a Solid Phase Antigen

Interactions of PT and the OS-PT with fetuin were investigated according to the method described by Isbrucker et al [26]. 96-well plates (Nunc) were coated with fetuin solution (5 μg/ml, 100 μl) in 0.05 M carbonate buffer at pH 9.6 and incubated overnight. The plates were washed five times with TBS (0.1 M) containing 0.1% Tween-20 and blocked with 3% BSA (100 μl) in TBS, for 1 h at 37° C. Following the washing steps, 100 μl of serial dilutions of the OS-PT and PT were added and incubated for 1 h. After washing, the plates were incubated with 100 μl of anti-pertussis toxin serum (Abcam) 10000-fold diluted. The bound anti-toxin antibodies were detected using goat anti-rabbit IgG conjugated with alkaline phosphatase (BioRad) 10000-fold diluted for 90' at 37° C. The free antibodies were washed with TBS and subsequently, a color was developed by addition of the p-nitrophenylphosphate (1.5 mg/ml) in carbonate buffer at pH 9.6 with 1 mM $MgCl_2$. The reaction was stopped after 100 minutes by addition of 100 μl of 1M NaOH. Absorbance was measured at $\lambda$=405 nm using a Perkin Elmer Mikroplate Reader.

Method 4. Toxicity Assay Using CHO Cells

The clustering of the CHO cells in the presence of PT and the OS-PT was determined according to the method described by Hewlett et al. [18]. In brief, the CHO cells were incubated for 24 h with different concentration of the OS-PT (31 pg/ml to 130 μg/ml range) and PT (0.06 pg/ml to 0.9 μg/ml range). Interaction of the preparations with the CHO cells was observed. The CHO cell were cultured in MEMα medium containing 10% fetal bovine serum. The cells cluster-formation was monitored using Axio Vert. A1 microscope (Zeiss).

Pertussis Toxin Neutralization Test

The level of antibodies neutralizing the pertussis toxin activity was investigated in the PT neutralization assay [16, 46]. Two-fold dilutions of the sera (25 μl) were mixed with 25 μl of toxin (120 pg). Following a 3-hours incubation at 37° C., the CHO cells ($1\times10^4$) were added and incubated at 37° C. in a 5% $CO_2$ atmosphere. As a positive control, sPT was applied to the CHO culture without serum. The CHO cells alone and the CHO cells in the presence of sera served as a negative controls. The neutralizing titer was defined as the highest serum dilution resulting in a complete inhibition of the clustering effect induced by the native toxin.

Method 5. Immunization of OS-PT Conjugate

Two Termond White rabbits were immunized subcutaneously in the neck with the OS-PT antigen. The vaccine composition comprised the OS-PT (50 μg) with MPL (0.4 mg) as an adjuvant. Immunizations with the neoglycoconjugate were performed according to the following schedule: (i) the first dose—day 0, (ii) the second dose—day 21, (iii) the third dose—day 42. The vaccination was carried out according to the procedures approved by the Local Ethics Commission at IITD PAN in the Directive 54/2009. After completion of the vaccination, the level of anti-neoglycoconjugate antibodies in the sera was determined.

Method 6. Serum Bactericidal Assay

The rabbit sera were inactivated at 56° C. for 30 min and diluted 10-fold and 2-fold in PBS with 0.15 mM $CaCl_2$, 0.5 mM $MgCl_2$ and 0.1% BSA (buffer A, pH 7.4). *B. pertussis* 186 was diluted to ~300-500 bacteria in 25 µl of buffer A. 140 µl of buffer A was mixed with 45 µl of serum, 25 µl of bacterial suspension and 15 µl of complement (a rabbit complement, Biomed, Lublin). The mixture of bacteria in buffer A with complement and without serum was used as a control. Following an incubation for 60 min at 37° C., 100 µl of each mixture was plated onto charcoal agar containing a sheep blood and incubated for 4 days. The colonies were then counted. The bactericidal titer of serum was defined as the highest dilution at which the 50% of bacterial colonies were killed [30, 39]. The lowest titer giving the desired bactericidal effect was observed for the dilutions of 800-fold and 400-fold.

Method 7. MALDI-TOF MS Analysis

MALDI-TOF MS analyses were performed on Autoflex III and Ultraflex instruments (Bruker Daltonics). Spectra were acquired in negative and positive ion modes. Preparations of PT, the conjugates and the tryptic digest fragments were mixed with appropriate matrices such as: synapinic acid (SA), dihydroxyacetophenone (DHPA), dihydroxybenzoic acid (DHB), a mixture of 2,5-dihydroxybenzoic acid and 2-hydroxy-5-methoxybenzoic acid (sDHB) and α-cyano-4-hydroxycinnamic acid (α-HCCA). The samples were analyzed without desalting or were desalted using $C_4$ resin (Ziptip, Millipore, eluents: ACN/0.1% TFA with increasing content of ACN: 50, 80, 95%) or were dialyzed against 0.1% TFA (Microcon, 10 kDa MWCO). Peptide fragments were separated using a $C_{18}$ column (Dionex) employing a gradient of $H_2O$/0.1% TFA and ACN/0.1% TFA.

The digested preparations were characterized using a trypsin (Sequencing Grade Modified Trypsin, Porcine, Promega) according to the manufacturer's instruction. Briefly, 20 µg of protein was dissolved in the reaction mixture containing 2 M DTT, 0.1% SDS, and filled up with Tris-HCl buffer (pH 8.0) to the volume of 0.1 ml. The mixture was heated at 95° C. for 15 minutes. After cooling, a trypsin was added to achieve a trypsin:protein ratio of 1:20 (w/w) and the mixture was incubated at 37° C. for 24 hours. The reaction was terminated by freezing the sample. The digestion products were analyzed directly by MALDI-TOF MS and using the reverse-phase chromatography ($C_{18}$, Dionex) interfaced to a MALDI-TOF MS mass spectrometry (Ultraflex). The preparations were dissolved in an initial solvent A: 0.1% TFA in water. Subsequently, a linear gradient at a flow rate of 300 nl/min was applied starting with 2% of solvent B: 0.1% TFA in ACN to 100% of solvent B. The separated peptides were analyzed by MALDI-TOF MS and were subjected to the laser-induced fragmentation (LID). Identification of the peptide sequences was performed with Biotools software and a Mascot database.

Method 8. Isolation of the Pentasaccharide from *B. pertussis* 186 LOS

The pentasaccharide was obtained by deamination of *B. pertussis* 186 lipooligosaccharide (Scheme 3). 50 mg LOS was suspended in a solution of water/5% sodium nitrite/30% acetic acid (1:1:1, v/v/v) and stirred for 4 hours at room temperature. The products of LOS deamination were separated by ultracentrifugation (2 h, 200000×g, 4° C.).

The supernatant was freeze-dried and the product was purified on a column of Bio-Gel P-2 (Bio-Rad) in a pyridine/acetic acid/water buffer, pH 5.6. The yield of the pentasaccharide isolation was ~4 mg.

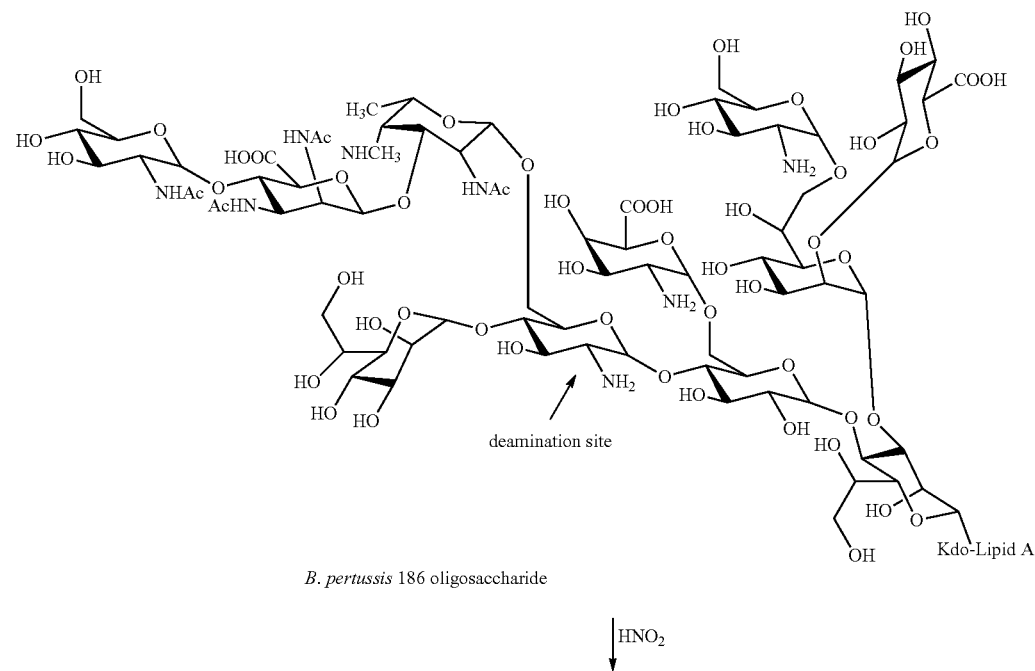

Scheme 4. Preparation of the pentasaccharide by deamination of *B. pertussis* 186 LOS.

-continued

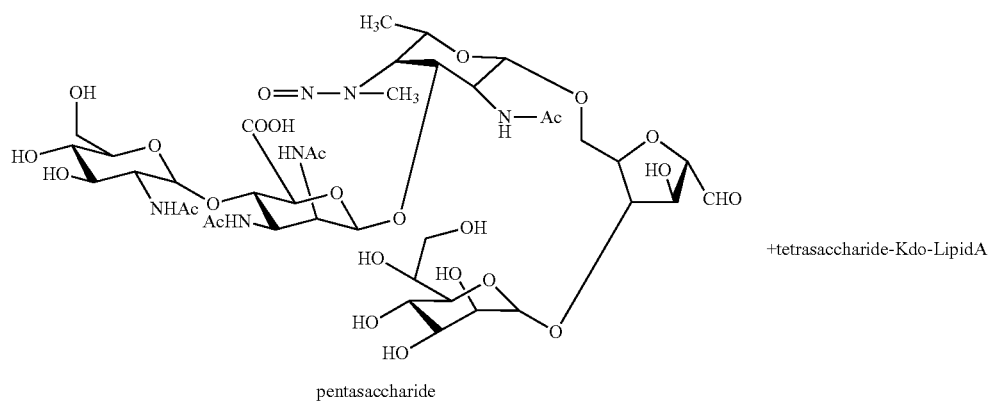

pentasaccharide  +tetrasaccharide-Kdo-LipidA

The precipitated fraction of the LOS obtained by deamination contains a heterogeneous mixture of core oligosaccharides differing in the number of sugar residues (Scheme 4), which were identified by MALDI-TOF MS (FIG. 12 B). During the deamination of *B. pertussis* LOS, the sugar residues containing amine groups are lost. The cleavage can include the terminal pentasaccharide, galactosaminuronic acid and glucosamine. A core fragment devoid of the terminal pentasaccharide and the galactosaminuronic acid with calculated molecular mass of 1121.35 Da was identified as a ion of type $[M-H_2O—H]^{1-}$ at m/z 1102.5734 in the negative-ion mode spectrum (). An oligosaccharide fragment with monoisotopic mass of 960.28 Da obtained by cleavage of the terminal pentasaccharide, galactosaminuronic acid and glucosamine corresponds to an ion at m/z 959.4448 and its anhydro form at 941.4750 (*).

Scheme 5. *B. pertussis* 186 OS deamination products containing the inner core oligosaccharide (OS was obtained after acid hydrolysis of the deaminated LOS).

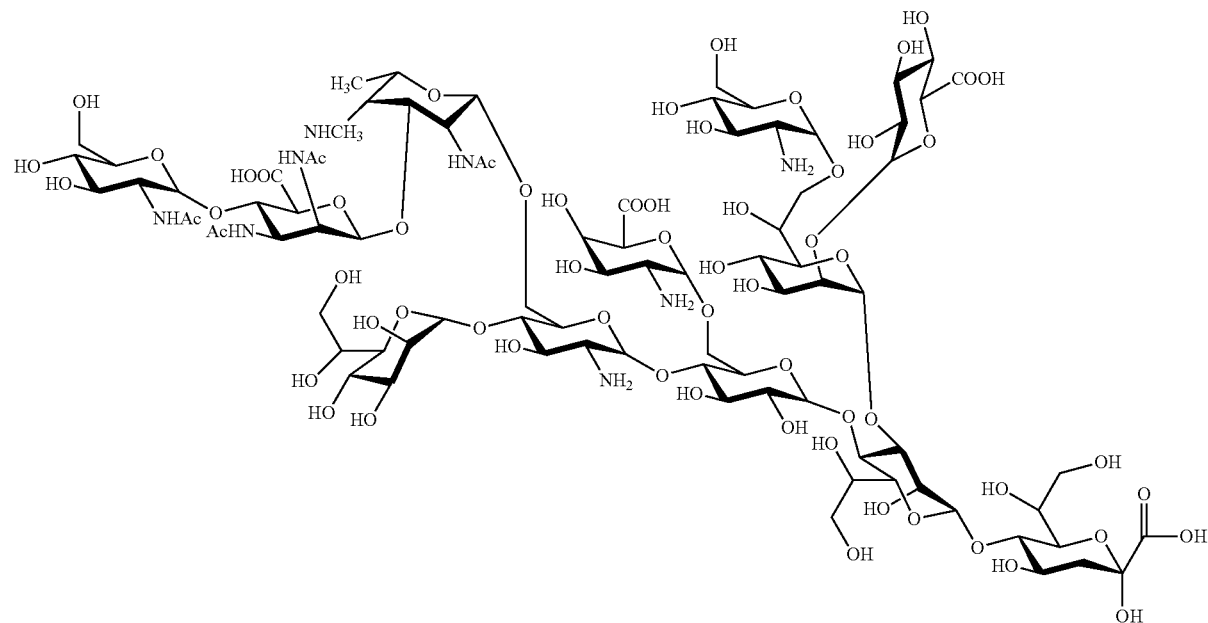

exact mass: 2310.81

-continued

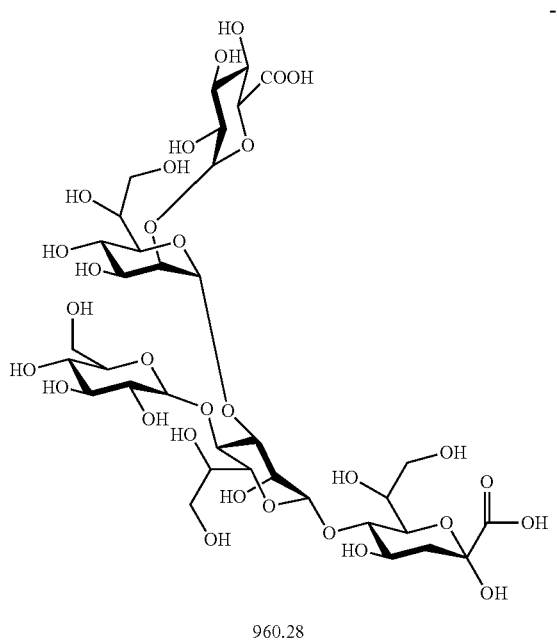

960.28

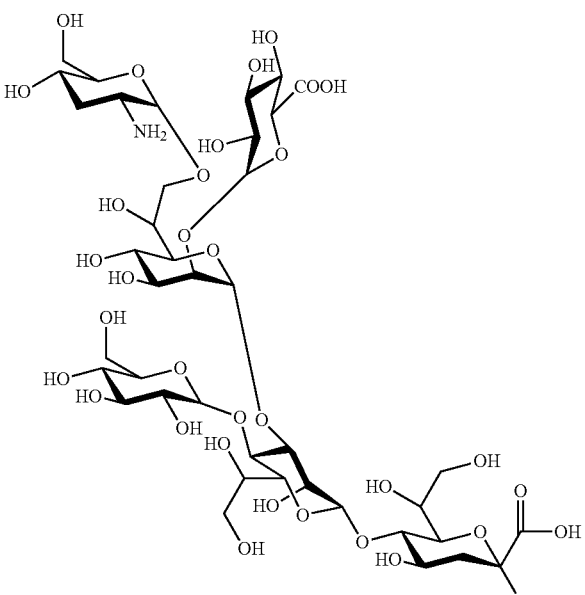

1121.35

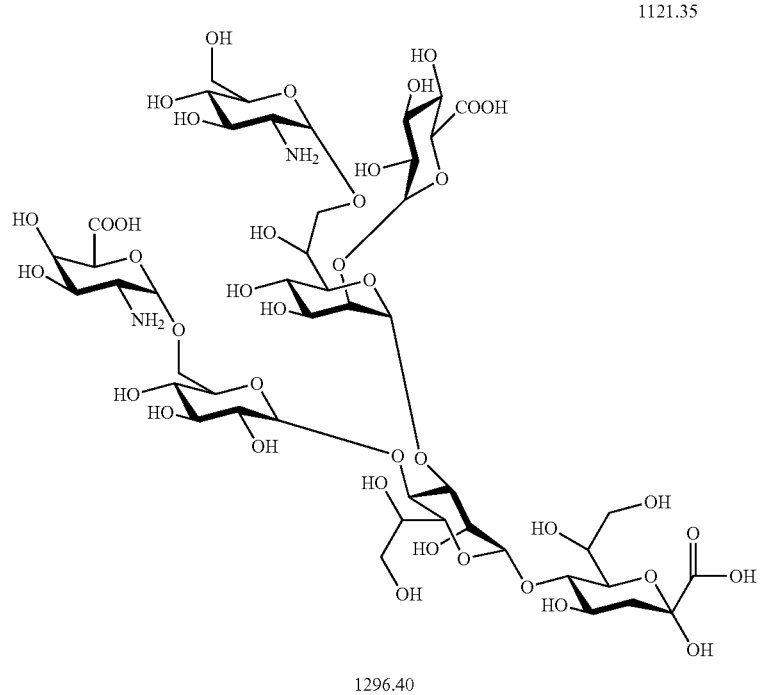

1296.40

Method 9. NMR Spectroscopy

NMR spectra of the isolated pentasaccharide were obtained for 10% $^2H_2O$ solution with a Bruker Avance III 600 MHz spectrometer (Bruker). Spectra were acquired at 30° C. and the WATERGATE pulse sequence was applied.

REFERENCES

1. Amano, K., Fukushi, K., and Watanabe, M. (1990). Biochemical and immunological comparison of lipopolysaccharides from *Bordetella* species. J. Gen. Microbiol. 136, 481-487.

2. Antoine, R., and Locht, C. (1994). The NAD-glycohydrolase activity of the pertussis toxin S1 subunit. Involvement of the catalytic HIS-35 residue. J. Biol. Chem. 269, 6450-6457.

3. Antoine, R., Tallett, A., Van Heyningen, S., and Locht, C. (1993). Evidence for a catalytic role of glutamic acid 129 in the NAD-glycohydrolase activity of the pertussis toxin S1 subunit. J. Biol. Chem. 268, 24149-24155.

4. Avci F. Y., Li X., Tsuji M., and Kasper D. L. (2012). A novel mechanism for glycoconjugate vaccine activation of the adaptive immune system. Nat Med. 17: 1602-1609.

5. Le Blay, K., Caroff, M., Blanchard, F., Perry, M. B., and Chaby, R. (1996). Epitopes of *Bordetella pertussis* lipopolysaccharides as potential markers for typing of isolates with monoclonal antibodies. Microbiology 142, 971-978.
6. Bobbitt J. M. (1956). Periodate oxidation of carbohydrate. Adv Carbohydrate Chem. 48:1-41.
7. Burns, D. L., Kenimer, J. G., and Manclark, C. R. (1987). Role of the A subunit of pertussis toxin in alteration of Chinese hamster ovary cell morphology. Infect Immun 55, 24-28.
8. Burns, D. L., Hausman, S. Z., Lindner, W., Robey, F. A., and Manclark, C. R. (1987). Structural characterization of pertussis toxin A subunit. J. Biol. Chem. 262, 17677-17682.
9. Caroff, M., Chaby, R., Karibian, D., Perry, J., Deprun, C., and Szabo, L. (1990). Variations in the carbohydrate regions of Bordetella pertussis lipopolysaccharides: electrophoretic, serological, and structural features. J Bacteriol 172, 1121-1128.
10. Caroff, M., Brisson, J., Martin, A., and Karibian, D. (2000). Structure of the Bordetella pertussis 1414 endotoxin. FEBS Lett. 477, 8-14.
11. Cherry, J. D. (2012). Why Do Pertussis Vaccines Fail? Pediatrics 129, 968-970.
12. Connelly, C. E., Sun, Y., and Carbonetti, N. H. (2012). Pertussis toxin exacerbates and prolongs airway inflammatory responses during Bordetella pertussis infection. Infect. Immun. 80, 4317-4332.
13. Duan J., Avci F. Y., and Kasper D. L. (2008) Microbial carbohydrate depolymerization by antigen-presenting cells: Deamination prior to presentation by the MHC II pathway. PNAS. 105: 5183-5188.
14. Dur, A., Caroff, M., Chaby, R., and Szabo, L. (1978). Novel Type of Endotoxin Structure Present in Bordetella pertussis. Isolation of Two Different Polysaccharides Bound to Lipid A. Eur J Biochem 84, 579-589.
15. Flak, T. A., and Goldman, W. E. (1999). Signalling and cellular specificity of airway nitric oxide production in pertussis. Cellular Microbiology 1, 51-60.
16. Gillenius, P., Jäätmaa E., Askelöf P., Granström M., and Tiru M. (1985) The Standardization of an Assay for Pertussis Toxin and Antitoxin in Microplate Culture of Chinese Hamster Ovary Cells. Journal of biological standardization. 13, 61-66.
17. Gomez, S. R., Xing, D. K.-L., Corbel, M. J., Coote, J., Parton, R., and Yuen, C.-T. (2006). Development of a carbohydrate binding assay for the B-oligomer of pertussis toxin and toxoid. Anal. Biochem. 356, 244-253.
18. De Gouw, D., Diavatopoulos, D. A., Bootsma, H. J., Hermans, P. W. M., and Mooi, F. R. (2011). Pertussis: a matter of immune modulation. FEMS Microbiol. Rev. 35, 441-474.
19. Gzyl, A., Augustynowicz, E., Rabczenko, D., Gniadek, G., and Slusarczyk, J. (2004a). Pertussis in Poland. Int J Epidemiol 33, 358-365.
20. Gzyl, A., Gniadek, G., Augustynowicz, E., Rabczenko, D., Husejnow, B., Zawadka, M., and Slusarczyk, J. (2004b). [Increase in the incidence of pertussis and quality of whole-cell pertussis component of the DTP vaccine produced in Poland. Part II. Consistency of control and production]. Przegl Epidemiol 58, 641-648.
21. Heininger, U. (2001). Recent progress in clinical and basic pertussis research. Eur. J. Pediatr. 160, 203-213.
22. Hewlett, E. L., Sauer, K. T., Myers, G. A., Cowell, J. L., and Guerrant, R. L. (1983). Induction of a novel morphological response in Chinese hamster ovary cells by pertussis toxin. Infect Immun 40, 1198-1203.
23. Higgins, S. C., Jarnicki, A. G., Lavelle, E. C., and Mills, K. H. G. (2006). TLR4 Mediates Vaccine-Induced Protective Cellular Immunity to Bordetella pertussis: Role of IL-17-Producing T Cells. J Immunol 177, 7980-7989.
24. Higgs, R., Higgins, S. C., Ross, P. J., and Mills, K. H. G. (2012). Immunity to the respiratory pathogen Bordetella pertussis. Mucosal Immunol 5, 485-500.
25. Ibsen, P. H. (1996). The effect of formaldehyde, hydrogen peroxide and genetic detoxification of pertussis toxin on epitope recognition by murine monoclonal antibodies. Vaccine 14, 359-368.
26. Isbrucker, R. A., Bliu, A., and Prior, F. (2010). Modified binding assay for improved sensitivity and specificity in the detection of residual pertussis toxin in vaccine preparations. Vaccine 28, 2687-2692.
27. Jennings, H. J., and Lugowski, C. (1981). Immunochemistry of groups A, B, and C meningococcal polysaccharide-tetanus toxoid conjugates. J Immunol 127, 1011-1018.
28. Jennings, H. J., Lugowski, C., and Ashton, F. E. (1984). Conjugation of meningococcal lipopolysaccharide R-type oligosaccharides to tetanus toxoid as route to a potential vaccine against group B Neisseria meningitidis. Infection and Immunity 43, 407-412.
29. Kaslow, H. R., and Burns, D. L. (1992). Pertussis toxin and target eukaryotic cells: binding, entry, and activation. FASEB J. 6, 2684-2690.
30. Kaslow, H. R., Lim, L. K., Moss, J., and Lesikar, D. D. (1987). Structure-activity analysis of the activation of pertussis toxin. Biochemistry 26, 123-127.
31. Kimura, M., and Kuno-Sakai, H. (1990). Developments in pertussis immunisation in Japan. Lancet 336, 30-32.
32. Kubler-Kielb, J. (2011). Conjugation of LPS-derived oligosaccharides to proteins using oxime chemistry. Methods Mol. Biol. 751, 317-327.
33. Kubler-Kielb, J., Vinogradov, E., Ben-Menachem, G., Pozsgay, V., Robbins, J. B., and Schneerson, R. (2008). Saccharide/protein conjugate vaccines for Bordetella species: preparation of saccharide, development of new conjugation procedures, and physico-chemical and immunological characterization of the conjugates. Vaccine 26, 3587-3593.
34. Kubler-Kielb, J., Vinogradov, E., Lagergård, T., Ginzberg, A., King, J. D., Preston, A., Maskell, D. J., Pozsgay, V., Keith, J. M., Robbins, J. B., et al. (2011). Oligosaccharide conjugates of Bordetella pertussis and bronchiseptica induce bactericidal antibodies, an addition to pertussis vaccine. Proc. Natl. Acad. Sci. U.S.A. 108, 4087-4092.
35. Kubler-Kielb, J., and Pozsgay, V. (2005). A New Method for Conjugation of Carbohydrates to Proteins Using an Aminooxy-Thiol Heterobifunctional Linker. J. Org. Chem. 70, 6987-6990.
36. Lobet, Y., Feron, C., Dequesne, G., Simoen, E., Hauser, P., and Locht, C. (1993). Site-specific alterations in the B oligomer that affect receptor-binding activities and mitogenicity of pertussis toxin. J. Exp. Med. 177, 79-87.
37. Locht, C. (1999). Molecular aspects of Bordetella pertussis pathogenesis. Int. Microbiol. 2, 137-144.
38. Locht, C., Coutte, L, and Mielcarek, N. (2011). The ins and outs of pertussis toxin. FEBS J. 278, 4668-4682.
39. Mahon, B. P., Ryan, M. S., Griffin, F., and Mills, K. H. (1996). Interleukin-12 is produced by macrophages in response to live or killed Bordetella pertussis and enhances the efficacy of an acellular pertussis vaccine by promoting induction of Th1 cells. Infect. Immun. 64, 5295-5301.

40. Mangmool, S., and Kurose, H. (2011). Gi/o Protein-Dependent and -Independent Actions of Pertussis Toxin (PTX). Toxins 3, 884-899.
41. Marzouqi, I., Richmond, P., Fry, S., Wetherall, J., and Mukkur, T. (2010). Development of improved vaccines against whooping cough: current status. Hum Vaccin 6, 543-553.
42. Metz, B., Kersten, G., F. A., Jong A., Meiring H., Hove J. Identification of formaldehyde-induced modification in proteins: reactions with diphteria toxin.
43. McQuillen, D. P., Gulati, S., and Rice, P. A. (1994). Complement-mediated bacterial killing assays. In Methods in Enzymology, P. M. B. Virginia L. Clark, ed. (Academic Press), pp. 137-147.
44. Mielcarek, N., Debrie, A.-S., Raze, D., Bertout, J., Rouanet, C., Younes, A. B., Creusy, C., Engle, J., Goldman, W. E., and Locht, C. (2006). Live attenuated B. pertussis as a single-dose nasal vaccine against whooping cough. PLoS Pathog. 2, e65. Doi:10.1371/journal.ppat.0020065.
45. Mountzouros, K. T., Kimura, A., and Cowell, J. L. (1992). A bactericidal monoclonal antibody specific for the lipooligosaccharide of Bordetella pertussis reduces colonization of the respiratory tract of mice after aerosol infection with B. pertussis. Infect. Immun. 60, 5316-5318.
46. Nencioni, L., Pizza, M., Bugnoli, M., De Magistris, T., Di Tommaso, A., Giovannoni, F., Manetti, R., Marsili, I., Matteucci, G., and Nucci, D. (1990). Characterization of genetically inactivated pertussis toxin mutants: candidates for a new vaccine against whooping cough. Infect Immun 58, 1308-1315.
47. Niedziela, T., Letowska, I., Lukasiewicz, J., Kaszowska, M., Czarnecka, A., Kenne, L., and Lugowski, C. (2005). Epitope of the vaccine-type Bordetella pertussis strain 186 lipooligosaccharide and antiendotoxin activity of antibodies directed against the terminal pentasaccharide-tetanus toxoid conjugate. Infect. Immun. 73, 7381-7389.
48. Nogimori, K., Tamura, M., Yajima, M., Ito, K., Nakamura, T., Kajikawa, N., Maruyama, Y., and Ui, M. (1984). Dual mechanisms involved in development of diverse biological activities of islet-activating protein, pertussis toxin, as revealed by chemical modification of lysine residues in the toxin molecule. Biochim. Biophys. Acta (BBA) 801, 232-243.
49. Ozcengiz, E., Kilinç, K., Büyüktanir, O., and Günalp, A. (2004). Rapid purification of pertussis toxin (PT) and filamentous hemagglutinin (FHA) by cation-exchange chromatography. Vaccine 22, 1570-1575.
50. Pichichero, M. E., Rennels, M. B., Edwards, K. M., Blatter, M. M., Marshall, G. S., Bologa, M., Wang, E., and Mills, E. (2005). Combined tetanus, diphtheria, and 5-component pertussis vaccine for use in adolescents and adults. JAMA 293, 3003-3011.
51. Pizza, M., Covacci, A., Bartoloni, A., Perugini, M., Nencioni, L., De Magistris, M., Villa, L., Nucci, D., Manetti, R., Bugnoli, M., et al. (1989). Mutants of pertussis toxin suitable for vaccine development. Science 246, 497-500.
52. Quentin-Millet, M. J., Arminjon, F., Danve, B., Cadoz, M., and Armand, J. (1988). Acellular pertussis vaccines: evaluation of reversion in a nude mouse model. Journal of Biological Standardization 16, 99-108.
53. Sato, H., and Sato, Y. (1999). Experience with Diphtheria Toxoid-Tetanus Toxoid-Acellular Pertussis Vaccine in Japan. Clinical Infectious Diseases 28, S124-S130.
54. Sato, H., Sato, Y., Ito, A., and Ohishi, I. (1987). Effect of monoclonal antibody to pertussis toxin on toxin activity. Infect. Immun. 55, 909-915.
55. Sato, Y., Arai, H., and Suzuki, K. (1974). Leukocytosis-Promoting Factor of Bordetella pertussis III. Its Identity with Protective Antigen. Infect Immun 9, 801-810.
56. Schmidt, M. A., and Schmidt, W. (1989). Inhibition of pertussis toxin binding to model receptors by antipeptide antibodies directed at an antigenic domain of the S2 subunit. Infect Immun 57, 3828-3833.
57. Schmidt, M. A., Raupach, B., Szulczynski, M., and Marzillier, J. (1991). Identification of linear B-cell determinants of pertussis toxin associated with the receptor recognition site of the S3 subunit. Infect Immun 59, 1402-1408.
58. Schmitt, C. K., Meysick, K. C., and O'Brien, A. D. (1999). Bacterial toxins: friends or foes? Emerg Infect Dis 5, 224-234.
59. Seabrook, R. N., Atkinson, T., and Irons, L. I. (1991). A spectroscopic and conformational study of pertussis toxin. Eur J Biochem 198, 741-747.
60. Sekura, R. D., Fish, F., Manclark, C. R., Meade, B., and Zhang, Y. L. (1983). Pertussis toxin. Affinity purification of a new ADP-ribosyltransferase. J. Biol. Chem. 258, 14647-14651.
61. Sekura, R. D., Zhang, Y. L., Roberson, R., Acton, B., Trollfors, B., Tolson, N., Shiloach, J., Bryla, D., Muir-Nash, J., and Koeller, D. (1988). Clinical, metabolic, and antibody responses of adult volunteers to an investigational vaccine composed of pertussis toxin inactivated by hydrogen peroxide. J. Pediatr. 113, 806-813.
62. Sheu, G. C., Wo, Y. Y., and Lu, C. H. (1997). Preparation and characterization of Pertussis toxin subunits. ISSN 30, 182-193.
63. Sheu, G. C., Wo, Y. Y., Yao, S. M., Chou, F. Y., Hsu, T. C., Ju, C. L., Cheng, Y., Chang, S. N., and Lu, C. H. (2001). Characteristics and potency of an acellular pertussis vaccine composed of pertussis toxin, filamentous hemagglutinin, and pertactin. J Microbiol Immunol Infect 34, 243-251.
64. Skelton, S. K., and Wong, K. H. (1990). Simple, efficient purification of filamentous hemagglutinin and pertussis toxin from Bordetella pertussis by hydrophobic and affinity interaction. J. Clin. Microbiol. 28, 1062-1065.
65. Stein, P. E., Boodhoo, A., Armstrong, G. D., Cockle, S. A., Klein, M. H., and Read, R. J. (1994). The crystal structure of pertussis toxin. Structure 2, 45-57.
66. Tamura, M., Nogimori, K., Murai, S., Yajima, M., Ito, K., Katada, T., Ui, M., and Ishii, S. (1982). Subunit structure of islet-activating protein, pertussis toxin, in conformity with the A-B model. Biochemistry 21, 5516-5522.
67. Tan, Y., Fleck, R. A., Asokanathan, C., Yuen, C.-T., Xing, D., Zhang, S., and Wang, J. (2013). Confocal microscopy study of pertussis toxin and toxoids on CHO-cells. Hum Vaccin Immunother 9.
68. Tefon, B. E., Maass, S., Ozcengiz, E., Becher, D., Hecker, M., and Ozcengiz, G. (2011). A comprehensive analysis of Bordetella pertussis surface proteome and identification of new immunogenic proteins. Vaccine 29, 3583-3595.
69. Trollfors, B., Taranger, J., Lagergård, T., Lind, L., Sundh, V., Zackrisson, G., Lowe, C. U., Blackwelder, W., and Robbins, J. B. (1995). A Placebo-Controlled Trial of a Pertussis-Toxoid Vaccine. N Eng J Med 333, 1045-1050.
70. Trollfors, B., Lagergård, T., Taranger, J., Bergfors, E., Schneerson, R., and Robbins, J. B. (2001). Serum immunoglobulin G antibody responses to Bordetella pertussis lipooligosaccharide and B. parapertussis lipopolysaccharide in children with pertussis and parapertussis. Clin. Diagn. Lab. Immunol. 8, 1015-1017.
71. Tummala, M., Hu, P., Lee, S.-M., Robinson, A., and Chess, E. (2008). Characterization of pertussis toxin by LC-MS/MS. Anal. Biochem. 374, 16-24.
72. Tummala, M., Lee, S.-M., Chess, E., and Hu, P. (2010). Characterization of pertussis toxoid by two-dimensional liquid chromatography-tandem mass spectrometry. Anal. Biochem. 401, 295-302.
73. Weiss, A. A., Mobberley, P. S., Fernandez, R. C., and Mink, C. M. (1999). Characterization of Human Bactericidal Antibodies to Bordetella pertussis. Infect Immun 67, 1424-1431.
74. Weiss, A. A., Patton, A. K., Millen, S. H., Chang, S.-J., Ward, J. I., and Bernstein, D. I. (2004). Acellular pertussis vaccines and complement killing of Bordetella pertussis. Infect. Immun. 72, 7346-7351.
75. Williamson, Y. M., Moura, H., Schieltz, D., Rees, J., Woolfitt, A. R., Pirkle, J. L., Sampson, J. S., Tondella, M. L., Ades, E., Carlone, G., et al. (2010). Mass spectrometric analysis of multiple pertussis toxins and toxoids. J. Biomed. Biotechnol. 2010, 942365.
76. Witvliet, M. H., Burns, D. L., Brennan, M. J., Poolman, J. T., and Manclark, C. R. (1989). Binding of pertussis toxin to eucaryotic cells and glycoproteins. Infect Immun 57, 3324-3330.
77. Wong, K. H., and Skelton, S. K. (1988). New, practical approach to detecting antibody to pertussis toxin for public health and clinical laboratories. J Clin Microbiol 26, 1316-1320.
78. Woodword M. P, Young W. W., and Bloodgood R. A. (1985) Detection of monoclonal antibodies specific for carbohydrate epitopes using peroxidate oxidation. JIM 78, 143-153.
79. Xing, D., Das, R. G., Newland, P., and Corbel, M. (2002). Comparison of the bioactivity of reference preparations for assaying Bordetella pertussis toxin activity in vaccines by the histamine sensitisation and Chinese hamster ovary-cell tests: assessment of validity of expression of activity in terms of protein concentration. Vaccine 20, 3535-3542.
80. Xing, D., Yuen, C.-T., Asokanathan, C., Rigsby, P., and Horiuchi, Y. (2012). Evaluation of an in vitro assay system as a potential alternative to current histamine sensitization test for acellular pertussis vaccines. Biologicals 40, 456-465.
81. EP0471954A2 Alan, K., Michel, B., and L, C. J. (1991). Immunogenic Conjugates Of Nontoxic Oligosaccharide Derived From Bordetella Pertussis Lipooligosaccharide.
82. US005445817 Schneerson, R., Levi, L., Robbins, J. (1995) Pertussis toxin used as a carrier protein with non-charged saccharides in conjugate vaccines
83. US006168928B1 Read, R., Stein, P., E., Cockle, S. A., Oomen, R., Loosmore S., Klein M., Armstrong G. D., Hazes, B., (2001) Modification of pertussis toxin.
84. US20100158937A1 KUBLER-KIELB, J. [US], POZSGAY, V. [US], LAGERGARD, T. [SE], BEN-MENACHEM, G. [US], SCHNEERSON, R. [US], VINOGRADOV, E. [CA], and GINZBERG, A. [US] (2010). METHODS FOR CONJUGATION OF OLIGOSACCHARIDES OR POLYSACCHARIDES TO PROTEIN CARRIERS THROUGH OXIME LINKAGES VIA 3-DEOXY-D-MANNO-OCTULSONIC ACID (US).

The invention claimed is:

1. A method for preparing a glycoconjugate comprising a *B. pertussis* lipooligosaccharide (LOS)-derived oligosaccharide (OS) or an oligosaccharide fragment of the *B. pertussis* LOS, and the pertussis toxin (PT) wherein the method comprises:
   a. culturing of *B. pertussis*;
   b. isolation of a *B. pertussis* LOS-derived OS or an OS fragment of the *B. pertussis* LOS from the cultured *B. pertussis*;
   c. isolation of PT from *B. pertussis* culture medium;
   d. activation of the *B. pertussis* LOS-derived OS or the OS fragment of the *B. pertussis* LOS;
   e. conjugation of the activated *B. pertussis* LOS-derived OS or the activated OS fragment of the *B. pertussis* LOS, and PT by covalent linking of the activated *B. pertussis* LOS-derived OS or the activated OS fragment of the *B. pertussis* LOS, to free amino groups of lysine residues of pertussis toxin at pH=9 to provide a glycoconjugate; and
   f. purification of the glycoconjugate;
      wherein the content of the *B. pertussis* LOS-derived OS or the OS fragment of the *B. pertussis* LOS in the glycoconjugate with PT is 30-50% of the total weight of the glycoconjugate.

2. The method according to claim 1 characterized in that the *B. pertussis* is cultured in Stainer-Scholte liquid medium with addition of (2,6-di-O-methyl)-B-cyclodextrin.

3. The method according to claim 1, characterized in that the *B. pertussis* LOS-derived OS or the OS fragment of the *B. pertussis* LOS is activated with sodium periodate.

4. The method according to claim 1, characterized in that the conjugation reaction in e) is a reductive amination reaction.

5. The method according to claim 1, characterized in that the conjugation in e) is carried out in 0.2 M borate buffer.

6. A glycoconjugate comprising the *B. pertussis* LOS-derived OS or the OS fragment of the *B. pertussis* LOS, and the PT, wherein the glycoconjugate is made by the method of claim 1.

7. A pharmaceutical composition comprising the glycoconjugate according to claim 6 and a pharmaceutically acceptable carrier.

8. A vaccine composition comprising the glycoconjugate according to claim 6 and a pharmaceutically acceptable carrier and optionally an adjuvant.

9. A glycoconjugate comprising the *B. pertussis* LOS-derived OS or the OS fragment of the *B. pertussis* LOS, directly linked by a covalent bond to free amino groups of lysine residues of PT, wherein the content of the *B. pertussis* LOS-derived OS or the OS fragment of the *B. pertussis* LOS in the glycoconjugate with PT is 30-50% of the total weight of the glycoconjugate.

10. The glycoconjugate according to claim 9, characterized in that the *B. pertussis* LOS-derived OS or the OS fragment of the *B. pertussis* LOS is selected from the group consisting of: a core oligosaccharide (incomplete glycoform, R) of *B. pertussis* LOS, a distal oligosaccharide of *B. pertussis* LOS, and the OS fragment of the *B. pertussis* LOS.

11. A vaccine composition comprising the glycoconjugate according to claim 9 and a pharmaceutically acceptable carrier and optionally an adjuvant.

12. The glycoconjugate according to claim 9, characterized in that the *B. pertussis* LOS-derived OS or the OS fragment of the *B. pertussis* LOS is selected from the group consisting of oligosaccharides of Formula 1

α-D-GlcpNAc-(1-4)-β-D-Manp2NAc3NAcA-(1-3)-β-L-Fucp2NAc4NMe-(1-6)-α-D-GlcpN-(1-4)-β-D-Glcp-(1-4)-L-α-D-Hepp-(1-5)-Kdop with branches:
α-D-GalpNA-(1-6)+ at the α-D-GlcpN-(1-4) residue
α-D-GalpA-(1-2)-L-α-D-Hepp-(1-3)+ with α-D-GlcpN-(1-7)+ branch, on L-α-D-Hepp-(1-5)
L-α-D-Hepp-(1-4)+ on β-D-Glcp
[EtNPP]$_{n=0,1}$ at position 4 of Kdop, or Formula 2

α-D-GlcpN-(1-4)-β-D-Glcp-(1-4)-L-α-D-Hepp-(1-5)-Kdop with branches:
α-D-GalpNA-(1-6)+ at α-D-GlcpN-(1-4)
α-D-GlcpA-(1-2)-L-α-D-Hepp-(1-3)+ with α-D-GlcpN-(1-7)+ branch
L-α-D-Hepp-(1-4)+ on β-D-Glcp
[EtNPP]$_{n=0,1}$ at position 4 of Kdop, or Formula 3

α-D-GlcpNAc-(1-4)-β-D-Manp2NAc3NAcA-(1-3)-β-L-Fucp2NAc4NMe, or

-continued

Formula 4

β-D-Manp2NAc3NAcA-(1-3)-β-L-Fucp2NAc4NMe-(1-6)-α-D-GlcpN-(1-4)-β-D-Glcp-(1-4)L-α-D-Hepp-(1-5)-Kdop-CHO, and
|
L-α-D-Hepp-(1-4)+

Formula 5

α-D-GlcpNAc-(1-4)-β-D-Manp2NAc3NAcA-(1-3)-β-L-Fucp2NAc4N(NO)Me-(1-6)-2,5-anhydroMan-CHO.
|
L-α-D-Hepp-(1-4)+

13. A method of treating a *Bordetella pertussis* infection, comprising administering the pharmaceutical composition as defined in claim 7 to a subject in need thereof.

14. A method of inducing an immune response against *B. pertussis*, comprising administering the vaccine composition as defined in claim 8 to a subject.

15. A method of treating a *Bordetella pertussis* infection, comprising administering the vaccine composition as defined in claim 8 to a subject in need thereof.

16. A method of inducing an immune response against *B. pertussis*, comprising administering the vaccine composition as defined in claim 11 to a subject.

17. A method of treating a *Bordetella pertussis* infection, comprising administering the vaccine composition as defined in claim 11 to a subject in need thereof.

* * * * *

UNITED STATES PATENT AND TRADEMARK OFFICE
CERTIFICATE OF CORRECTION

PATENT NO.          : 9,878,051 B2  
APPLICATION NO.     : 14/896222  
DATED               : January 30, 2018  
INVENTOR(S)         : Sabina Koj et al.

Page 1 of 1

It is certified that error appears in the above-identified patent and that said Letters Patent is hereby corrected as shown below:

On the Title Page

Item (30):  
"404247",  
Should read:  
--P.404247--

Signed and Sealed this  
Thirtieth Day of October, 2018

Andrei Iancu  
*Director of the United States Patent and Trademark Office*